US011788109B2

(12) United States Patent
Sasahara et al.

(10) Patent No.: US 11,788,109 B2
(45) Date of Patent: Oct. 17, 2023

(54) MICROORGANISM AND METHOD FOR PRODUCING GAMMA-GLUTAMYL-VALYL-GLYCINE

(71) Applicant: AJINOMOTO CO., INC., Tokyo (JP)

(72) Inventors: Ayako Sasahara, Kawasaki (JP); Takayuki Ito, Kawasaki (JP); Hiroyuki Nozaki, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/911,731

(22) Filed: Mar. 5, 2018

(65) Prior Publication Data
US 2018/0195103 A1 Jul. 12, 2018

Related U.S. Application Data

(63) Continuation of application No. PCT/JP2016/075896, filed on Sep. 2, 2016.

(30) Foreign Application Priority Data

Sep. 4, 2015 (JP) ................. 2015-175112

(51) Int. Cl.
| | |
|---|---|
| C12P 21/02 | (2006.01) |
| C12N 1/20 | (2006.01) |
| C07K 5/083 | (2006.01) |
| C07K 5/093 | (2006.01) |
| C12N 9/00 | (2006.01) |
| C12N 15/09 | (2006.01) |
| C12R 1/19 | (2006.01) |

(52) U.S. Cl.
CPC ............ *C12P 21/02* (2013.01); *C07K 5/0806* (2013.01); *C07K 5/0819* (2013.01); *C12N 1/205* (2021.05); *C12N 9/93* (2013.01); *C12N 15/09* (2013.01); *C12R 2001/19* (2021.05); *C12Y 603/02002* (2013.01); *C12Y 603/02003* (2013.01)

(58) Field of Classification Search
None
See application file for complete search history.

(56) References Cited

U.S. PATENT DOCUMENTS

| | | | | |
|---|---|---|---|---|
| 8,586,326 | B2 * | 11/2013 | El-Gewely | C07K 1/1136 435/69.1 |
| 9,580,696 | B2 * | 2/2017 | Nozaki | C12N 9/104 |
| 9,677,106 | B2 * | 6/2017 | Nozaki | C07K 5/0819 |
| 10,113,161 | B2 * | 10/2018 | Sasahara | C12Y 603/02002 |
| 10,508,295 | B2 * | 12/2019 | Tsuji | C12P 21/02 |
| 2010/0105864 | A1 | 4/2010 | Yoneda et al. | |
| 2010/0120698 | A1 | 5/2010 | Nagasaki et al. | |
| 2010/0183792 | A1 | 7/2010 | Nagasaki et al. | |
| 2011/0046046 | A1 | 2/2011 | Hara et al. | |
| 2011/0071075 | A1 | 3/2011 | Takeuchi et al. | |
| 2014/0212920 | A1 | 7/2014 | Nozaki et al. | |
| 2016/0326510 | A1 | 11/2016 | Sasahara et al. | |
| 2019/0264191 | A1 * | 8/2019 | Sato | C12P 21/02 |

FOREIGN PATENT DOCUMENTS

| | | | |
|---|---|---|---|
| EP | 3 101 130 | A1 | 12/2016 |
| JP | 8-119916 | A | 5/1996 |
| JP | 2012-85637 | A | 5/2012 |
| JP | 2017-46673 | A | 3/2017 |
| WO | WO 2007/055388 | A2 | 5/2007 |
| WO | WO 2007/055393 | A1 | 5/2007 |
| WO | WO 2008/139945 | A1 | 11/2008 |
| WO | WO 2008/139946 | A1 | 11/2008 |
| WO | WO 2008/139947 | A1 | 11/2008 |
| WO | WO 2009/107660 | A1 | 9/2009 |
| WO | WO 2009/119554 | A1 | 10/2009 |
| WO | WO 2013/051685 | A1 | 4/2013 |
| WO | WO 2013/054447 | A1 | 4/2013 |
| WO | WO 2015/115612 | A1 | 8/2015 |

OTHER PUBLICATIONS

International Search Report dated Oct. 4, 2016 in PCT/JP2016/075896, 2 pages.
Lehmann, Christopher, et al., "YbdK is a Carboxylate-Amine Ligase with a ɣ-Glutamyl: Cysteine Ligase Activity: Crystal Structure and Enzymatic Assays", Proteins, 2004, vol. 56, pp. 376-383.
Database UniProt, Retrieved from the internet: URL: http://www.uniprot org/uniprot/A0A0A6VST0.fasta?version=6, Accession No. A0A0A6VST0, Jun. 24, 2015, 1 page.
Database UniProt, Retrieved from the internet: URL: http://www.uniprot.org/uniprot/B2GJI7.fasta?version=52, Accession No. B2GJI7, Jul. 22, 2015, 1 page.
Database UniProt, Retrieved from the internet: URL: http://www.uniprot.org/uniprot/C5CC09.fasta?version=38, Accession No. C5CC09, Jul. 22, 2015, 1 page.
Kelly, Brenda S., et al., "*Escherichia coli* ɣ-Glutamylcysteine Synthetase", The Journal of Biological Chemistry, vol. 277 No. 1, Jan. 4, 2002. pp. 50-58 with cover page.
Kino, K., et al., "Novel Substrate Specificity of Glutathione Synthesis Enzymes from *Streptococcus agalactiae* and Clostridium Acetobutylicum", Biochemical and Biophysical Research Communications, vol. 352, 2007, pp. 351-359.

(Continued)

*Primary Examiner* — Hope A Robinson

(74) *Attorney, Agent, or Firm* — Oblon, McClelland, Maier & Neustadt, L.L.P.

(57) ABSTRACT

A microorganism useful as an expression host for γ-Glu-Val synthetase and a method for producing γ-Glu-Val-Gly using γ-Glu-Val synthetase expressed in the microorganism are provided. By using γ-Glu-Val synthetase expressed in a bacterium, such as *Escherichia* bacteria, modified so that the activity of a protein encoded by a ybdK gene (YBDIQ is reduced as an expression host, γ-Glu-Val-Gly is produced (Yom Glu, Val, and Gly as raw materials.

14 Claims, No Drawings

Specification includes a Sequence Listing.

(56) References Cited

OTHER PUBLICATIONS

Kumagai, H., et al., "γ-Glutamylcysteine Synthetase from Proteus Mirabilis", Agric. Biol. Chem., vol. 46 No. 5, 1982, pp. 1301-1309.
Vitali, R.A., et al., "The Isolation of γ-L-Glutamyl Peptides from a Fermentation Broth", The Journal of Biological Chemistry, vol. 240 No. 6, Jun. 1965, pp. 2508-2511.
International Preliminary Report on Patentability and Written Opinion dated Mar. 15, 2018 in PCT/JP2016/075896 (submitting English translation only), 9 pages.
Extended European Search Report dated Feb. 5, 2019 in European Patent Application No. 16842030.5, 7 pages.

\* cited by examiner

SEQUENCE LISTING

```
<160> NUMBER OF SEQ ID NOS: 29

<210> SEQ ID NO 1
<211> LENGTH: 35
<212> TYPE: DNA
<213> ORGANISM: Artificial Sequence
<220> FEATURE:
<223> OTHER INFORMATION: primer

<400> SEQUENCE: 1
taaggaggaa tccatatgcc attacccgat tttca                          35

<210> SEQ ID NO 2
<211> LENGTH: 60
<212> TYPE: DNA
<213> ORGANISM: Artificial Sequence
<220> FEATURE:
<223> OTHER INFORMATION: primer

<400> SEQUENCE: 2
cttgcatgcc tgcagttaat gatgatgatg atgatggtca ccggcccaga tctcacaatg    60

<210> SEQ ID NO 3
```

```
<211> LENGTH: 25
<212> TYPE: DNA
<213> ORGANISM: Artificial Sequence
<220> FEATURE:
<223> OTHER INFORMATION: primer

<400> SEQUENCE: 3
tgcatctggg tttgcatccg ctgct                                          25

<210> SEQ ID NO 4
<211> LENGTH: 43
<212> TYPE: DNA
<213> ORGANISM: Artificial Sequence
<220> FEATURE:
<223> OTHER INFORMATION: primer

<400> SEQUENCE: 4
ataaaaaagc aggcttcacg ttattctcca gagattaagg ggc                      43

<210> SEQ ID NO 5
<211> LENGTH: 43
<212> TYPE: DNA
<213> ORGANISM: Artificial Sequence
<220> FEATURE:
<223> OTHER INFORMATION: primer

<400> SEQUENCE: 5
tttatactaa cttgagcggg ttagcggccc tcttcgtggg aag                      43

<210> SEQ ID NO 6
<211> LENGTH: 25
<212> TYPE: DNA
<213> ORGANISM: Artificial Sequence
<220> FEATURE:
<223> OTHER INFORMATION: primer

<400> SEQUENCE: 6
actctacatg gacgctttag ccagg                                          25

<210> SEQ ID NO 7
<211> LENGTH: 43
<212> TYPE: DNA
<213> ORGANISM: Artificial Sequence
<220> FEATURE:
<223> OTHER INFORMATION: primer

<400> SEQUENCE: 7
gccccttaat ctctggagaa taacgtgaag cctgcttttt tat                      43

<210> SEQ ID NO 8
<211> LENGTH: 43
<212> TYPE: DNA
<213> ORGANISM: Artificial Sequence
<220> FEATURE:
<223> OTHER INFORMATION: primer

<400> SEQUENCE: 8
cttcccacga agagggccgc taacccgctc aagttagtat aaa                      43

<210> SEQ ID NO 9
<211> LENGTH: 58
<212> TYPE: DNA
<213> ORGANISM: Artificial Sequence
<220> FEATURE:
<223> OTHER INFORMATION: primer

<400> SEQUENCE: 9
```

```
ttatgctaat taaaacgatt ttgacaggcg ggaggtcaat tgaagcctgc ttttttat          58

<210> SEQ ID NO 10
<211> LENGTH: 58
<212> TYPE: DNA
<213> ORGANISM: Artificial Sequence
<220> FEATURE:
<223> OTHER INFORMATION: primer

<400> SEQUENCE: 10
tgaaattttg gccactcacg agtggccttt ttcttttctg cgctcaagtt agtataaa         58

<210> SEQ ID NO 11
<211> LENGTH: 80
<212> TYPE: DNA
<213> ORGANISM: Artificial Sequence
<220> FEATURE:
<223> OTHER INFORMATION: primer

<400> SEQUENCE: 11
cttctatact gaatagaaaa cgccaacata agagaaacct tgaagcctgc ttttttatac      60
taagttggca ttataaaaaa                                                  80

<210> SEQ ID NO 12
<211> LENGTH: 80
<212> TYPE: DNA
<213> ORGANISM: Artificial Sequence
<220> FEATURE:
<223> OTHER INFORMATION: primer

<400> SEQUENCE: 12
accattgtca gggatattct tctgtaaggc aattcccggc cgctcaagtt agtataaaaa      60
agctgaacga gaaacgtaaa                                                  80

<210> SEQ ID NO 13
<211> LENGTH: 35
<212> TYPE: DNA
<213> ORGANISM: Artificial Sequence
<220> FEATURE:
<223> OTHER INFORMATION: primer

<400> SEQUENCE: 13
aaggaggaat ccatatggaa atctcgtttg cccgc                                 35

<210> SEQ ID NO 14
<211> LENGTH: 41
<212> TYPE: DNA
<213> ORGANISM: Artificial Sequence
<220> FEATURE:
<223> OTHER INFORMATION: primer

<400> SEQUENCE: 14
ccaagcttgc atgcctgcag ttagtcgttt tcgcgagtac g                          41

<210> SEQ ID NO 15
<211> LENGTH: 1119
<212> TYPE: DNA
<213> ORGANISM: Escherichia coli

<400> SEQUENCE: 15
atgccattac ccgatttttca tgtttctgaa ccttttaccc tcggtattga actggaaatg     60
caggtggtta atccgccggg ctatgactta agccaggact cttcaatgct gattgacgcg    120
```

```
gttaaaaata agatcacggc cggagaggta aagcacgata tcaccgaaag tatgctggag      180
ctggcgacgg atgtttgccg tgatatcaac caggctgccg ggcagttttc agcgatgcag      240
aaagtcgtat tgcaggcagc cacagaccat catctggaaa tttgcggcgg tggcacgcac      300
ccgtttcaga aatggcagcg tcaggaggta tgcgataacg aacgctatca acgcacgctg      360
gaaaactttg gttatctcat tcagcaggcg accgtttttg gtcagcatgt ccatgttggc      420
tgcgccagtg gcgatgacgc catttatttg ctgcacggct tgtcacgatt tgtgccgcac      480
tttatcgccc tttccgccgc gtcgccatat atgcagggaa cggatacgcg ttttgcctcc      540
tcacgaccga atatttttc cgcctttcct gataatggcc cgatgccgtg ggtcagtaac      600
tggcaacaat ttgaagccct gtttcgctgt ctgagttaca ccacgatgat cgacagcatt      660
aaagatctgc actgggatat cgccccagt cctcatttg gcacggtgga ggttcgggtg      720
atggataccc cgttaaccct tagccacgca gtaaatatgg cgggattaat tcaggctacc      780
gcccactggt tactgacgga acgcccgttt aaacatcagg aaaaagatta cctgctgtat      840
aaattcaacc gtttccaggc ctgtcgctat gggcttgaag gcgtcatcac cgatccgcac      900
actggagatc gtcgaccgct aacggaagat accttgcgat tgctggaaaa aatcgcccct      960
tccgcacata aaattggtgc atcgagcgcg attgaggccc tgcatcgcca ggtcgtcagc     1020
ggtctgaatg aagcgcagct aatgcgcgat ttcgtcgccg atggcggctc gctgattggg     1080
ctggtgaaaa agcattgtga gatctgggcc ggtgactaa                            1119
```

<210> SEQ ID NO 16
<211> LENGTH: 372
<212> TYPE: PRT
<213> ORGANISM: Escherichia coli

<400> SEQUENCE: 16

```
Met Pro Leu Pro Asp Phe His Val Ser Glu Pro Phe Thr Leu Gly Ile
1               5                   10                  15

Glu Leu Glu Met Gln Val Val Asn Pro Pro Gly Tyr Asp Leu Ser Gln
            20                  25                  30

Asp Ser Ser Met Leu Ile Asp Ala Val Lys Asn Lys Ile Thr Ala Gly
        35                  40                  45

Glu Val Lys His Asp Ile Thr Glu Ser Met Leu Glu Leu Ala Thr Asp
    50                  55                  60

Val Cys Arg Asp Ile Asn Gln Ala Ala Gly Gln Phe Ser Ala Met Gln
65                  70                  75                  80

Lys Val Val Leu Gln Ala Ala Thr Asp His His Leu Glu Ile Cys Gly
                85                  90                  95

Gly Gly Thr His Pro Phe Gln Lys Trp Gln Arg Gln Glu Val Cys Asp
            100                 105                 110

Asn Glu Arg Tyr Gln Arg Thr Leu Glu Asn Phe Gly Tyr Leu Ile Gln
        115                 120                 125

Gln Ala Thr Val Phe Gly Gln His Val His Val Gly Cys Ala Ser Gly
    130                 135                 140

Asp Asp Ala Ile Tyr Leu Leu His Gly Leu Ser Arg Phe Val Pro His
145                 150                 155                 160

Phe Ile Ala Leu Ser Ala Ala Ser Pro Tyr Met Gln Gly Thr Asp Thr
                165                 170                 175

Arg Phe Ala Ser Ser Arg Pro Asn Ile Phe Ser Ala Phe Pro Asp Asn
            180                 185                 190

Gly Pro Met Pro Trp Val Ser Asn Trp Gln Gln Phe Glu Ala Leu Phe
```

```
            195                 200                 205
Arg Cys Leu Ser Tyr Thr Thr Met Ile Asp Ser Ile Lys Asp Leu His
    210                 215                 220

Trp Asp Ile Arg Pro Ser Pro His Phe Gly Thr Val Glu Val Arg Val
225                 230                 235                 240

Met Asp Thr Pro Leu Thr Leu Ser His Ala Val Asn Met Ala Gly Leu
                245                 250                 255

Ile Gln Ala Thr Ala His Trp Leu Leu Thr Glu Arg Pro Phe Lys His
            260                 265                 270

Gln Glu Lys Asp Tyr Leu Leu Tyr Lys Phe Asn Arg Phe Gln Ala Cys
        275                 280                 285

Arg Tyr Gly Leu Glu Gly Val Ile Thr Asp Pro His Thr Gly Asp Arg
    290                 295                 300

Arg Pro Leu Thr Glu Asp Thr Leu Arg Leu Leu Glu Lys Ile Ala Pro
305                 310                 315                 320

Ser Ala His Lys Ile Gly Ala Ser Ser Ala Ile Glu Ala Leu His Arg
                325                 330                 335

Gln Val Val Ser Gly Leu Asn Glu Ala Gln Leu Met Arg Asp Phe Val
            340                 345                 350

Ala Asp Gly Gly Ser Leu Ile Gly Leu Val Lys Lys His Cys Glu Ile
        355                 360                 365

Trp Ala Gly Asp
    370

<210> SEQ ID NO 17
<211> LENGTH: 1146
<212> TYPE: DNA
<213> ORGANISM: Kocuria rosea

<400> SEQUENCE: 17
gtggagatct cgttcgcccg ctcccaccag tcgacgctgg cgtcgagtg  ggagatcgcc       60
ctcgtggacg gcaccaccgg ggatctcgtc ccccggggcc gggagacgtt cgaggccgtc      120
ctggacgccc accccgcctg ggcacggac  ggcgaccacc cgcacctgac cggggagttc      180
ctgctcaaca ccgtcgagct ggtcaccggg gtgtgccggg acgtcgccca ctccaccgag      240
cagctgtcca ccatgctgga cgagatccgc aaggtcaccg acccgcaggg cctcgaggtc      300
ttcgccgccg gcaccacccc gttcgcccgc tggcaggacc agcaggtcac cgacaagcag      360
cgctaccaca gctcgtgga  ccgcacccag tactggggcc ggcagatggt catctacggg      420
gtgcacgtgc acgtgggcct cgactcccgg gcgaaggcgc tgcccgtgct ggacgggctg      480
ctgacctact acccgcacct gctggcgctg tccgcgaact cgcccttctg gcgggcgag      540
gacaccggct atgcgtccca cgctccatg  atcttccagc agctgtccac ggcggggctg      600
ccgtaccact cccgtcctg  ggacgcgtac gagcagtgca tcacggacat gatcgccacc      660
ggcatcatcg aggagatgag cgaggcccgc tgggacgtgc gccccgtgcc ccggctgggc      720
accgacgagg tgcgcttctg cgacgggctc tcgaccctgt gggaggtcgg ggcgctcacg      780
gcgctcaccc agtgcctcgc ggagtccatc tcccgggacg tggaggcggg ccggcccccc      840
gcccgcctga agcgtggca  catccaggag aacaagtggc gcgccgcccg ctacggcctc      900
gacgccgagg tcatcaccga cccgcgcaac gtcgagcggg acctgcgcac ggacctgacc      960
gcgctgctcg accggctgga gcccgtggcc gcgcagctgg gctgctcccg cgagctcgcc     1020
gacgtggagc ggatcctgga gcagggcgcc ggctaccagc gccagcgcgc ggtcgcccgg     1080
```

```
gcccacgacg gggacctgca cgccgtcgcc ctcgacatcg tccgccgcac ccgggagaac    1140
gactga                                                              1146
```

<210> SEQ ID NO 18
<211> LENGTH: 381
<212> TYPE: PRT
<213> ORGANISM: Kocuria rosea

<400> SEQUENCE: 18

```
Met Glu Ile Ser Phe Ala Arg Ser His Gln Ser Thr Leu Gly Val Glu
 1               5                  10                  15

Trp Glu Ile Ala Leu Val Asp Gly Thr Thr Gly Asp Leu Val Pro Arg
            20                  25                  30

Gly Arg Glu Thr Phe Glu Ala Val Leu Asp Ala His Pro Ala Trp Gly
        35                  40                  45

Thr Asp Gly Asp His Pro His Leu Thr Gly Glu Phe Leu Leu Asn Thr
    50                  55                  60

Val Glu Leu Val Thr Gly Val Cys Arg Asp Val Ala His Ser Thr Glu
65                  70                  75                  80

Gln Leu Ser Thr Met Leu Asp Glu Ile Arg Lys Val Thr Asp Pro Gln
                85                  90                  95

Gly Leu Glu Val Phe Ala Ala Gly Thr His Pro Phe Ala Arg Trp Gln
            100                 105                 110

Asp Gln Gln Val Thr Asp Lys Gln Arg Tyr His Lys Leu Val Asp Arg
        115                 120                 125

Thr Gln Tyr Trp Gly Arg Gln Met Val Ile Tyr Gly Val His Val His
    130                 135                 140

Val Gly Leu Asp Ser Arg Ala Lys Ala Leu Pro Val Leu Asp Gly Leu
145                 150                 155                 160

Leu Thr Tyr Tyr Pro His Leu Leu Ala Leu Ser Ala Asn Ser Pro Phe
                165                 170                 175

Trp Ala Gly Glu Asp Thr Gly Tyr Ala Ser Gln Arg Ser Met Ile Phe
            180                 185                 190

Gln Gln Leu Ser Thr Ala Gly Leu Pro Tyr His Phe Pro Ser Trp Asp
        195                 200                 205

Ala Tyr Glu Gln Cys Ile Thr Asp Met Ile Ala Thr Gly Ile Ile Glu
    210                 215                 220

Glu Met Ser Glu Ala Arg Trp Asp Val Arg Pro Val Pro Arg Leu Gly
225                 230                 235                 240

Thr Asp Glu Val Arg Phe Cys Asp Gly Leu Ser Thr Leu Trp Glu Val
                245                 250                 255

Gly Ala Leu Thr Ala Leu Thr Gln Cys Leu Ala Glu Ser Ile Ser Arg
            260                 265                 270

Asp Val Glu Ala Gly Arg Pro Pro Ala Arg Leu Lys Pro Trp His Ile
        275                 280                 285

Gln Glu Asn Lys Trp Arg Ala Ala Arg Tyr Gly Leu Asp Ala Glu Val
    290                 295                 300

Ile Thr Asp Pro Arg Asn Val Glu Arg Asp Leu Arg Thr Asp Leu Thr
305                 310                 315                 320

Ala Leu Leu Asp Arg Leu Glu Pro Val Ala Ala Gln Leu Gly Cys Ser
                325                 330                 335

Arg Glu Leu Ala Asp Val Glu Arg Ile Leu Glu Gln Gly Ala Gly Tyr
            340                 345                 350

Gln Arg Gln Arg Ala Val Ala Arg Ala His Asp Gly Asp Leu His Ala
```

```
             355                 360                 365
Val Ala Leu Asp Ile Val Arg Arg Thr Arg Glu Asn Asp
    370                 375                 380
```

<210> SEQ ID NO 19
<211> LENGTH: 1182
<212> TYPE: DNA
<213> ORGANISM: Kocuria rhizophila

<400> SEQUENCE: 19

```
atgccgttcc cggcgcaccc acgagaggac cacgccgtgc acattgattt cgagacctcc      60
gagaactcca ccctgggtgt ggaatgggag gtcgcgctcg tggaccgcga atccggtgag     120
ctcgccccgc gcgcccagga ggtcctggag gccgtggtgg gcgagtaccc cgagctcggg     180
gaggagggcg accacccgca ggtcacgggc gagttcctgc agaacaccgt ggaaatggtc     240
acgggcgtgt gcagcgccgt tcccgaggcg gtggagcacc tcgcgcagac ccaggaccgg     300
atccggaaga tcaccgaccc ccgctccctg gaaatcttcg ccgcgggcac ccacccgttc     360
tcggactgga ccgagcagcc cgtggtggac gcggagcgct actacaaggt cctggaccgg     420
gcgcagtact ggggccggca gatggtgatc ttcggcatgc acgtgcacgt gggcatcgac     480
caccgggaca aggcgctgcc cgtgctcgac gggctcatga actactaccc ccacctgctg     540
gcgctgtccg cgaactcccc ctactggtgc ggccacgaca ccggctacgc ctcccaccgg     600
gcgctgatct tccagcagct ctccaccgcg gggctgccct ccacttcga ctcctggagc      660
gagtacgagg cctacgtctc ggacctcatg gagaccggcg tgatcgagga gatctccgag     720
aaccgctggg acatccgccc cgtgccgcgc ttcggcaccg tggagatgcg cgtgtgcgac     780
gggccctcca acctcgggga gatcggcgcc ctggccgcgc tgacgcagtg cctcgtggag     840
tccttctccc gcaccctgga cgaggggcgc agcattgcgg tgatgccccc gtggcaccac     900
caggagaaca gtggcgggc cgcccgctac gggctggacg ccgtggtgat ccggacgcc      960
cagaaccacg agcgccccgt ggcggaggac ctcaccgagg tgctcaaccg gctggagccc    1020
ctcgccgccg aactcggctg cgctgacgag ctgggctacg tggagaccat gatgacgggc    1080
gagaccggct accagcgcca gcggcggatc gcggaggcca acggcgggga cctgcgcgcc    1140
gtggtgcggg acatcgtggc gcagaaccgc gagatccgct ga                       1182
```

<210> SEQ ID NO 20
<211> LENGTH: 393
<212> TYPE: PRT
<213> ORGANISM: Kocuria rhizophila

<400> SEQUENCE: 20

```
Met Pro Phe Pro Ala His Pro Arg Glu Asp His Ala Val His Ile Asp
1               5                   10                  15

Phe Glu Thr Ser Glu Asn Ser Thr Leu Gly Val Glu Trp Glu Val Ala
                20                  25                  30

Leu Val Asp Arg Glu Ser Gly Glu Leu Ala Pro Arg Ala Gln Glu Val
            35                  40                  45

Leu Glu Ala Val Val Gly Glu Tyr Pro Glu Leu Gly Glu Glu Gly Asp
        50                  55                  60

His Pro Gln Val Thr Gly Glu Phe Leu Gln Asn Thr Val Glu Met Val
65                  70                  75                  80

Thr Gly Val Cys Ser Ala Val Pro Glu Ala Val Glu His Leu Ala Gln
                85                  90                  95
```

```
Thr Gln Asp Arg Ile Arg Lys Ile Thr Asp Pro Arg Ser Leu Glu Ile
            100                 105                 110

Phe Ala Ala Gly Thr His Pro Phe Ser Asp Trp Thr Glu Gln Pro Val
        115                 120                 125

Val Asp Ala Glu Arg Tyr Tyr Lys Val Leu Asp Arg Ala Gln Tyr Trp
    130                 135                 140

Gly Arg Gln Met Val Ile Phe Gly Met His Val His Val Gly Ile Asp
145                 150                 155                 160

His Arg Asp Lys Ala Leu Pro Val Leu Asp Gly Leu Met Asn Tyr Tyr
                165                 170                 175

Pro His Leu Leu Ala Leu Ser Ala Asn Ser Pro Tyr Trp Cys Gly His
            180                 185                 190

Asp Thr Gly Tyr Ala Ser His Arg Ala Leu Ile Phe Gln Gln Leu Ser
        195                 200                 205

Thr Ala Gly Leu Pro Phe His Phe Asp Ser Trp Ser Glu Tyr Glu Ala
    210                 215                 220

Tyr Val Ser Asp Leu Met Glu Thr Gly Val Ile Glu Glu Ile Ser Glu
225                 230                 235                 240

Asn Arg Trp Asp Ile Arg Pro Val Pro Arg Phe Gly Thr Val Glu Met
                245                 250                 255

Arg Val Cys Asp Gly Pro Ser Asn Leu Arg Glu Ile Gly Ala Leu Ala
            260                 265                 270

Ala Leu Thr Gln Cys Leu Val Glu Ser Phe Ser Arg Thr Leu Asp Glu
        275                 280                 285

Gly Arg Ser Ile Ala Val Met Pro Pro Trp His His Gln Glu Asn Lys
    290                 295                 300

Trp Arg Ala Ala Arg Tyr Gly Leu Asp Ala Val Val Ile Arg Asp Ala
305                 310                 315                 320

Gln Asn His Glu Arg Pro Val Ala Glu Asp Leu Thr Glu Val Leu Asn
                325                 330                 335

Arg Leu Glu Pro Leu Ala Ala Glu Leu Gly Cys Ala Asp Glu Leu Gly
            340                 345                 350

Tyr Val Glu Thr Met Met Thr Gly Glu Thr Gly Tyr Gln Arg Gln Arg
        355                 360                 365

Arg Ile Ala Glu Ala Asn Gly Gly Asp Leu Arg Ala Val Val Arg Asp
    370                 375                 380

Ile Val Ala Gln Asn Arg Glu Ile Arg
385                 390

<210> SEQ ID NO 21
<211> LENGTH: 1197
<212> TYPE: DNA
<213> ORGANISM: Micrococcus luteus

<400> SEQUENCE: 21
atgactctgc ccttcgccga ctccgcgcag tccactctcg gaatcgagtg ggagctcgcg      60
ctcgtggacg ccgtgtccgg cgagctgcgc tccgaggccc agacctgct gcgcgccctg      120 catgtggccg agggcctggc cgacgacgac gtgaacccgc acatgaccag cgagctcctg      180
cagaacacgg tggagctcgt cacgggcgtg cacgagcgct cgacgccgc gacggcggac      240 ctcggccgga tcgccgcgcg cgtggccgac gccgcggcgg cgcggggcat ctccctgttc      300
tgccagggca cgcaccccgtt cgcggacgcg atcgcgcagc cctcgacacc cagtgagcgc      360
tacgaccgca tgctggatct cacccagtac tggggtcggc agctgctgat cttcggcgtg      420
```

-continued

```
cacgtgcacg tgggcctgga cgacgtctcc aaggccatgc cggtggtgaa cggcctggtc      480
aaccgcgtgc cgcacctgct cgcactctcg gcctcctccc ccttctgggc gggcacggac      540
acgggctacc agtcccagcg caccctcctg ttccagcagc tgcccacggc cggcctgccg      600
ttccagttcc aggagtggga ggacttcgag cgctgcgtgg cccagatgga gcaggtgggc      660
atgatcgcgg acgtcaccga gtgccgctgg gacgtgcggg ccgtgccccg cctgggcacg      720
gtggagatgc gcgcgtgtga cggcctggcc acgctcgagg agatcgccgc cgtgaccgcc      780
tacacgcagt gcctcgtgga cgatctgtcc gcgagcctgg agcgcggtga cacggtcgag      840
gtcctgccgc cgtggcacgc gcaggagaac aagtggcgcg ccgcccggta cggcatggac      900
gccaccgtga tcgtggacgc ccggggcacc caggttccgc tggcggagca cctgccggcg      960
gagatcgagc gactgacccc ggtcgccgag cggctgggct gcgaggcaga gctcgccggc     1020
gtccaggcga tgatcgacga cggcggcgcc gcgcgtcagc gtcgcgtgga ggcacaggcc     1080
ctggccggcc cgccggccga gggcgaggac gcggacgacg cggtggcccc gttgcgcgcg     1140
gtcgtgctgg acgccgccgc ccgcacccgc gcgtcgctgg acggccgcac cggctga       1197
```

<210> SEQ ID NO 22
<211> LENGTH: 398
<212> TYPE: PRT
<213> ORGANISM: Micrococcus luteus

<400> SEQUENCE: 22

```
Met Thr Leu Pro Phe Ala Asp Ser Ala Gln Ser Thr Leu Gly Ile Glu
1               5                   10                  15

Trp Glu Leu Ala Leu Val Asp Ala Val Ser Gly Glu Leu Arg Ser Glu
            20                  25                  30

Ala Pro Asp Leu Leu Arg Ala Leu His Val Ala Glu Gly Leu Ala Asp
        35                  40                  45

Asp Asp Val Asn Pro His Met Thr Ser Glu Leu Leu Gln Asn Thr Val
    50                  55                  60

Glu Leu Val Thr Gly Val His Glu Arg Val Asp Ala Ala Thr Ala Asp
65                  70                  75                  80

Leu Gly Arg Ile Ala Ala Arg Val Ala Asp Ala Ala Ala Arg Gly
                85                  90                  95

Ile Ser Leu Phe Cys Gln Gly Thr His Pro Phe Ala Asp Ala Ile Ala
            100                 105                 110

Gln Pro Ser Thr Pro Ser Glu Arg Tyr Asp Arg Met Leu Asp Leu Thr
        115                 120                 125

Gln Tyr Trp Gly Arg Gln Leu Leu Ile Phe Gly Val His Val His Val
    130                 135                 140

Gly Leu Asp Asp Val Ser Lys Ala Met Pro Val Val Asn Gly Leu Val
145                 150                 155                 160

Asn Arg Val Pro His Leu Leu Ala Leu Ser Ala Ser Pro Phe Trp
                165                 170                 175

Ala Gly Thr Asp Thr Gly Tyr Gln Ser Gln Arg Thr Leu Leu Phe Gln
            180                 185                 190

Gln Leu Pro Thr Ala Gly Leu Pro Phe Gln Phe Gln Glu Trp Glu Asp
        195                 200                 205

Phe Glu Arg Cys Val Ala Gln Met Glu Gln Val Gly Met Ile Ala Asp
    210                 215                 220

Val Thr Glu Cys Arg Trp Asp Val Arg Ala Val Pro Arg Leu Gly Thr
225                 230                 235                 240
```

```
Val Glu Met Arg Ala Cys Asp Gly Leu Ala Thr Leu Glu Glu Ile Ala
            245                 250                 255

Ala Val Thr Ala Tyr Thr Gln Cys Leu Val Asp Asp Leu Ser Ala Ser
        260                 265                 270

Leu Glu Arg Gly Glu Thr Val Glu Val Leu Pro Pro Trp His Ala Gln
    275                 280                 285

Glu Asn Lys Trp Arg Ala Ala Arg Tyr Gly Met Asp Ala Thr Val Ile
290                 295                 300

Val Asp Ala Arg Gly Thr Gln Val Pro Leu Ala Glu His Leu Pro Ala
305                 310                 315                 320

Glu Ile Glu Arg Leu Thr Pro Val Ala Glu Arg Leu Gly Cys Glu Ala
                325                 330                 335

Glu Leu Ala Gly Val Gln Ala Met Ile Asp Asp Gly Gly Ala Ala Arg
            340                 345                 350

Gln Arg Arg Val Glu Ala Gln Ala Leu Ala Gly Pro Pro Ala Glu Gly
        355                 360                 365

Glu Asp Ala Asp Asp Ala Val Ala Pro Leu Arg Ala Val Val Leu Asp
    370                 375                 380

Ala Ala Ala Arg Thr Arg Ala Ser Leu Asp Gly Arg Thr Gly
385                 390                 395

<210> SEQ ID NO 23
<211> LENGTH: 1557
<212> TYPE: DNA
<213> ORGANISM: Escherichia coli

<400> SEQUENCE: 23
ttgatcccgg acgtatcaca ggcgctggcc tggctggaaa acatcctca ggcgttaaag      60
gggatacagc gtgggctgga gcgcgaaact ttgcgtgtta atgctgatgg cacactggca    120
acaacaggtc atcctgaagc attaggttcc gcactgacgc acaaatggat tactaccgat    180
tttgcggaag cattgctgga attcattaca ccagtggatg tgatattga acatatgctg    240
acctttatgc gcgatctgca tcgttatacg gcgcgcaata tgggcgatga gcggatgtgg    300
ccgttaagta tgccatgcta catcgcagaa ggtcaggaca tcgaactggc acagtacggc    360
acttctaaca ccggacgctt taaaacgctg tatcgtgaag ggctgaaaaa tcgctacggc    420
gcgctgatgc aaaccatttc cggcgtgcac tacaatttct cttttgccaat ggcattctgg    480
caagcgaagt gcggtgatat ctcgggcgct gatgccaaag agaaaatttc tgcgggctat    540
ttccgcgtta tccgcaatta ctatcgtttc ggttgggtca ttcctatct gtttggtgca    600
tctccggcga tttgttcttc tttcctgcaa ggaaaaccaa cgtcgctgcc gtttgagaaa    660
accgagtgcg gtatgtatta cctgccgtat gcgacctctc ttcgtttgag cgatctcggc    720
tataccaata aatcgcaaag caatcttggt attaccttca acgatcttta cgagtacgta    780
gcgggcctta acaggcaat caaaacgcca tcggaagagt acgcgaagat tggtattgag    840
aaagacggta agaggctgca aatcaacagc aacgtgttgc agattgaaaa cgaactgtac    900
gcgccgattc gtccaaaacg cgttacccgc agcggcgagt cgccttctga tgcgctgtta    960
cgtggcggca ttgaatatat tgaagtgcgt tcgctggaca tcaacccgtt ctcgccgatt   1020
ggtgtagatg aacagcaggt gcgattcctc gacctgttta tggtctggtg tgcgctggct   1080
gatgcaccgg aaatgagcag tagcgaactt gcctgtacac gcgttaactg gaaccgggtg   1140
atcctcgaag tcgcaaaacc gggtctgacg ctgggtatcg gctgcgaaac cgcacagttc   1200
ccgttaccgc aggtgggtaa agatctgttc cgcgatctga aacgcgtcgc gcaaacgctg   1260
```

```
gatagtatta acggcggcga agcgtatcag aaagtgtgtg atgaactggt tgcctgcttc    1320
gataatcccg atctgacttt ctctgcccgt atcttaaggt ctatgattga tactggtatt    1380
ggcggaacag gcaaagcatt tgcagaagcc taccgtaatc tgctgcgtga agagccgctg    1440
gaaattctgc gcgaagagga ttttgtagcc gagcgcgagg cgtctgaacg ccgtcagcag    1500
gaaatggaag ccgctgatac cgaaccgttt gcggtgtggc tggaaaaaca cgcctga       1557
```

<210> SEQ ID NO 24
<211> LENGTH: 518
<212> TYPE: PRT
<213> ORGANISM: Escherichia coli

<400> SEQUENCE: 24

```
Met Ile Pro Asp Val Ser Gln Ala Leu Ala Trp Leu Glu Lys His Pro
1               5                   10                  15

Gln Ala Leu Lys Gly Ile Gln Arg Gly Leu Glu Arg Glu Thr Leu Arg
            20                  25                  30

Val Asn Ala Asp Gly Thr Leu Ala Thr Thr Gly His Pro Glu Ala Leu
        35                  40                  45

Gly Ser Ala Leu Thr His Lys Trp Ile Thr Thr Asp Phe Ala Glu Ala
    50                  55                  60

Leu Leu Glu Phe Ile Thr Pro Val Asp Gly Asp Ile Glu His Met Leu
65                  70                  75                  80

Thr Phe Met Arg Asp Leu His Arg Tyr Thr Ala Arg Asn Met Gly Asp
                85                  90                  95

Glu Arg Met Trp Pro Leu Ser Met Pro Cys Tyr Ile Ala Glu Gly Gln
            100                 105                 110

Asp Ile Glu Leu Ala Gln Tyr Gly Thr Ser Asn Thr Gly Arg Phe Lys
        115                 120                 125

Thr Leu Tyr Arg Glu Gly Leu Lys Asn Arg Tyr Gly Ala Leu Met Gln
    130                 135                 140

Thr Ile Ser Gly Val His Tyr Asn Phe Ser Leu Pro Met Ala Phe Trp
145                 150                 155                 160

Gln Ala Lys Cys Gly Asp Ile Ser Gly Ala Asp Ala Lys Glu Lys Ile
                165                 170                 175

Ser Ala Gly Tyr Phe Arg Val Ile Arg Asn Tyr Tyr Arg Phe Gly Trp
            180                 185                 190

Val Ile Pro Tyr Leu Phe Gly Ala Ser Pro Ala Ile Cys Ser Ser Phe
        195                 200                 205

Leu Gln Gly Lys Pro Thr Ser Leu Pro Phe Glu Lys Thr Glu Cys Gly
    210                 215                 220

Met Tyr Tyr Leu Pro Tyr Ala Thr Ser Leu Arg Leu Ser Asp Leu Gly
225                 230                 235                 240

Tyr Thr Asn Lys Ser Gln Ser Asn Leu Gly Ile Thr Phe Asn Asp Leu
                245                 250                 255

Tyr Glu Tyr Val Ala Gly Leu Lys Gln Ala Ile Lys Thr Pro Ser Glu
            260                 265                 270

Glu Tyr Ala Lys Ile Gly Ile Glu Lys Asp Gly Lys Arg Leu Gln Ile
        275                 280                 285

Asn Ser Asn Val Leu Gln Ile Glu Asn Glu Leu Tyr Ala Pro Ile Arg
    290                 295                 300

Pro Lys Arg Val Thr Arg Ser Gly Glu Ser Pro Ser Asp Ala Leu Leu
305                 310                 315                 320
```

```
Arg Gly Gly Ile Glu Tyr Ile Glu Val Arg Ser Leu Asp Ile Asn Pro
            325                 330                 335

Phe Ser Pro Ile Gly Val Asp Glu Gln Gln Val Arg Phe Leu Asp Leu
        340                 345                 350

Phe Met Val Trp Cys Ala Leu Ala Asp Ala Pro Glu Met Ser Ser Ser
        355                 360                 365

Glu Leu Ala Cys Thr Arg Val Asn Trp Asn Arg Val Ile Leu Glu Gly
        370                 375                 380

Arg Lys Pro Gly Leu Thr Leu Gly Ile Gly Cys Glu Thr Ala Gln Phe
385                 390                 395                 400

Pro Leu Pro Gln Val Gly Lys Asp Leu Phe Arg Asp Leu Lys Arg Val
                405                 410                 415

Ala Gln Thr Leu Asp Ser Ile Asn Gly Gly Glu Ala Tyr Gln Lys Val
            420                 425                 430

Cys Asp Glu Leu Val Ala Cys Phe Asp Asn Pro Asp Leu Thr Phe Ser
        435                 440                 445

Ala Arg Ile Leu Arg Ser Met Ile Asp Thr Gly Ile Gly Gly Thr Gly
        450                 455                 460

Lys Ala Phe Ala Glu Ala Tyr Arg Asn Leu Leu Arg Glu Glu Pro Leu
465                 470                 475                 480

Glu Ile Leu Arg Glu Glu Asp Phe Val Ala Glu Arg Glu Ala Ser Glu
                485                 490                 495

Arg Arg Gln Gln Glu Met Glu Ala Ala Asp Thr Glu Pro Phe Ala Val
            500                 505                 510

Trp Leu Glu Lys His Ala
        515

<210> SEQ ID NO 25
<211> LENGTH: 1743
<212> TYPE: DNA
<213> ORGANISM: Escherichia coli

<400> SEQUENCE: 25
atgataaaac cgacgttttt acgccgggtg gccattgctg ctctgctctc aggaagttgt      60
tttagcgccg ccgccgcgcc tcctgcgccc cccgtctcgt atggtgtgga ggaagatgtc     120
ttccacccgg tacgcgcgaa acagggaatg gtagcgtctg tggacgccac tgccactcag     180 gtggggtgg atattctcaa ggagggcggg aatgccgttg atgccgccgt ggcggtgggc     240
tacgcgctgg cggtaacgca tccgcaggca gggaatctgg cggtggtgg ttttatgtta     300 atccgctcga aaaatggcaa taccacggct atcgatttcc gcgaaatggc acccgccaaa     360
gcgacccgcg atatgttcct cgatgatcag ggcaacccgg acagcaaaaa atcactcact     420
tcgcatctgc cttccggcac accgggtacg gtagcaggtt tctcgctggc gctggataaa     480
tacggcacca tgccgctgaa caaagtcgtg cagcccgcgt ttaaactggc acgcgatggt     540
tttatcgtta acgacgcgct ggctgacgat ctcaaaacct acggtagcga agtgttgccg     600
aatcacgaaa acagtaaagc tatcttctgg aaagagggcg agccgctgaa aagggcgac     660 acgctggtgc aggcgaacct ggcaaagagc ctggagatga ttgctgaaaa cggcccggac     720
gaattctata aggcacgat tgcggaacag atcgcccagg atgcagaa aaacggtggc     780 ttgatcacta agaagatttt agcagcctat aaagcggtcg aacgcactcc gataagcggc     840
gattatcgcg gtatcaggt ttactccatg ccaccgccat cctccggcgg gatccatatc     900
gtacaaatcc tcaatattct ggaaaacttc gatatgaaga aatacggctt tggcagcgcc     960
```

-continued

```
gatgcgatgc aaatcatggc agaagcggag aaatacgcct acgccgaccg ctcggaatat    1020
cttggcgacc cggattttgt caaagtaccg tggcaggcgc tgaccaataa agcctatgcc    1080
aaatctattg ccgatcaaat tgatatcaat aaagcgaagc catccagcga aattcgcccc    1140
ggcaagcttg cgccttatga gagtaatcaa actacccatt actcagtggt ggataaagat    1200
ggtaacgcgg tggcggtgac ctatacgctg aacaccacct tcggtacggg cattgtcgcg    1260
ggcgagagcg gtattctgct taataaccag atggatgatt tctccgccaa accgggcgta    1320
ccgaacgttt acgggctggt gggcggtgat gccaacgccg tcgggccgaa caaacgcccg    1380
ctgtcgtcga tgtcgccgac cattgtggtg aaagacggta aacctggct ggttaccggt    1440 agcccaggcg gtagccggat catcactaca gtgctgcaaa tggtggtgaa tagcatcgat    1500
tatggcttga acgtcgccga agcgaccaat gcgccgcgtt ccaccatca gtggttgccg    1560 gacgagctgc gtgtcgaaaa agggtttagc ccggatacgc tcaagctgct ggaagcaaaa    1620
ggtcagaaag tggcgctgaa agaggcgatg ggcagtacac aaagcattat ggttgggccg    1680
gacggtgagt tgtacggcgc atccgacccg cgctcggtgg atgatttaac ggcggggtac    1740
taa                                                                  1743
```

<210> SEQ ID NO 26
<211> LENGTH: 580
<212> TYPE: PRT
<213> ORGANISM: Escherichia coli

<400> SEQUENCE: 26

```
Met Ile Lys Pro Thr Phe Leu Arg Arg Val Ala Ile Ala Ala Leu Leu
1               5                   10                  15

Ser Gly Ser Cys Phe Ser Ala Ala Ala Pro Pro Ala Pro Pro Val
            20                  25                  30

Ser Tyr Gly Val Glu Glu Asp Val Phe His Pro Val Arg Ala Lys Gln
        35                  40                  45

Gly Met Val Ala Ser Val Asp Ala Thr Ala Thr Gln Val Gly Val Asp
    50                  55                  60

Ile Leu Lys Glu Gly Gly Asn Ala Val Asp Ala Val Ala Val Gly
65                  70                  75                  80

Tyr Ala Leu Ala Val Thr His Pro Gln Ala Gly Asn Leu Gly Gly Gly
                85                  90                  95

Gly Phe Met Leu Ile Arg Ser Lys Asn Gly Asn Thr Ala Ile Asp
            100                 105                 110

Phe Arg Glu Met Ala Pro Ala Lys Ala Thr Arg Asp Met Phe Leu Asp
        115                 120                 125

Asp Gln Gly Asn Pro Asp Ser Lys Lys Ser Leu Thr Ser His Leu Ala
    130                 135                 140

Ser Gly Thr Pro Gly Thr Val Ala Gly Phe Ser Leu Ala Leu Asp Lys
145                 150                 155                 160

Tyr Gly Thr Met Pro Leu Asn Lys Val Val Gln Pro Ala Phe Lys Leu
                165                 170                 175

Ala Arg Asp Gly Phe Ile Val Asn Asp Ala Leu Ala Asp Leu Lys
            180                 185                 190

Thr Tyr Gly Ser Glu Val Leu Pro Asn His Glu Asn Ser Lys Ala Ile
        195                 200                 205

Phe Trp Lys Glu Gly Glu Pro Leu Lys Lys Gly Asp Thr Leu Val Gln
    210                 215                 220

Ala Asn Leu Ala Lys Ser Leu Glu Met Ile Ala Glu Asn Gly Pro Asp
```

```
                    225                 230                 235                 240
        Glu Phe Tyr Lys Gly Thr Ile Ala Glu Gln Ile Ala Gln Glu Met Gln
                        245                 250                 255

Lys Asn Gly Gly Leu Ile Thr Lys Glu Asp Leu Ala Ala Tyr Lys Ala
                        260                 265                 270

Val Glu Arg Thr Pro Ile Ser Gly Asp Tyr Arg Gly Tyr Gln Val Tyr
                        275                 280                 285

Ser Met Pro Pro Pro Ser Ser Gly Gly Ile His Ile Val Gln Ile Leu
                290                 295                 300

Asn Ile Leu Glu Asn Phe Asp Met Lys Lys Tyr Gly Phe Gly Ser Ala
        305                 310                 315                 320

Asp Ala Met Gln Ile Met Ala Glu Ala Glu Lys Tyr Ala Tyr Ala Asp
                        325                 330                 335

Arg Ser Glu Tyr Leu Gly Asp Pro Asp Phe Val Lys Val Pro Trp Gln
                        340                 345                 350

Ala Leu Thr Asn Lys Ala Tyr Ala Lys Ser Ile Ala Asp Gln Ile Asp
                        355                 360                 365

Ile Asn Lys Ala Lys Pro Ser Ser Glu Ile Arg Pro Gly Lys Leu Ala
                370                 375                 380

Pro Tyr Glu Ser Asn Gln Thr Thr His Tyr Ser Val Val Asp Lys Asp
        385                 390                 395                 400

Gly Asn Ala Val Ala Val Thr Tyr Thr Leu Asn Thr Thr Phe Gly Thr
                        405                 410                 415

Gly Ile Val Ala Gly Glu Ser Gly Ile Leu Leu Asn Asn Gln Met Asp
                        420                 425                 430

Asp Phe Ser Ala Lys Pro Gly Val Pro Asn Val Tyr Gly Leu Val Gly
                        435                 440                 445

Gly Asp Ala Asn Ala Val Gly Pro Asn Lys Arg Pro Leu Ser Ser Met
                450                 455                 460

Ser Pro Thr Ile Val Val Lys Asp Gly Lys Thr Trp Leu Val Thr Gly
        465                 470                 475                 480

Ser Pro Gly Gly Ser Arg Ile Ile Thr Thr Val Leu Gln Met Val Val
                        485                 490                 495

Asn Ser Ile Asp Tyr Gly Leu Asn Val Ala Glu Ala Thr Asn Ala Pro
                        500                 505                 510

Arg Phe His His Gln Trp Leu Pro Asp Glu Leu Arg Val Glu Lys Gly
                        515                 520                 525

Phe Ser Pro Asp Thr Leu Lys Leu Leu Glu Ala Lys Gly Gln Lys Val
                        530                 535                 540

Ala Leu Lys Glu Ala Met Gly Ser Thr Gln Ser Ile Met Val Gly Pro
        545                 550                 555                 560

Asp Gly Glu Leu Tyr Gly Ala Ser Asp Pro Arg Ser Val Asp Asp Leu
                        565                 570                 575

Thr Ala Gly Tyr
                        580

<210> SEQ ID NO 27
<211> LENGTH: 951
<212> TYPE: DNA
<213> ORGANISM: Escherichia coli

<400> SEQUENCE: 27
atgatcaagc tcggcatcgt gatggacccc atcgcaaaca tcaacatcaa gaaagattcc      60
agttttgcta tgttgctgga agcacagcgt cgtggttacg aacttcacta tatggagatg     120
```

-continued

```
ggcgatctgt atctgatcaa tggtgaagcc cgcgcccata cccgcacgct gaacgtgaag    180
cagaactacg aagagtggtt ttcgttcgtc ggtgaacagg atctgccgct ggccgatctc    240
gatgtgatcc tgatgcgtaa agacccgccg tttgataccg agtttatcta cgcgacctat    300
attctggaac gtgccgaaga aaagggacg ctgatcgtta caagccgca gagcctgcgc    360 gactgtaacg agaaactgtt taccgcctgg ttctctgact taacgccaga aacgctggtt    420
acgcgcaata aagcgcagct aaaagcgttc tgggagaaac acagcgacat cattcttaag    480
ccgctggacg gtatgggcgg cgcgtcgatt ttccgcgtga agaaggcga tccaaacctc    540 ggcgtgattg ccgaaaccct gactgagcat ggcactcgct actgcatggc gcaaaattac    600
ctgccagcca ttaaagatgg cgacaaacgc gtgctggtgg tggatggcga gccggtaccg    660
tactgcctgg cgcgtattcc gcaggggggc gaaacccgtg gcaatctggc tgccggtggt    720
cgcggtgaac ctcgtccgct gacggaaagt gactggaaaa tcgcccgtca gatcgggccg    780
acgctgaaaa aaaagggct gattttgtt ggtctggata tcatcggcga ccgtctgact    840
gaaattaacg tcaccagccc aacctgtatt cgtgagattg aagcagagtt tccggtgtcg    900
atcaccggaa tgttaatgga tgccatcgaa gcacgtttac agcagcagta a    951
```

<210> SEQ ID NO 28
<211> LENGTH: 316
<212> TYPE: PRT
<213> ORGANISM: Escherichia coli

<400> SEQUENCE: 28

```
Met Ile Lys Leu Gly Ile Val Met Asp Pro Ile Ala Asn Ile Asn Ile
1               5                   10                  15

Lys Lys Asp Ser Ser Phe Ala Met Leu Leu Glu Ala Gln Arg Arg Gly
            20                  25                  30

Tyr Glu Leu His Tyr Met Glu Met Gly Asp Leu Tyr Leu Ile Asn Gly
        35                  40                  45

Glu Ala Arg Ala His Thr Arg Thr Leu Asn Val Lys Gln Asn Tyr Glu
    50                  55                  60

Glu Trp Phe Ser Phe Val Gly Glu Gln Asp Leu Pro Leu Ala Asp Leu
65                  70                  75                  80

Asp Val Ile Leu Met Arg Lys Asp Pro Pro Phe Asp Thr Glu Phe Ile
                85                  90                  95

Tyr Ala Thr Tyr Ile Leu Glu Arg Ala Glu Glu Lys Gly Thr Leu Ile
            100                 105                 110

Val Asn Lys Pro Gln Ser Leu Arg Asp Cys Asn Glu Lys Leu Phe Thr
        115                 120                 125

Ala Trp Phe Ser Asp Leu Thr Pro Glu Thr Leu Val Thr Arg Asn Lys
    130                 135                 140

Ala Gln Leu Lys Ala Phe Trp Glu Lys His Ser Asp Ile Ile Leu Lys
145                 150                 155                 160

Pro Leu Asp Gly Met Gly Gly Ala Ser Ile Phe Arg Val Lys Glu Gly
                165                 170                 175

Asp Pro Asn Leu Gly Val Ile Ala Glu Thr Leu Thr Glu His Gly Thr
            180                 185                 190

Arg Tyr Cys Met Ala Gln Asn Tyr Leu Pro Ala Ile Lys Asp Gly Asp
        195                 200                 205

Lys Arg Val Leu Val Val Asp Gly Glu Pro Val Pro Tyr Cys Leu Ala
    210                 215                 220
```

```
Arg Ile Pro Gln Gly Gly Glu Thr Arg Gly Asn Leu Ala Ala Gly Gly
225                 230                 235                 240

Arg Gly Glu Pro Arg Pro Leu Thr Glu Ser Asp Trp Lys Ile Ala Arg
                245                 250                 255

Gln Ile Gly Pro Thr Leu Lys Glu Lys Gly Leu Ile Phe Val Gly Leu
                260                 265                 270

Asp Ile Ile Gly Asp Arg Leu Thr Glu Ile Asn Val Thr Ser Pro Thr
            275                 280                 285

Cys Ile Arg Glu Ile Glu Ala Glu Phe Pro Val Ser Ile Thr Gly Met
        290                 295                 300

Leu Met Asp Ala Ile Glu Ala Arg Leu Gln Gln Gln
305                 310                 315

<210> SEQ ID NO 29
<211> LENGTH: 1146
<212> TYPE: DNA
<213> ORGANISM: Kocuria rosea

<400> SEQUENCE: 29
atggaaatct cgtttgcccg cagtcaccag agcaccttag gcgtggagtg ggaaattgcg      60
cttgtggacg ggactacagg tgatctcgtc ccgcgtggtc gcgaaacgtt tgaagccgtt     120
ctggacgcac atccggcttg gggtacagac ggggaccatc gcacttaac gggtgaattc     180 ctgctgaata ccgtagaact ggtgaccggc gtttgtcgcg acgtcgcgca cagcaccgaa     240
cagctgagca caatgctgga tgaaattcgc aaggtgacgg atccgcaggg cctggaagtg     300
tttgccgcgg gaacgcatcc ctttgcccgc tggcaagacc aacaggttac cgataaacag     360
cggtatcaca aacttgtgga tcgcactcag tactggggtc gtcagatggt gatctatggc     420
gtgcacgtgc atgtcggcct ggatagccgt gccaaagcac tgcctgtact ggatggcctc     480
ctgacttact acccgcatct gttagccctg agtgcgaact ctccgttttg ggcgggcgaa     540
gatacggggt atgcaagcca acgctctatg atcttccagc agctgagtac agcgggttta     600
ccgtatcact tcccgtcatg ggatgcatac gagcagtgca tcaccgatat gattgccacc     660
ggtatcattg aggaaatgtc cgaagcccgt tgggatgttc gccccgttcc tcgcttaggg     720
acggatgagg tccgcttctg cgacggactg tcaacgttgt gggaagttgg tgcactcacc     780
gccctgaccc aatgcctggc ggagtccatt tcgcgtgatg tcgaagctgg tcgcccacca     840
gctcggttga aaccatggca tattcaggag aacaaatggc gtgctgcacg ctatggcctg     900
gacgcggaag tgattaccga tcctcgcaat gtggagcgcg atttgcgtac cgacctgacc     960
gcgttgctgg atcgtttgga accggtagca gcgcaactgg gctgttcgcg tgaactcgcg    1020
gatgttgaac gcatccttga gcaaggagca ggctatcagc gtcaacgcgc tgttgctcgg    1080
gcgcatgatg gcgatctgca tcggtagcc cttgacattg tccgtcgtac tcgcgaaaac    1140
gactaa                                                               1146
```

MICROORGANISM AND METHOD FOR PRODUCING GAMMA-GLUTAMYL-VALYL-GLYCINE

TECHNICAL FIELD

The present invention relates to a microorganism useful as an expression host for γ-glutamylvaline synthetase (γ-Glu-Val synthetase) and a method for producing γ-glutamyl-valylglycine using γ-glutamylvaline synthetase expressed in the microorganism. γ-Glutamylvalylglycine is useful in the fields of food, drug, and so forth.

BACKGROUND ART

Certain kinds of peptides such as γ-glutamylvalylglycine (L-γ-glutamyl-L-valyl-glycine, henceforth also referred to as "γ-Glu-Val-Gly") have a calcium sensing receptor agonist activity (Patent document 1). Such peptides having a calcium sensing receptor agonist activity are known to be able to impart "kokumi" to foods and drinks (Patent document 2), improve tastes of low fat foods, especially fat-like thickness and smoothness (Patent document 3), improve feeling of body of sweet taste substances, and improve bitterness peculiar to sweet taste substances (Patent document 4).

Moreover, such peptides as mentioned above are known to have a prophylactic or curative effect on diarrhea (Patent document 5) and diabetes (Patent document 6), and a bicarbonate secretion promoting effect in the alimentary tract (Patent document 7).

As methods for producing γ-glutamyl tripeptides, chemical synthesis methods and enzymatic methods are generally known. As one of the chemical synthesis methods, a method of selectively obtaining a γ-glutamyl tripeptide from a dipeptide by using N-protected glutamic anhydride is known (Patent document ti). As one of the enzymatic methods, there is known a method of using glutamate-cysteine ligase (GSHA) and glutathione synthetase (GSHB) is known (Patent documents 9 and 10). As another enzymatic method, there is also known a method of γ-glutamylating Val-Gly by using γ-glutamyltransferase to generate γ-Glu-Val-Gly (Patent document 11).

Glutamate-cysteine ligase (GSHA) is known as an enzyme having an activity for catalysing the reaction of generating γ-Glu-Cys. ADP, and phosphate using Glu, Cys, and ATP as substrates (EC 6.3.2.2). GSHA usually requires divalent metal ions such as $Mg^{2+}$ and $Mn^2$ for the enzymatic reaction.

GSHA of *Escherichia coli* generates γ-glutamyl dipeptides using Glu, various kinds of amino acids, and ATP as substrates in the presence of $Mg^2$ or $Mn^2$, and it is known that type of the metal ion serving as a cofactor affects the substrate specificity thereof (Non-patent document 1). Specifically, it has been reported that when $Mg^2$ is used as the cofactor, Vmax is 251 mol/mg/hr and Km is 17.6 mM as for the γ-Glu-Gly generating activity, whereas Vmax is 59 mol/mg/hr and Km is 27.1 mM as for the γ-Glu-Val generating activity. That is, if the activities are compared by using Vmax/Km as index of the activities, the ratio of γ-Glu-Val generating activity to the γ-Glu-Gly generating activity in the case of using $Mg^{2+}$ as the cofactor can be calculated to be 0.15. Furthermore, it has been demonstrated that when $Mn^{2+}$ is used as the cofactor, Vmax is 39 mol/mg/hr and Km is 1.7 mM as for the γ-Glu-Gly generating activity, whereas Vmax is 95 mol/mg/hr and Km is 21 mM as for the γ-Glu-Val generating activity. That is, if the activities are compared by using Vmax/Km as index of the activities, the ratio of γ-Glu-Val generating activity to the γ-Glu-Gly generating activity in the case of using $Mn^{2+}$ as the cofactor can be calculated to be 0.20. Furthermore, as for the substrate specificity of GSHA derived from *Escherichia coli*, there are also other examples of measurement of the activity (Non-patent document 2). This document reported that the reaction was performed by using Glu, various kinds of amino acids, and ATP as the substrates in the presence of $Mg^{2+}$, and when the γ-Glu-Gly generating activity was taken as 100%, the γ-Glu-Val generating activity was about 52%. That is, if the activities are compared by using these relative activities, the ratio of the γ-Glu-Val generating activity to the γ-Glu-Gly generating activity can be calculated to be 0.52. Thus, it can be said that the ratio of the γ-Glu-Val generating activity to the γ-Glu-Gly generating activity of GSHA of *Escherichia coli* is about 0.15 to 0.5. Furthermore, it has also been reported that GSHA of *Escherichia coli* was introduced with various mutations to obtain mutant GSHAs showing a high ratio of the γ-Glu-Val generating activity to the γ-Glu-Gly generating activity (Patent document 12).

It is also known that GSHA derived from *Proteus mirabilis*, a kind of gram-negative bacteria, generates γ-glutamyl dipeptides by using $Mg^{2+}$ or $Mn^{2+}$ as a cofactor, as well as Glu, various kinds of amino acids, and ATP as substrates (Non-patent document 3). It has been reported that if the γ-Glu-Cys generating activity of GSHA derived from *Proteus mirabilis* is taken as 100%, the γ-Glu-Gly generating activity and γ-Glu-Val generating activity of the same correspond to 14.5% and 7.2%, respectively. That is, if the activities are compared on the basis of these relative activities, the ratio of γ-Glu-Val generating activity to the γ-Glu-Gly generating activity can be calculated to be 0.50.

It is also known that γ-glutamylcysteine synthetase-glutathione synthetase (γ-GCS-GS) of *Streptococcus agalactiae* generates γ-glutamyl dipeptides by using Glu, various kinds of amino acids, and ATP as the substrates in the presence of $Mg^2$. As for γ-GCS-CS of *Streptococcus agalactiae*, it was reported that when the γ-Glu-Gly generating activity was taken as 100%, the γ-Glu-Val generating activity was about 21% (Non-patent document 2). That is, if the activities are compared on the basis of these relative activities, the ratio of γ-Glu-Val generating activity to the γ-Glu-Gly generating activity can be calculated to be 0.21.

Furthermore, it was reported that culture broth of *Micrococcus glutamicus* was applied to various columns to separate peptides etc., and thereby γ-Glu-Glu, γ-Glu-Val, and γ-Glu-Leu were isolated (Non-patent document 4). However, the biosynthetic pathways of these γ-glutamyl dipeptides were not reported.

It has been reported that a protein encoded by ybdK gene (YBDK) of *Escherichia coli* has the γ-Glu-Cys generating activity (Non-patent document 5). However, there have not been reported γ-glutamyl dipeptide generation activities other than the γ-Glu-Cys generating activity for YBDK of *Escherichia coli*.

PRIOR ART REFERENCES

Patent Documents

Patent document 1: WO2007/055388
Patent document 2: WO2007/055393
Patent document 3: WO2008/139945
Patent document 4: WO2008/139946
Patent document 5: WO2008/139947
Patent document 6: WO2009/107660
Patent document 7: WO2009/119554

Patent document 8: Japanese Patent Laid-open (Kokai) No. 08-119916
Patent document 9: WO2013/054447
Patent document 10: Japanese Patent Laid-open (Kokai) No. 2012-85637
Patent document 11: WO2013/051685
Patent document 12: WO2015/115612

Non-Patent Documents

Non-patent document 1: Brenda S. Kelly et al., J. Biol. Chem., 277, 50-58, 2002
Non-patent document 2: Kino, K. et al., Biochem. Biophys. Res. Commun., 352, 351-359, 2007
Non-patent document 3: Kumagai. H. et al., Agric. Biol. Chem., 46, 1301-1309. 19112
Non-patent document 4: Ronald A. Vitali et al., J. Biol. Chem., 240, 2508-2511, 1965
Non-patent document 5: Lehmann C. et al., Proteins. 2004 Aug 1;56(2):376-83.

SUMMARY OF THE INVENTION

Object to be Achieved by the Invention

An object of the present invention is to provide a microorganism useful as an expression host for γ-glutamylvaline synthetase (γ-Glu-Val synthetase), and a method for producing γ-Glu-Val-Gly using γ-glutamylvaline synthetase expressed in the microorganism.

Means for Achieving the Object

The inventors of the present invention conducted various researches in order to achieve the aforementioned object, as a result, found that YBDK of *Escherichia coli* has the γ-Glu-Gly generating activity and *Escherichia coli* deficient in YBDK is useful as an expression host for γ-Glu-Val synthetase, and accomplished the present invention.

Thus, the present invention can be embodied, for example, as follows.

A bacterium,
  wherein the bacterium has been modified so that the activity of a protein encoded by a ybdK gene is reduced as compared with a non-modified strain.
  wherein the bacterium has a gene encoding γ-glutamylvaline synthetase, and
  wherein the γ-glutamylvaline synthetase shows a ratio of γ-glutamylvaline synthetase activity to γ-glutamylglycine synthetase activity of 3.0 or higher.
The bacterium mentioned above, wherein the protein is a protein defined in (a), (b), or (c) mentioned below:
  (a) a protein comprising the amino acid sequence of SEQ ID NO: 16;
  (b) a protein comprising the amino acid sequence of SEQ ID NO: 16 but including substitution, deletion, insertion, or addition of 1 to 10 amino acid residues, and having γ-glutamylglycine synthetase activity;
  (c) a protein comprising an amino acid sequence showing an identity of 9(N/e or higher to the amino acid sequence of SEQ ID NO: 16, and having γ-glutamylglycine synthetase activity.
The bacterium mentioned above, wherein the activity of the protein is reduced by attenuating the expression of the ybdK gene, or by disrupting the ybdK gene.
The bacterium mentioned above, wherein the γ-glutamylvaline synthetase is a protein defined in (a), (b), or (c) mentioned below:
  (a) a protein comprising the amino acid sequence of SEQ ID NO: 18, 20, or 22;
  (b) a protein comprising the amino acid sequence of SEQ ID NO: 18, 20, or 22 but including substitution, deletion, insertion, or addition of 1 to 10 amino acid residues, and having γ-glutamylvaline synthetase activity;
  (c) a protein comprising an amino acid sequence showing an identity of 90% or higher to the amino acid sequence of SEQ ID NO: 1K, 20, or 22, and having γ-glutamylvaline synthetase activity.
The bacterium mentioned above, wherein the γ-glutamylvaline synthetase is a mutant glutamate-cysteine ligase having a mutation for an amino acid residue or amino acid residues corresponding to one or more amino acid residues selected from those mentioned below in a wild-type glutamate-cysteine ligase, and having the γ-glutamylvaline synthetase activity:
L135. Q144. Y241. N243. Y300.
The bacterium mentioned above, wherein the mutation includes a mutation corresponding to one or more mutations selected from those mentioned below:
  L135(1, F, M, V, G, A, W, K, H, R, C, N, S, T),
  Q144(F, A, N, S, D, T, R, H, G, K, Y, W, C, M, P, V, L, I),
  Y241(A),
  N243(I, W, K, R, H),
  Y300(A, H, R, K).
The bacterium mentioned above, wherein the mutation includes a mutation corresponding to any one of the following mutations:
L135I/Q144R, L135I/Q144D, L135I/Q144A, L135I/Q144L, L135I/N243W, L135I/N243F, L135F/Q144A, L135F/N243W, L135M/Q144R, L135M/Q144A, L135M/Q144L, L135M/N243W, L135M/N243F, L135M/Q144H, L135M/Q144N, L135M/N243Y, L135M/N243R, L135M/N243C, L135V/Q144R, L135V/Q144D, L135V/Q144A, L135V/Q144L, L135V/Q144V, L135V/Q144K, L135V/Q144C, L135V/Q144T, L135H/Q144R, L135G/Q144L, L135A/Q144L, L135V/N243W, L135V/N243F, L135V/N243P, Q144R/N243W, Q144R/N243F, Q144D/N243W, Q144D/N243F, Q144A/N243 W, Q144A/N243 F, Q144L/N243 W, Q144L/N243 F, L135M/Q144F, L135M/N243A, L135V/N243G, L135V/N243A, L135V/N243L, L135V/N243Y, LI 35V/N243K, L135V/N243R, L135V/N243H, LI 35V/N243D, L135V/N243E, L135V/N243C, L135V/N243Q, L135V/N243S, L135V/N243T, L135V/Q144I, L135V/Q144P, L135V/Q144W, L135V/Q144H, L135V/Q144E, L135V/Q144N, L135V/Q144S, L135K/Q144L, L135H/Q144L, L135D/Q144L, L135C/Q144L, L135Q/Q144L, L135N/Q144L, L135S/Q144L, L135T/Q144L.
The bacterium mentioned above, wherein the mutation includes a mutation corresponding to any one of the following mutations:
  L135(I, M, V, G, A, K, H, C, N, S, T),
  Q144(F, A, S, D, T, R, H, K, Y, W, C, M, P, V, L, I),
  N243(R, H),
  Y300(R, K),
  L135I/Q144R, L135I/Q144D, L135I/Q144A, L135I/Q144L, L135I/N243W, L135I/N243F, L135F/Q144A, L135M/Q144R, L135M/Q144A, L135M/Q144L, L135M/N243W, L135M/Q144H, L135M/Q144N, L135M/N243C, L135V/Q144R, L13S V/Q144D, L135V/Q144A, L135V/Q144L, L135V/Q144V. L135V/Q144K, L135V/Q144C, L135V/Q144T, L135H/Q144R, L135G/Q144L, L135A/Q144L, L135V/N243W, L135V/N243F, L135V/N243P, Q144R/N243W, Q144D/N243W, Q144A/N243W, Q144A/N243F, Q144L/N243W, Q144L/N243F, L135M/Q144F, L135M/N243A, L135V/N243Q L135V/N243A, L135V/N243L, L135V/N243Y, L135V/N243K, L135V/N243R, L135V/N243H, L135V/N243D, L135V/N243E, L135V/N243C, L135V/N243Q, L135V/N243S, LI 35V/N243T, L135V/Q144P, L135V/Q144W, L135V/Q144H, L135V/Q144E, L135V/Q144N, L135V/Q144S. L135D/Q144L, L135C/Q144L, L135N/Q144L, L135S/Q144L, L135T/Q144L.

The bacterium mentioned above, wherein the wild-type glutamate-cysteine ligase is a protein defined in (a), (b), or (c) mentioned below:

(a) a protein comprising the amino acid sequence of SEQ ID NO: 24;

(b) a protein comprising the amino acid sequence of SEQ ID NO: 24 but including substitution, deletion, insertion, or addition of 1 to 10 amino acid residues:

(c) a protein comprising an amino acid sequence showing an identity of 90% or higher to the amino acid sequence of SEQ ID NO: 24.

The bacterium mentioned above, wherein the bacterium has been further modified so that the activity of a protein encoded by a gehA gene is reduced as compared with a non-modified strain.

The bacterium mentioned above, wherein the bacterium has been further modified so that the activity of γ-glutamyltransferase is reduced as compared with a non-modified strain.

The bacterium mentioned above, wherein the bacterium has a gene encoding glutathione synthetase.

The bacterium mentioned above, wherein the bacterium is an *Escherichia coli* bacterium.

The bacterium mentioned above, wherein the bacterium is *Escherichia coli*.

A method for producing γ-Glu-Val-Gly and/or a salt thereof, the method comprising:

a step of allowing γ-glutamylvaline synthetase and glutathione synthetase to act on Glu, Val, and Gly to generate γ-Glu-Val-Gly, wherein the γ-glutamylvaline synthetase is an enzyme obtained by using the bacterium as an expression host.

The method mentioned above, wherein the glutathione synthetase is an enzyme obtained by using the bacterium as an expression host.

The method mentioned above, wherein the γ-glutamylvaline synthetase is a purified enzyme.

The method mentioned above, wherein the γ-glutamylvaline synthetase is an immobilized enzyme.

The method mentioned above, wherein the γ-glutamylvaline synthetase is an enzyme contained in a culture broth of the bacterium, cultured cells of the bacterium, or a processed product of the cells.

The method mentioned above, wherein the glutathione synthetase is an enzyme contained in a culture broth of a microorganism having the enzyme, cultured cells of the microorganism, or a processed product of the cells.

The method mentioned above, wherein the γ-glutamylvaline synthetase and glutathione synthetase are enzymes contained in a culture broth of the bacterium, cultured cells of the bacterium, or a processed product of the cells.

The method mentioned above, wherein the step is carried out in the presence of ATP The method mentioned above, wherein the step is carried out in the presence of a divalent metal ion.

MODES FOR CARRYING OUT THE INVENTION

Hereafter, the present invention will be explained in detail. In this description, amino acids are L-amino acids, unless especially indicated.

<I>Microorganism of the Present Invention

The microorganism of the present invention is a bacterium that has been modified so that the activity of a protein encoded by a ybdK gene (also referred to as "YBDK") is reduced. Specifically, the microorganism of the present invention is a bacterium that has been modified so that the activity of YBDK is reduced as compared with a non-modified strain. The microorganism of the present invention can be obtained by, for example, modifying such a bacterium as mentioned below so that the activity of YBDK is reduced.

Examples of the bacterium include, for example, bacteria belonging to the family Enterobacteriaceae, coryneform bacteria, and *Bacillus* bacteria.

Examples of bacteria belonging to the family Enterobacteriaceae include bacteria belonging to the genus *Escherichia, Enterobacter, Pantoea, Klebsiella, Serratia, Erwinia, Photorhabdus, Providencia, Salmonella, Morganella*, or the like. Specifically, bacteria classified into the family Enterobacteriaceae according to the taxonomy used in the NCBI (National Center for Biotechnology Information) database www(dot)ncbi (dot)nlm(dot)nih(dot)gov/Taxonomy-Browser/wwwtax.cgi?id=913 47) can be used. The *Escherichia* bacteria are not particularly limited, and examples thereof include those classified into the genus *Escherichia* according to the taxonomy known to those skilled in the field of microbiology. Examples of the *Escherichia* bacteria include, for example, those described in the work of Neidhardt et al. (Backmann B. J., 1996. Derivations and Genotypes of some mutant derivatives of *Escherichia coli* K-12. pp. 2460-2488, Table 1, In F. D. Neidhardt (ed.), *Escherichia coli* and *Salmonella* Cellular and Molecular Biology/Second Edition, American Society for Microbiology Press, Washington, D.C.). Examples of the *Escherichia* bacteria include, for example, *Escherichia coli*. Examples of *Escherichia coli* include, for example, *Escherichia coli* K-12 strains such as W3110 strain (ATCC 27325) and MG1655 strain (ATCC 47076); *Escherichia coli* K5 strain (ATCC 23506); *Escherichia coli* B strains such as BL21(DE3) strain; and derivative strains thereof, e.g. JM109 strain, which is derived from the K-12 strain.

The *Enterobacter* bacteria are not particularly limited, and examples include those classified into the genus *Enterobacter* according to the taxonomy known to those skilled in the field of microbiology. Examples the *Enterobacter* bacterium include, for example *Enterobacter agglomerans* and *Enterobacter aerogenes*. Specific examples of *Enterobacter agglomerans* include, for example, the *Enterobacter agglomerans* ATCC 122117 strain. Specific examples of *Enterobacter aerogenes* include, for example, the *Enterobacter aerogenes* ATCC 13048 strain. NBRC 12010 strain (Biocechnol. Bioeng., 2007, Mar. 27;98(2):340-348), and AJ110637 strain (FERM BP-10955). Examples the *Enterobacter* bacteria also include, for example, the strains described in European Patent Application Laid-open (EP-A) No. 0952221. In addition, *Enterobacter agglomerans* also include some strains classified as *Pantoea agglomerans*. The

*Pantoea* bacteria are not particularly limited, and examples include those classified into the genus *Pantoea* according to the taxonomy known to those skilled in the field of microbiology. Examples the *Pantoea* bacteria include, for example, *Pantoea ananatis*, *Pantoea stewartii*, *Pantoea agglomerans*, and *Pantoea citrea*. Specific examples of *Pantoea ananatis* include, for example, the *Pantoea ananatis* LMG20103 strain, AJ13355 strain (FERM BP-6614), AJ13356 strain (FERM BP-6615), AJ13601 strain (FERM BP-7207), SC17 strain (FERM BP-11091), SC17(0) strain (VKPM B-9246), and SC17sucA strain (FERM BP-8646). Some strains of *Enterobacter agglomerans* were recently reclassified into *Pantoea agglomerans*, *Pantoea ananatis*, *Pantoea stewartii*, or the like on the basis of nucleotide sequence analysis of 16S rRNA etc. (Int. J. Syst. Bacteriol., 43, 162-173 (1993)). In the present invention, the *Pantoea* bacteria include those reclassified into the genus *Pantoea* as described above.

Examples of the *Erwinia* bacteria include *Erwinia amylovora* and *Erwinia carotovora*. Examples of the *Klebsiella* bacteria include *Klebsiella planticola*.

Examples of the coryneform bacteria include bacteria belonging to the genus *Corynebacterium, Brevibacterium, Microbacterium*, or the like.

Specific examples of the coryneform bacteria include the following species.

*Corynebacterium acetoacidophilum*
*Corynebacterium acetoglutamicum*
*Corynebacterium alkanolyticum*
*Corynebacterium callunae*
*Corynebacterium crenatum*
*Corynebacterium glutamicum*
*Corynebacterium lilium*
*Corynebacterium melassecola*
*Corynebacterium thermoaminogenes* (*Corynebacterium efficiens*)
*Corynebacterium herculis*
*Brevibacterium divaricatum* (*Corynebacterium glutamicum*)
*Brevibacterium flavum* (*Corynebacterium glutamicum*)
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Corynebacterium amnioniagenes* (*Corynebacterium stationis*)
*Brevibacterium album*
*Brevibacterium cerinum*
*Microbacterium ammoniaphilum*

Specific examples of the coryneform bacteria include the following strains.

*Corynebacterium aceloacidophilum* ATCC 13870
*Corynebacterium aceloglutamicum* ATCC 15806
*Corynebacterium alkanolyticum* ATCC 21511
*Corynebacterium crenatum* AS1.542
*Corynebacterium callunae* ATCC 15991
*Corynebacterium glutamicum* ATCC 13020, ATCC 13032, ATCC 13060, ATCC 13869, FERM BP-734
*Corynebacterium lilium* ATCC 15990
*Corynebacterium melassecola* ATCC 17965
*Corynebacterium efficiens* (*Corynebacterium thermoaminogenes*) AJ12340 (FERM BP-1539)
*Corynebacterium herculis* ATCC 13868
*Brevibacterium divaricatum* (*Corynebacterium glutamicum*) ATCC 14020
*Brevibacterium flavum* (*Corynebacterium glutamicum*) ATCC 13826, ATCC 14067, AJ12418 (FERM BP-2205)
*Brevibacterium immariophilum* ATCC 14068
*Brevibacterium lactofermentum* (*Corynebacterium glutamicum*) ATCC 13869
*Brevibacterium roseum* ATCC 13825
*Brevibacterium saccharolyticum* ATCC 14066
*Brevibacterium thiogenitalis* ATCC 19240
*Corynebacterium ammoniagenes* (*Corynebacterium stationis*) ATCC 6871, ATCC 6872
*Brevibacterium album* ATCC 15111
*Brevibacterium cerinum* ATCC 15112
*Microbacterium ammoniaphilum* ATCC 15354

The *Corynebacterium* bacteria include bacteria that had previously been classified into the genus *Brevibacterium*, but are presently united into the genus *Corynebacterium* (Int. J. Syst. Bacteriol., 41, 255 (1991)). Moreover, *Corynebacterium stationis* includes bacteria that had previously been classified as *Corynebacterium ammoniagenes*, but are presently re-classified into *Corynebacterium stationis* on the basis of nucleotide sequence analysis of 16S rRNA etc. (Int. J. Syst. Evol. Microbiol., 60, 874-879 (2010)).

The *Bacillus* bacteria are not particularly limited, and examples thereof include those classified into the genus *Bacillus* according to the taxonomy known to those skilled in the field of microbiology. Examples of the *Bacillus* bacteria include, for example, *Bacillus subtilis*, *Bacillus amyloliquefaciens*, *Bacillus pumilus*, *Bacillus licheniformis*, *Bacillus megalerlum*, *Bacillus brevis*, *Bacillus polvmixa*, and *Bacillus stearothermophilus*. Specific examples of *Bacillus subtilis* include, for example, the *Bacillus subtilis* 168 Marburg strain (ATCC 6051) and the *Bacillus subtilis* PY79 strain (Plasmid, 1984, 12, 1-9). Specific examples of *Bacillus amyloliquefaciens* include, for example, the *Bacillus amyloliquefaciens* T strain (ATCC 23842) and the *Bacillus amyloliquefaciens* N strain (ATCC 23845).

These strains are available from, for example, the American Type Culture Collection (Address: 10801 University Boulevard, Manassas, Va. 20110, United States of America). That is, registration numbers are given to the respective strains, and the strains can be ordered by using these registration numbers (refer to www(dot)atcc(dot)org/). The registration numbers of the strains are listed in the catalogue of the American Type Culture Collection. These strains can also be obtained from, for example, the depositories at which the strains were deposited. The BL21(DE3) strain is available from, for example, Life Technologies (product number C6000-03). The BLR(DE3) strain is available from, for example, Merck Millipore (product number 69053). The JM109 strain is available from, for example, Takara Bio (product number 9052).

YBDK is a protein having the activity for catalyzing the reaction of generating γ-Glu-Gly, ADP, and phosphate using Glu, Gly, and ATP as substrates. This activity is also referred to as "γ-glutamylglycine synthetase activity", "γ-Glu-Gly generating activity", or "γ-Glu-Gly synthetic activity".

Furthermore, the activity for catalyzing the reaction of generating γ-Glu-Val, ADP, and phosphate using Glu, Val, and ATP as substrates is also referred to as "γ-glutamylvaline synthetase activity", "γ-Glu-Val generating activity", or "γ-Glu-Val synthetic activity".

Furthermore, the activity for catalyzing the reaction of generating γ-Glu-Cys. ADP, and phosphate using Glu, Cys, and ATP as substrates is also referred to as "γ-glutamylcysteine synthetase activity".

These enzymatic activities each can be measured on the basis of, for example, generation of the corresponding γ-glutamyl dipeptide upon allowing an enzyme to act on the substrates under appropriate conditions. These enzymatic activities each can be measured, for example, in the presence of a divalent metal ion. Examples of the divalent metal ion include $Mg^{2+}$ and $Mn^{2+}$.

Examples of conditions for measuring the γ-glutamylvaline synthetase activity and γ-glutamylglycine synthetase activity in the presence of $Mn^{2+}$ include conditions described in Example 3. That is, specific conditions for measurement of the activities are as follows. The γ-glutamylvaline synthetase activity can be measured by adding an appropriate amount of enzyme to a reaction mixture (10 mM glutamic acid, 10 mM valine, 10 mM ATP, 10 mM $MnSO_4$, and 100 mM Tris-HCl, pH 7.0-9.0), performing the reaction at 30° C. for 30 minutes, and calculating the activity on the basis of the amount of generated γ-Glu-Val. In the present invention, the enzymatic activity for generating 1 μmol αy-Glu-Val in 1 minute under the aforementioned conditions is defined as 1 U of the γ-glutamylvaline synthetase activity (in the presence of $Mn^2$). Similarly, the γ-glutamylglycine synthetase activity can be measured by adding an appropriate amount of enzyme to a reaction mixture (10 mM glutamic acid, 10 mM glycine, 10 mM ATP, 10 mM $MnSO_4$, and 1(0 mM Tris-HCl, pH 7.0-9.0), performing the reaction at 30° C. for 30 minutes, and calculating the activity on the basis of the amount of generated γ-Glu-Gly. In the present invention, the enzymatic activity for generating 1 μmol of γ-Glu-Gly in 1 minute under the aforementioned conditions is defined as 1 U of the γ-glutamylglycine synthetase activity (in the presence of $Mn^2$).

Furthermore, by using a reaction mixture containing 10 mM $MgSO_4$ instead of 10 mM $MnSO_4$, the γ-glutamylvaline synthetase activity and γ-glutamylglycine synthetase activity in the presence of $Mg^{2+}$ can be measured. That is, the enzymatic activity for generating 1 μmot of γ-Glu-Val in 1 minute under the aforementioned conditions using this reaction mixture is defined as 1 U of the γ-glutamylvaline synthetase activity (in the presence of $Mg^2$). Similarly, the enzymatic activity for generating 1 μmol of γ-Glu-Gly in 1 minute under the aforementioned conditions using this reaction mixture is defined as 1 U of the γ-glutamylglycine synthetase activity (in the presence of $Mg^2$).

A ratio of the γ-glutamylvaline synthetase activity (specific activity) to the γ-glutamylglycine synthetase activity (specific activity), i.e. the specific activity of γ-glutamylvaline synthetase activity/the specific activity of γ-glutamylglycine synthetase activity, is also referred to as "Val-selectivity". The Val-selectivity can be obtained by measuring the γ-glutamylvaline synthetase activity and γ-glutamylglycine synthetase activity, and calculating the ratio therefrom.

YBDK may have or may not have an activity of generating a γ-glutamyl dipeptide other than γ-glutamylglycine, so long as YBDK has the γ-glutamylglycine synthetase activity. That is, for example, YBDK may have or may not have the γ-glutamylvaline synthetase activity. Also, for example YBDK may have or may not have the γ-glutamyl-cysteine synthetase activity. 11 is sufficient that YBDK has the γ-glutamylglycine synthetase activity under appropriate conditions. YBDK may have the γ-glutamylglycine synthetase activity, for example, in the presence of $Mg^{2+}$ or $Mn^{2+}$, or particularly in the presence of $Mn^{2+}$. YBDK may have the γ-glutamylglycine synthetase activity, for example, at least at one pH of pH7.0-9.0, or particularly at pH7.0.

The Val-selectivity of YBDK is not particularly limited, so long as YBDK has the γ-glutamylglycine synthetase activity. The Val-selectivity of YBDK may be lower than that of γ-glutamylvaline synthetase described later. The Val-selectivity of YBDK may be, for example, lower than 3.0. YBDK may show the Val-selectivity exemplified above, for example, in the presence of $Mg^{2+}$ or $Mn^{2+}$, or particularly in the presence of $Mn^2$. YBDK may show the Val-selectivity exemplified above, for example, at least at one pH of pH7.0-9.0, or particularly at pH7.9.

The nucleotide sequence of the ybdK gene of *E. coli* K-12 MG1655 and the amino acid sequence of YBDK encoded by the gene are shown in SEQ ID NOS: 15 and 16. respectively. That is. YBDK may be, for example, a protein having the amino acid sequence of SEQ ID NO: 16. Furthermore. YBDK may be, for example, a protein encoded by a gene having the nucleotide sequence of SEQ ID NO: 15. The expression of "having an (amino acid or nucleotide) sequence" includes both cases of "comprising the (amino acid or nucleotide) sequence" and "consisting of the (amino acid or nucleotide) sequence".

YBDK may be a variant of the YBDK exemplified above (for example, a protein having the amino acid sequence shown as SEQ ID NO: 16), so long as the original function is maintained. Similarly, the ybdK gene may be a variant of the ybdK gene exemplified above (for example, a gene having the nucleotide sequence shown as SEQ ID NO: 15), so long as the original function is maintained. Such a variant that maintains the original function is also referred to as "conservative variant". That is, the term "ybdK gene" includes not only the ybdK gene exemplified above, but also includes conservative variants thereof. Similarly, the term "YBDK" includes not only the YBDK exemplified above, respectively, but also includes conservative variants thereof. Examples of the conservative variant include, for example, a homologue and artificially modified version of the ybdK gene and YBDK exemplified above.

The expression "the original function is maintained" means that a variant of the gene or protein has a function (activity or property) corresponding to the function (activity or property) of the original gene or protein. That is, the expression "the original function is maintained" means that, in the case of YBDK, a variant of the protein has the γ-glutamylglycine synthetase activity. The enzymatic characteristics of the variant. such as substrate specificity, requirement for divalent metal ions, and pH dependency, each may be or may not be identical to those of the original protein, so long as the variant has the γ-glutamylglycine synthetase activity. For example, the variant may have or may not have an activity of generating a γ-glutamyl dipeptide other than γ-glutamylglycine. Also, the variant may show the Val-selectivity exemplified above. Furthermore, the expression "the original function is maintained" means that, in the case of the ybdK gene, a variant of the gene encodes a protein that maintains the original function (namely, a protein having the γ-glutamylglycine synthetase activity).

Hereinafter, examples of the conservative variants will be explained.

Examples of homologues of the aforementioned ybdK gene or YBDK include, for example, genes and proteins obtained from a public database by BLAST search and FASTA search using the aforementioned nucleotide or amino acid sequence as a query sequence. Also, homologues of the aforementioned ybdK gene can be obtained by, for example, PCR using a chromosome of any of various microorganisms as the template, and oligonucleotides prepared on the basis of any of those known gene sequences as the primers.

YBDK may be a protein having an amino acid sequence corresponding to the aforementioned amino acid sequence (for example, the amino acid sequence shown as SEQ ID NO: 16), but including substitution, deletion, insertion, or addition of one or several amino acid residues at one or several positions, so long as it maintains the original function. Although the number meant by the term "one or several" can differ depending on the positions of amino acid residues in the three-dimensional structure of the protein, or the types of amino acid residues, specifically, it is, for example, 1 to 50, 1 to 40, 1 to 30, preferably 1 to 20, more preferably 1 to 10, still more preferably 1 to 5, particularly preferably 1 to 3.

The aforementioned substitution, deletion, insertion, or addition of one or several amino acid residues is a conservative mutation that maintains normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid: between Gin and Asn, if it is a polar amino acid; among Lys, Arg, and His, if it is a basic amino acid; between Asp and oho, if it is an acidic amino acid; and between Ser and Thr, if it is an amino acid having a hydroxyl group. Examples of substitutions considered as conservative substitutions include, specifically, substitution of Ser or Thr for Ala, substitution of Gin, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys. His, Asp, or Arg for Gln, substitution of Gly, Asn, Gin. Lys, or Asp for Glu, substitution of Pro for fly, substitution of Asn. Lys. Gln, Arg. or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Irp, Iyr, Met, lie, or Leu for Phe, substitution of 1 hr or Ala for Ser, substitution of Ser or Ala for Thr, substitution of Phe or Tyr for Trp, substitution of His, Phe, or Tip for Tyr, and substitution of Met, Ile, or Leu for Val. Furthermore, such substitution, deletion, insertion, addition, inversion, or the like of amino acid residues as mentioned above includes a naturally occurring mutation (mutant or variant), such as those due to a difference of individuals or species of the organism from which the protein is derived.

YBDK may be a protein having an amino acid sequence showing a homology of 80% or higher, preferably 90% or higher, more preferably 95% or higher, still more preferably 97% or higher, particularly preferably 99% or higher, to the whole of the aforementioned amino acid sequence, so long as the original function is maintained. In this description. "homology" means "identity".

YBDK may be a protein encoded by a DNA that hybridizes under stringent conditions with a probe that can be prepared from the aforementioned nucleotide sequence (for example, the nucleotide sequence shown as SEQ ID NO: 15), such as a sequence complementary to a pan, or the whole of the aforementioned nucleotide sequence, so long as the original function is maintained. Such a probe can be prepared by PCR using oligonucleotides produced on the basis of the aforementioned nucleotide sequence as primers, and a DNA fragment containing the aforementioned nucleotide sequence as the template. The "stringent conditions" refer to conditions under which a so-called specific hybrid is formed, and a non-specific hybrid is not formed. Examples of the stringent conditions include those under which highly homologous DNAs hybridize to each other, for example, DNAs not less than 80% homologous, preferably not less than 90% homologous, more preferably not less than 95% homologous, still more preferably not less than 97% homologous, particularly preferably not less than 99% homologous, hybridize to each other, and DNAs less homologous than the above do not hybridize to each other, or conditions of washing of typical Southern hybridization, i.e., conditions of washing once, preferably 2 or 3 times, at a salt concentration and temperature corresponding to 1×SSC, 0.1% SDS at 60° C., preferably 0.1×SSC, 0.1% SDS at 60° C., more preferably 0.1×SSC, 0.1% SDS at 68° C. Furthermore, for example, when a DNA fragment having a length of about 3110 bp is used as the probe, the washing conditions of the hybridization can be, for example, 50° C. 2×SSC, and 0.1% SDS.

The percentage of the sequence identity between two sequences can be determined by, for example, using a mathematical algorithm. Non-limiting examples of such a mathematical algorithm include the algorithm of Myers and Miller (1988) CA BIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and an modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison (i.e. alignment) for determining the sequence identity can be performed. The program can be appropriately executed by a computer. Examples of such a program include, but not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244 (1988), Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, BLAST nucleotide search can be performed by using BLASTN program with score of 100 and word length of 12. In order to obtain an amino acid sequence homologous to a target protein, in particular, for example, BLAST protein search can be performed by using BLASTX program with score of 50 and word length of 3. See www(dot)ncbi(dot)nlm(dot)nih(dot)gov for BLAST nucleotide search and BLAST protein search. In addition, Gapped BLAST (BLAST 2.0) can be used in order to obtain an alignment including gap(s) for the purpose of comparison. In addition, PSI-BLAST can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program (e.g. BLASTN for nucleotide sequences, and BLASTX for amino acid sequences) can be used. Alignment can also be manually performed.

The sequence identity between two sequences is calculated as the ratio of residues matching in the two sequences when aligning the two sequences so as to fit maximally with each other.

The microorganism of the present invention may have been further modified so that the activity of γ-glutamylcysteine synthetase is reduced. The term "γ-glutamylcysteine synthetase" refers to a protein having the γ-glutamylcysteine synthetase activity. γ-Glutamylcysteine synthetase is also referred to as "glutamate-cysteine ligase" or "GSHA". γ-Glutamylcysteine synthetase may further have an activity of generating a γ-glutamyl dipeptide other than γ-glutamylcysteine, such as the γ-glutamylvaline synthetase activity and the γ-glutamylglycine synthetase activity. The Val-selectivity of γ-glutamylcysteine synthetase may be lower than that of γ-glutamylvaline synthetase described later. The Val-selectivity of γ-glutamylcysteine synthetase may be, for example, lower than 3.0. Examples of γ-glutamylcysteine synthetase include a GshA protein encoded by a gshA gene. As an example, the nucleotide sequence of the gshA gene of *Escherichia coli* and the amino acid sequence of the protein encoded by the gene are shown in SEQ ID NOS: 23 and 24, respectively. γ-Glutamylcysteine synthetase may be a variant of the γ-glutamylcysteine synthetase exemplified above, so long as the variant has the γ-glutamylcysteine synthetase activity. The descriptions concerning conservative variants of YBDK and ybdK gene described above can be applied mutatis *mutandis* to variants of γ-glutamylcysteine synthetase and a gene encoding it. The terms "gshA gene" and "GshA protein" include not only the gshA gene and GshA protein exemplified above, but also includes conservative variants thereof, respectively.

The microorganism of the present invention may have been further modified so that the activity of a protein that participates in decomposition of a γ-glutamyl peptide is reduced. Examples of the protein that participates in decomposition of a γ-glutamyl peptide include γ-glutamyltransferase (GGT). By reducing the activity of GGT, decomposition of γ-Glu-Val and γ-Glu-Val-Gly can be suppressed. Examples of GOT include a Ggt protein encoded by a ggt gene. As an example, the nucleotide sequence of the ggt gene of *Escherichia coli* and the amino acid sequence of the protein encoded by the gene are shown in SEQ ID NOS: 25 and 26, respectively. GGT may be a variant of the GGT exemplified above, so long as the variant has the GGT activity. The descriptions concerning conservative variants of YBDK and ybdK gene described above can be applied mutatis *mutandis* to variants of GGT and a gene encoding it. The terms "ggt gene" and "Ggt protein" include not only the ggt gene and Ggt protein exemplified above, but also includes conservative variants thereof, respectively.

Modifications for constructing the microorganism of the present invention can be performed in an arbitrary order.

Hereinafter, methods for reducing the activity of a protein such as YBDK, GSHA, and GGT will be explained.

The expression "the activity of a protein is reduced" means that the activity of the protein is reduced as compared with a non-modified strain. Specifically, the expression "the activity of a protein is reduced" may mean that the activity of the protein per cell is reduced as compared with that of a non-modified strain. The term "non-modified strain" used herein refers to a control strain that has not been modified so that the activity of an objective protein is reduced. Examples of the non-modified strain include a wild-type strain and parent strain. Specific examples of the non-modified strain include the respective type strains of the species of bacteria. Specific examples of the non-modified strain also include strains exemplified above in relation to the description of coryneform bacteria. That is, in an embodiment, the activity of a protein may be reduced ac compared with a type strain. i.e. the type strain of the species to which the microorganism of the present invention belongs. In another embodiment, the activity of a protein may be reduced as compared with the *Escherichia coli* K-12 MG1655 strain. In another embodiment, the activity of a protein may be reduced as compared with the *Escherichia coli* JM109 strain. The state that "the activity of a protein is reduced" also includes a state that the activity of the protein has completely disappeared. More specifically, the expression "the activity of a protein is reduced" may mean that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene (i.e. the amount of mRNA) encoding the protein or the translation amount of the protein (i.e. the amount of the protein). The slate that "the number of molecules of the protein per cell is reduced" also includes a state that the protein does not exist at all. The state that "the function of each molecule of the protein is reduced" also includes a slate that the function of each protein molecule has completely disappeared. The degree of the reduction in the activity of a protein is not particularly limited, so lung as the activity is reduced as compared with that of a non-modified strain. The activity of a protein may be reduced to, for example, 50% or less, 20% or less. 10% or less, 5% or less, or 0% of that of a non-modified strain.

The modification for reducing the activity of a protein can be attained by, for example, reducing the expression of a gene encoding the protein. The expression "the expression of a gene is reduced" means that the expression of the gene is reduced as compared with a non-modified strain. Specifically, the expression "the expression of a gene is reduced" may mean that the expression of the gene per cell is reduced as compared with that of a non-modified strain such as a wild-type strain or parent strain. More specifically, the expression "the expression of a gene is reduced" may mean that the transcription amount of the gene (i.e. the amount of mRNA) is reduced, and/or the translation amount of the gene (i.e. the amount of the protein expressed from the gene) is reduced. The state that "the expression of a gene is reduced" also includes a state that the gene is not expressed at all. The state that "the expression of a gene is reduced" is also referred to as "the expression of a gene is attenuated". The expression ofa gene may be reduced to, for example, 50% or less, 20% or less, 10% or less, 5% or less, or 0% of that of a non-modified strain.

The reduction in gene expression may be due to, for example, a reduction in the transcription efficiency, a reduction in the translation efficiency, or a combination of them. The expression of a gene can be reduced by modifying an expression control sequence of the gene such as a promoter, a Shine-Dalgarno (SD) sequence (also referred to as ribosome-binding site (RBS)), and a spacer region between RBS and the start codon of the gene. When an expression control sequence is modified, preferably one or more nucleotides, more preferably two or more nucleotides, particularly preferably three or more nucleotides, of the expression control sequence are modified. Furthermore, a part or the whole of an expression control sequence may be deleted. The expression of a gene can also be reduced by, for example, manipulating a factor responsible for expression control. Examples of the factor responsible for expression control include low molecules responsible for transcription or translation control (inducers, inhibitors, etc.), proteins responsible for transcription or translation control (transcription factors etc.), nucleic acids responsible for transcription or translation control (siRNA etc.), and so forth. Furthermore, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Furthermore, for example, the gene expression may be reduced due to disruption of a gene as described later.

The modification for reducing the activity of a protein can also be attained by, for example, disrupting a gene encoding the protein. The expression "a gene is disrupted" means that a gene is modified so that a protein that can normally function is not produced. The state that "a protein that normally functions is not produced" includes a state that the protein is not produced at all from the gene, and a slate that the protein of which the function (such as activity or property) per molecule is reduced or eliminated is produced from the gene.

Disruption of a gene can be attained by, for example, deleting a part or the whole of the coding region of the gene on a chromosome. Furthermore, the whole of a gene including sequences upstream and downstream from the gene on a chromosome may be deleted. The region to be deleted may be any region such as an N-terminus region, an internal region, or a C-terminus region, so long as the activity of the protein can be reduced. Deletion of a longer region can usually more surely inactivate the gene. Furthermore, it is preferred that reading frames of the sequences upstream and downstream from the region to be deleted are not the same.

Disruption of a gene can also be attained by, for example, introducing a mutation for an amino acid substitution (missense mutation), a stop codon (nonsense mutation), a frame shift mutation which adds or deletes one or two nucleotide residues, or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another sequence into a coding region of the gene on a chromosome. Site of the insertion may be in any region of the gene, and insertion of a longer region can usually more surely inactivate the gene. It is preferred that reading frames of the sequences upstream and downstream from the insertion site are not the same. The other sequence is not particularly limited so long as a sequence that reduces or eliminates the activity of the encoded protein is chosen, and examples thereof include, for example, a marker gene such as antibiotic resistance genes, and a gene useful for production of an objective substance.

Such modification of a gene on a chromosome as described above can be attained by, for example, preparing a deficient type gene modified so that it is unable to produce a protein that normally functions, and transforming a host with a recombinant DNA containing the deficient type gene to cause homologous recombination between the deficient type gene and the wild-type gene on a chromosome and thereby substitute the deficient type gene for the wild-type gene on the chromosome. In this procedure, if a marker gene selected according to the characteristics of the host such as auxotrophy is included in the recombinant DNA. the operation becomes easier. Examples of the deficient type gene include a gene including deletion of all or a part of the gene, gene including a missense mutation, gene including a nonsense mutation, gene including a frame shift mutation, and gene including insertion of a transposon or marker gene. The protein encoded by the deficient type gene has a conformation different from that of the wild-type protein, even if it is produced, and thus the function thereof is reduced or eliminated. Such gene disruption based on gene substitution utilizing homologous recombination has already been established, and there are methods of using a linear DNA such as a method called "Red driven integration" (Datsenko, K. A, and Wanner, B. L., Proc. Natl. Acad. Sci. USA, 97:6640-6645 (20(0))), and a method utilizing the Red driven integration in combination with an excision system derived from phage (Cho, E. H., Gumport, R. I., Gardner, J. F., J. Bacteriol., 184:5200-5203 (2002)) (refer to WO2005/010175), a method of using a plasmid having a temperature sensitive replication origin, a method of using a plasmid capable of conjugative transfer, a method of utilizing a suicide vector not having a replication origin that functions in a host (U.S. Pat. No. 6,303,383, Japanese Patent Laid-open (Kokai) No. 05-10)7491), and so forth.

Modification for reducing activity of a protein can also be attained by, for example a mutagenesis treatment. Examples of the mutagenesis treatment include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

When a protein functions as a complex consisting of a plurality of subunits, a part or all of the plurality of subunits may be modified, so long as the activity of the protein is eventually reduced. That is, for example, a part or all of a plurality of genes that encode the respective subunits may be disrupted or the like. Furthermore, when there is a plurality of isozymes of a protein, a part or all of the activities of the plurality of isozymes may be reduced, so long as the activity of the protein is eventually reduced. That is, for example, a pan or all of a plurality of genes that encode the respective isozymes may be disrupted or the like.

A reduction in the activity of a protein can be confirmed by measuring the activity of the protein.

A reduction in the activity of a protein can also be confirmed by confirming a reduction in the expression of a gene encoding the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that of a non-modified strain. Examples of the method for evaluating the amount of mRNA include Northern hybridisation, RT PCR, and so forth (Molecular Cloning, Cold Spring Harbor Laboratory Press, Cold Spring Harbor (USA), 2001). The amount of mRNA is preferably reduced to, for example, 50% or less, 20% or less, 10% or less, 5% or less, or 0% of that of a non-modified strain.

A reduction in the amount of a protein can be confirmed by Western blotting using antibodies (Molecular Cloning, Cold Spring Harbor Laboratory Press, Cold Spring Harbor (USA) 2001). The amount of the protein is preferably reduced to, for example, 50% or less, 20% or less, 10% or less, 5% or less, or 0% of that of a non-modified strain.

Disruption of a gene can be confirmed by determining nucleotide sequence of a part or the whole of the gene, restriction enzyme map, full length, or the like of the gene depending on the means used for the disruption.

<2>Production of γ-Glutamylvaline Synthetase (γ-Glu-Val Synthetase)

The microorganism of the present invention can be used as an expression host for γ-glutamylvaline synthetase. That is, the microorganism of the present invention may have a gene encoding γ-glutamylvaline synthetase (also referred to as "γ-glutamylvaline synthetase gene"). Hereinafter, the term "host having a γ-glutamylvaline synthetase gene" refers to the microorganism of the present invention having a γ-glutamylvaline synthetase gene. The expression "having a γ-glutamylvaline synthetase gene" is also expressed as "having γ-glutamylvaline synthetase". That is, for example, a host having a γ-glutamylvaline synthetase gene is also referred to as "host having γ-glutamylvaline synthetase".

The host having a γ-glutamylvaline synthetase gene may be one inherently having the γ-glutamylvaline synthetase gene, or may be one modified so as to have the γ-glutamylvaline synthetase gene. Examples of the host modified so as to have a γ-glutamylvaline synthetase gene include a host introduced with a γ-glutamylvaline synthetase gene. That is, the microorganism of the present invention, for example, may have been introduced with a γ-glutamylvaline synthetase gene. Modifications for constructing the microorganism of the present invention can be performed in an arbitrary order. That is, for example, a bacterium inherently having a γ-glutamylvaline synthetase gene may be modified so that the activity of YBDK is reduced. Alternatively, for example, a bacterium modified so that the activity of YBDK is reduced may be introduced with a γ-glutamylvaline synthetase gene, or a bacterium introduced with a γ-glutamylvaline synthetase gene may be modified so that the activity of YBDK is reduced.

In the present invention, the term "γ-glutamylvaline synthetase" refers to a protein having the γ-glutamylvaline synthetase activity. γ-Glutamylvaline synthetase may have or may not have an activity of generating a γ-glutamyl dipeptide other than γ-glutamylvaline, so long as γ-glutamylvaline synthetase has the γ-glutamylvaline synthetase activity. Thai is, for example, γ-glutamylvaline synthetase may have or may not have the γ-glutamylcysteine synthetase activity. Also, for example, γ-glutamylvaline synthetase may have or may not have the γ-glutamylglycine synthetase activity. It is preferred that γ-glutamylvaline synthetase does not have the γ-glutamylglycine synthetase activity. Methods for measuring the γ-glutamylvaline synthetase activity and the γ-glutamylglycine synthetase activity are as described above. It is sufficient that γ-glutamylvaline synthetase has the γ-glutamylvaline synthetase activity under appropriate conditions. γ-Glutamylvaline synthetase may have the Y glutamylvaline synthetase activity, for example, in the presence of $Mg^2$ or $Mn^{2+}$, or particularly in the presence of $Mg^{2+}$. γ-Glutamylvaline synthetase may have the γ-glutamylvaline synthetase activity, for example, at least at one pH of pH7.0-9.0, or particularly at pH9.0.

It is preferred that the Val-selectivity of γ-glutamylvaline synthetase is higher than that of YBUK. The Val-selectivity of γ-glutamylvaline synthetase may be, for example, 3.1) or higher, 5.0 or higher, 10 or higher, 15 or higher, or 20 or higher. The Val-selectivity of γ-glutamylvaline synthetase may be, for example, 10,000,000 or lower, 1,000,000 or lower, 100,000 or lower, 10,000 or lower, 1,000 or lower, 100 or lower, or 50 or lower. The Val-selectivity of γ-glutamylvaline synthetase may be, for example, within a range defined as a combination thereof. γ-glutamylvaline synthetase may show the Val-selectivity exemplified above under appropriate conditions. γ-Glutamylvaline synthetase may show the Val-selectivity exemplified above, for example, in the presence of $Mg^2$ or $Mn^2$, or particularly in the presence of $Mg^{2+}$. γ-Glutamylvaline synthetase may show the Val-selectivity exemplified above, for example, at least at one pH of pH7.0-9.0, or particularly at pH9.0.

In particular, by using γ-glutamylvaline synthetase showing a high Val-selectivity in combination with glutathione synthetase, it is expected that γ-glutamylvalylglycine can be efficiently produced from Glu, Val, and Gly as raw materials with reduced by-production of γ-glutamylglycine. Also, in particular, by using γ-glutamylvaline synthetase having a high γ-glutamylvaline synthetase activity (specific activity), it is expected that γ-glutamylvaline can be efficiently produced from Glu and Val as raw materials.

Examples of γ-glutamylvaline synthetase include, for example, γ-glutamylvaline synthetases of *Kocuria* bacteria and *Micrococcus* bacteria. Examples of the *Kocuria* bacteria include *Kocuria rosea*, and *Kocuria rhizophila*. Examples of the *Micrococcus* bacteria include *Micrococcus luteus*. That is, γ-glutamylvaline synthetase may be, for example, a protein derived from such bacteria as mentioned above.

The amino acid sequence of γ-glutamylvaline synthetase of *Kocuria rosea* (AJ3132) and the nucleoside sequence of the gene encoding it are shown as SEQ ID NOS: 18 and 17, respectively. The amino acid sequence of γ-glutamylvaline synthetase of the *Kocuria rhizophila* DC2201 strain (ATCC 9341) and the nucleotide sequence of the gene encoding it are shown as SEQ ID NOS: 20 and 19, respectively. The amino acid sequence of γ-glutamylvaline synthetase of the *Micrococcus luteus* NCIC2665 strain (Al CC 15307) and the nucleotide sequence of the gene encoding it are shown as SEQ ID NOS: 22 and 21, respectively. That is. γ-glutamylvaline synthetase may be, for example, a protein having the amino acid sequence of SEQ ID NO: 1$, 20, or 22. Furthermore, γ-glutamylvaline synthetase may be, for example, a protein encoded by a gene having the nucleotide sequence of SEQ ID NO: 17, 19, or 21.

γ-Glutamylvaline synthetase may be a variant of the γ-glutamylvaline synthetases exemplified above (for example, a protein having the amino acid sequence shown as SEQ ID NO: 18, 20, or 22), so long as the variant has the γ-glutamylvaline synthetase activity. Similarly, the γ-glutamylvaline synthetase gene may be a variant of the γ-glutamylvaline synthetase genes exemplified above (for example, a gene having the nucleotide sequence shown as SEQ ID NO: 17, 19, or 21), so long as the variant encodes a protein having the γ-glutamylvaline synthetase activity. The descriptions concerning conservative variants of YBDK and t bdK gene described above can be applied mutatis *mutandis* to variants of γ-glutamylvaline synthetase and a gene encoding it. The expression "the original function is maintained" means that, in the case of γ-glutamylvaline synthetase, a variant of the protein has the γ-glutamylvaline synthetase activity. The enzymatic characteristics of the variant, such as substrate specificity, requirement for divalent metal ions, and pH dependency, each may be or may not be identical to those of the original protein, so long as the variant has the γ-glutamylvaline synthetase activity. For example, the variant may have or may not have an activity of generating a γ-glutamyl dipeptide other than γ-glutamylvaline. Also, the variant may show the Val-selectivity exemplified above.

Examples of γ-glutamylvaline synthetase also include, for example, mutant glutamate-cysteine ligases (mutant GSHAs) disclosed in WO2015/l 15612.

In the present invention, the term "mutant glutamate-cysteine ligase (mutant GSHA)" refers to GSHA having a "specific mutation". In the present invention, a gene encoding a mutant GSHA is also referred to as "mutant glutamate-cysteine ligase gene (mutant gshA gene)". The "specific mutation" will be described later.

In the present invention, a glutamate-cysteine ligase not having the "specific mutation" is also referred to as "wild-type glutamate-cysteine ligase (wild-type GSHA)". In the present invention, a gene encoding a wild-type GSHA is also referred to as "wild-type glutamate-cysteine ligase gene (wild-type gshA gene)". The term "wild-type" is used for convenience for distinguishing the "wild-type" ones from the "mutant" ones, and the wild-type gene or enzyme is not limited to a naturally occurring one, so long as the gene or enzyme does not have the "specific mutation". Examples of the wild-type GSHA include, for example, the GSHAs exemplified above, such as the GshA protein of E. coli. In addition, conservative variants of the GSHAs exemplified above are all included in the wild-type GSHA, so long as the variants do not have the "specific mutation". The wild-type GSHA may typically be a protein having the γ-glutamyl-cysteine synthetase activity. However, in the present invention, so long as the corresponding mutant GSHA has the γ-glutamylvaline synthetase activity, the wild-type GSHA may have the γ-glutamylcysteine synthetase activity, γ-glutamylvaline synthetase activity, γ-glutamylglycine synthetase activity, or an arbitrary combination of these, or may have none of these activities.

The mutant GSHA has the "specific mutation" in the amino acid sequence of the wild-type GSHA. That is, for example, the mutant GSHA may be a protein having the amino acid sequence shown as SEQ ID NO: 24, but including the "specific mutation". The mutant GSHA may also be, for example, a protein having the amino acid sequence shown as SEQ ID NO: 24, but including the "specific mutation", further including substitution, deletion, insertion, or addition of one or several amino acid residues at a site other than that of the "specific mutation", and having the γ-glutamylvaline synthetase activity. In other words, the mutant GSHA may be a protein having an amino acid sequence identical to that of the wild-type OSHA, except that it has the "specific mutation". For example, the mutant GSHA may be a protein having the amino acid sequence shown as SEQ ID NO: 24, except that it has the "specific mutation". The mutant GSHA may also be, for example, a protein having the amino acid sequence shown as SEQ ID NO: 24, but including substitution, deletion, insertion, or addition of one or several amino acid residues, and having the γ-glutamylvaline synthetase activity. except that it has the "specific mutation". The mutant GSHA may also be, for example, a protein having an amino acid sequence showing a homology of 110% or higher, preferably 90% or higher, more preferably 95% or higher, still more preferably 97% or higher, particularly preferably 99% or higher, to the amino acid sequence shown as SEQ ID NO: 24, and having the γ-glutamylvaline synthetase activity, except that it has the "specific mutation".

The "specific mutation" refers to a mutation that imparts a characteristic suitable for generation of γ-glutamylvaline to a wild-type GSHA, when it is introduced into the wild-type GSHA. That is, because of having the "specific mutation", the mutant GSHA has a characteristic suitable for generation of γ-glutamylvaline, compared with the wild-type GSHA. Examples of the characteristic suitable for generation of γ-glutamylvaline include, for example, increased γ-glutamylvaline synthetase activity (specific activity), reduced γ-glutamylglycine synthetase activity (specific activity), increased Val-selectivity, and a combination thereof. For example, the γ-glutamylvaline synthetase activity (specific activity) of the mutant GSHA may increase to for example, 1.1 times or more, 1.5 times or more. 2 times or more. 5 times or more. 14) times or more, or 20 times or more, of that of the wild-type GSHA.

Examples of the "specific mutation" include a mutation corresponding to a mutation at one or more amino acid residues selected from the followings: L135, Q144. Y241, N243, Y300.

In the aforementioned description, the numerals indicate the positions in the amino acid sequence of the wild-type GSHA shown as SEQ ID NO: 24, and the letters on the left side of the numerals indicate the amino acid residues at the respective positions in the amino acid sequence of the wild-type GSHA shown as SEQ ID NO: 24 (namely, the amino acid residues before being mutated, indicated with one-letter code). Fix example, "L135" indicates the Leu residue at position 135 in the amino acid sequence of the wild-type GSHA shown as SEQ ID NO: 24.

As for the aforementioned mutation, the amino acid residues after substitution may be any amino acid residues other than the original amino acid residues, so long as the mutant GSHA has the γ-glutamylvaline synthetase activity. Specific examples of the amino acid residue after the substitution include K (Lys). R (Arg), H (His), A (Ala), V (Val), L (Leu), I (Ile), G (Gly), S (Ser), T (Thr), P (Pro), F (Phe), W (Trp), Y (Tyr), C (Cys), M (Met), D (Asp), E (Glu), N (Asn), and Q (Gin), which should be other than the original amino acid residues.

Specific examples of the "specific mutation" include a mutation corresponding to one or more mutations selected from the followings. That is, the "specific mutation" may include a mutation corresponding to one or more mutations selected from the followings. The "specific mutation" may be, for example, a mutation corresponding to any one of mutation selected from the followings, or may be a mutation corresponding to a combination of two or more mutations selected from the followings. The "specific mutation" may also be, for example, a mutation corresponding to a combination of one or more mutations selected from the followings, and a mutation other than the foregoing mutation at one or more amino acid residues selected from L135, Q144, Y241, N243, and Y300.

L135(I, F, M, V, G, A, W, K, H, R, C, N, S, T),
Q144(F, A, N, S, D, T, R, H, G, K, Y, W, C, M, P, V, L, I),
Y241(A),
N243(I, W, K, R, H),
Y300(A, H, R, K).

In the aforementioned descriptions, the meanings of the numerals and the letters on the left side of the numerals are the same as those described above. The letters in the parentheses on the right side of the numerals indicate the amino acid residues (one-letter code) alter being mutated. Namely, for example, "L I35(1, F, M. V. Q A, W, K. H, R, C, N, S. T)" means a mutation that the Leu residue at position 135 in the amino acid sequence of the wild-type GSHA shown as SEQ ID NO: 24 is replaced with any one of amino acid residues of De, Phe, Met, Val, Gly, Ala, Trp, Lys, His, Arg, Cys, Asn, Ser, and Thr. The amino acid residues after being mutated may also be mentioned without parenthesis. That is, for example, "LI 351" means a mutation that the Leu residue at position 135 in the amino acid sequence of the wild-type GSHA shown as SEQ ID NO: 24 is replaced with an Ile residue.

Combination of the mutations is not particularly limited. Specific examples of combination of the mutations include the following combinations:

L135I/Q144R, L135I/Q144D, L135I/Q144A, L135I/ Q144L, L135I/N243W, L135I/N243F, L135F/Q144A, L135F/N243W, L135M/Q144R, L135M/Q144A, L135M/ Q144L, L135M/N243W, L135M/N243F, L135M/Q 144H, L135M/Q144N, L135M/N243Y, L135M/N243R, L135M/ N243C, L135V/Q144R, L135V/Q144D. L135V/Q144A, L135V/Q144L, L135V/Q144V, L135V/Q144K, L135V/ Q144C, L135V/Q144T, L135H/Q144R, L135G/Q144L, L135A/Q144L, L135V/N243W, LI 35V/N243F, L135V/ N243P, Q144R/N243W, Q144R/N243F, Q144D/N243W, Q144D/N243F. Q144A/N243W, Q144A/N243F, Q144L/ N243W, Q144L/N243F, L135M/Q144F, L135M/N243A. L135V/N243G, L135V/N243A, L135V/N243L, L135V/ N243Y, L135V/N243K, L135V/N243R, L135V/N243H, L135V/N243D, LI 35V/N243E, L135V/N243C, L135V/ N243Q, L135V/N243S, LI 35V/N243T, L135V/Q144I, L135V/Q144P, L135V/Q144W, L135V/Q144H, L135V/ Q144E, L135V/Q144N, L135V/Q144S, L135K/Q144L, L135H/Q144L, L135D/Q144L, L135C/Q144L, L135Q/ Q144L, L135N/Q144L, L135S/Q144L, L135T/Q144L.

In the aforementioned descriptions, the meanings of the numerals and the letters on the left and right sides of the numerals are the same as those described above. In the aforementioned descriptions, two ore more mutations separated with "/" indicate a double or more multiple mutation. That is, for example, "LI 351/Q144R" indicates a double mutation of 11351 and Q144R.

Also, examples of mutations with which a significant increase of the γ-glutamylvaline synthetase activity (specific activity) was observed in the Examples of WO2015/115612 include the following mutations:

L135(I, M, V, G, A, K, H, C, N, S, T),
Q144(F, A, S, D, T, R, H, K, Y, W, C, M, P, V, L, I),
N243(R, H),
Y300(R, K).
L135I/Q144R, L135I/Q144D, L135I/Q144A, L135I/
  Q144L, L135I/N243W, L135I/N243F, L135F/Q144A,
  L135M/Q144R, L135M/Q144A, L135M/Q144L,
  L135M/N243W, L135M/Q144H, L13SM/Q144N,
  L135M/N243C, L135V/Q144R, L135V/Q144D.
  L135V/Q144A, L135V/Q144L, L135V/Q144V.
  L135V/Q144K, L135V/Q144C, L135V/Q144T,
  L135H/Q144R, L135G/Q144L, L135A/Q144L,
  L135V/N243W, L135V/N243F L135V/N243P,
  Q144R/N243W, Q144D/N243W, Q144A/N243W,
  Q144A/N243F, Q144L/N243W, Q144L/N243F,
  L135M/Q144F, L135M/N243A, L135V/N2430,
  L135V/N243A, L135V/N243L, L135V/N243Y,
  L135V/N243K, L135V/N243R, L135V/N243H,
  L135V/N243D, L135V/N243E, L135V/N243C,
  L135V/N243Q, L135V/N243S, L135V/N243T,
  L135V/Q144P, L135V/Q144W, L135V/Q144H,
  L135V/Q144E, L135V/Q144N, L135V/Q144S,
  L135D/Q144L, L135C/Q144L, L135N/Q144L,
  L135S/Q144L, L135T/Q144L.

A "mutation corresponding to a mutation of an amino acid residue at position n in the amino acid sequence shown as SEQ ID NO: 24" in the amino acid sequence of an arbitrary wild-type GSHA means a mutation at an amino acid residue corresponding to the amino acid residue at position n in the amino acid sequence shown as SEQ ID NO: 24. That is, for example, a "mutation corresponding to L135I" indicates a mutation that an amino acid residue corresponding to the Leu residue at position 135 (L135) in the amino acid sequence of wild-type GSHA shown as SEQ ID NO: 24 is replaced with an Ile residue. The "amino acid residue corresponding to L135" mentioned here may typically be a Leu residue, but may not be a Leu residue. Namely, for example, the "mutation corresponding to L135I" is nut limited to a mutation that when the "amino acid residue corresponding to L135" is a Leu residue, the Leu residue is replaced with an Ile residue, but includes a mutation that when the "amino acid residue corresponding to L135" is Lys, Arg, His, Ala, Val, Gly, Ser, Thr, Pro, Phe, Trp, Tyr, Cys, Met, Asp, Glu, Asn, or Gln residue, this amino acid residue is replaced with an Ile residue. The same shall apply to the other mutations.

An "amino acid residue corresponding to the amino acid residue at position n in the amino acid sequence shown as SEQ ID NO: 24" in the amino acid sequence of an arbitrary wild-type GSHA means an amino acid residue corresponding to the amino acid residue at position n in the amino acid sequence shown as SEQ ID NO: 24 in an alignment of the target amino acid sequence of wild-type GSHA and the amino acid sequence of SEQ ID NO: 24. That is, as for the aforementioned mutation, the position of an amino acid residue does not necessarily indicate an absolute position in the amino acid sequence of a wild-type GSHA, but indicates a relative position based on the amino acid sequence shown as SEQ ID NO: 24. For example, when one amino acid residue is deleted at a position on the N-terminus side of position n in the wild-type GSHA consisting of the amino acid sequence shown as SEQ ID NO: 24, the amino acid residue originally at position n becomes an (n−1)th amino acid residue counted from the N-terminus, but it is regarded as the "amino acid residue corresponding to the amino acid residue at position n in the amino acid sequence shown as SEQ ID NO: 24". Similarly, for example, when an amino acid residue at position 100 in the amino acid sequence of a GSHA homologue of a certain microorganism corresponds to position 101 of the amino acid sequence shown as SEQ ID NO: 24, this amino acid residue is the "amino acid residue corresponding to the amino acid residue at position 101 in the amino acid sequence shown as SEQ ID NO: 24" in the GSHA homologue.

Such alignment can be performed by, for example, using known gene analysis software. Specific examples of such software include DNASIS produced by Hitachi Solutions, GENETYX produced by Genetyx, ClustalW opened to the public by DDBJ, and so forth (Elisabeth C. Tyler et al., Computers and Biomedical Research, 24(1), 72-96, 1991; Barton G. J. et al., Journal of Molecular Biology, 198 (2), 327-37, 1987; Thompson J D et al., Nucleic Acid Research, 22 (22), 4673-80, 1994).

γ-Glutamylvaline synthetase may be a fusion protein with another peptide. The "another peptide" is not particularly limited so long as γ-glutamylvaline synthetase has the γ-glutamylvaline synthetase activity. The "another peptide" can be selected as required depending on various conditions such as purpose of use thereof. Examples of the "another peptide" include a peptide tag, signal peptide, and recognition sequence of a protease. The "another peptide" may be bound to, for example, either one or both of the N-terminus and C-terminus of γ-glutamylvaline synthetase. As the "another peptide", one kind of peptide may be used, or two or more kinds of peptides may be used in combination.

Specific examples of the peptide tag include an His tag, FLAG tag, GST tag, Myc tag, MBP (maltose binding protein), CBP (cellulose binding protein), TRX (thioredoxin), GFP (green fluorescent protein), HRP (horseradish peroxidase), ALP (alkaline phosphatase), and Fc region of antibody. Examples of the His tag include 6xHis lag. A peptide tag can be utilized for, for example, detection and purification of the expressed γ-glutamylvaline synthetase.

The signal peptide is not particularly limited, so long as it functions in a host in which γ-glutamylvaline synthetase is expressed. Examples of the signal peptide include a signal peptide that is recognised by the Sec system secretory pathway and a signal peptide recognised by the Tat system secretory pathway. Specific examples of the signal peptide that is recognized by the Tat system secretory pathway include the TorA signal sequence of *E. coli*, the Sufi signal sequence of *E. coli*, the PhoD signal sequence of *Bacillus subtilis*, the LipA signal sequence of *Bacillus subtilis*, and the IMD signal sequence of *Arthrobacter globiformis* (WO2013/118544). A signal peptide can be used for, for example, secretory production of γ-glutamylvaline synthetase. If secretory production of γ-glutamylvaline synthetase is performed by using a signal peptide, the signal peptide may be cleaved at the time of the secretion, and γ-glutamylvaline synthetase not having the signal peptide may be secreted out of the cell.

Specific examples of the recognition sequence of a protease include the recognition sequence of the Factor Xa protease and the recognition sequence of the proTEV protease. The recognition sequence of a protease can be used for, for example, cleavage of the expressed γ-glutamylvaline synthetase. Specifically, for example, when γ-glutamylvaline synthetase is expressed as a fusion protein with a peptide tag, if a recognition sequence of a protease is introduced into the connection part of γ-glutamylvaline synthetase and the peptide tag. the peptide tag can be cleaved from the expressed γ-glutamylvaline synthetase by using a protease to obtain γ-glutamylvaline synthetase not having the peptide tag.

The γ-glutamylvaline synthetase gene may be one having any of the nucleotide sequences of the γ-glutamylvaline synthetase genes exemplified above and conservative variants thereof in which arbitrary codons are replaced with equivalent codons. For example, in the γ-glutamylvaline synthetase gene, codons may be optimized according to codon frequencies observed in the host to be used. Specifically, for example, when the start codon is not ATG, the start codon can be modified to ATG. In addition, the γ-glutamylvaline synthetase gene of *Kocuria rosea* (AJ3132) optimised for expression in *Escherichia coli* is shown as SEQ ID NO: 29.

In the present invention, a "gene" is not limited to DNA, but may include an arbitrary polynucleotide, so long as it encodes a target protein. That is, the term "γ-glutamylvaline synthetase gene" may mean an arbitrary polynucleotide encoding γ-glutamylvaline synthetase. The γ-glutamylvaline synthetase gene may be DNA, RNA, or a combination thereof. The γ-glutamylvaline synthetase gene may be single-stranded or double-stranded. The γ-glutamylvaline synthetase gene may be a single-stranded DNA or a single-stranded RNA. The γ-glutamylvaline synthetase gene may be a double-stranded DNA, a double-stranded RNA. or a hybrid strand consisting of a DNA strand and an RNA strand. The γ-glutamylvaline synthetase gene may contain both a DNA residue and an RNA residue in a single polynucleotide chain. When the γ-glutamylvaline synthetase gene contains RNA, the aforementioned descriptions concerning DNA, such as those concerning nucleotide sequences exemplified above, may be applied to RNA with appropriately changing wordings to those for RNA as required. The mode of the γ-glutamylvaline synthetase gene can be chosen according to various conditions such as use thereof.

A γ-glutamylvaline synthetase gene can be obtained by cloning from an organism having the γ-glutamylvaline synthetase gene. For the cloning, a nucleic acid containing the gene, such as a genomic DNA or cDNA, can be used. A γ-glutamylvaline synthetase gene can also be obtained by chemical synthesis (Gene, 60 (1), 115-127 (1987)).

Furthermore, the obtained γ-glutamylvaline synthetase gene can be modified as required to obtain a variant thereof. Modification of a gene can be performed by a known method. For example, by the site-specific mutagenesis method, an objective mutation can be introduced into a target site of DNA. That is, for example, a coding region of a gene can be modified by the site-specific mutagenesis method so that a specific site of the encoded protein include substitution, deletion, insertion, or addition of amino acid residues. Examples of the site-specific mutagenesis method include a method using PCR (Higuchi, R., 61, in PCR Technology, Erlich, H. A. Eds., Stockton Press, 1989; Caner P., Meth., in Enzymol., 154, 382, 1987), and a method of using a phage (Kramer, W. and Frits, H. J., Meth. in Enzymol., 154, 350, 1987; Kunkel, T. A. et al. Meth. in Enzymol. 154. 367, 1987).

A mutant gshA gene can also be obtained by, for example, modifying a wild-type gshA gene so that the encoded protein has the "specific mutation". The original wild-type gshA gene to be modified can be obtained by, for example, cloning from an organism having the wild-type gshA gene, or chemical synthesis. A mutant gshA gene can also be obtained without using a wild-type gshA gene. For example, a mutant gshA gene may be directly obtained by chemical synthesis etc., or a mutant gshA gene may be further modified to obtain another mutant gshA gene.

The method for introducing a γ-glutamylvaline synthetase gene into a host is not particularly limited. In a host, a γ-glutamylvaline synthetase gene may be harbored in such a manner that it can be expressed under control of a promoter that functions in the host. In the host, the γ-glutamylvaline synthetase gene may exist on a vector autonomously replicable out of the chromosome such as plasmid, or may be introduced into the chromosome. The host may have only one copy of a γ-glutamylvaline synthetase gene, or may have two or more copies of a γ-glutamylvaline synthetase gene. The host may have only one kind of γ-glutamylvaline synthetase gene, or may have two or more kinds of γ-glutamylvaline synthetase genes. Incidentally, the expression "introducing a mutant gshA gene into a host" also includes modifying a gshA gene on the chromosome of the host so as to have the "specific mutation".

The promoter for expressing a γ-glutamylvaline synthetase gene is not particularly limited so long as it is a promoter that functions in the host. The "promoter that functions in a host" refers to a promoter that shows a promoter activity in the host. The promoter may be a promoter derived from the host, or a heterologous promoter. The promoter may be a native promoter of the γ-glutamylvaline synthetase gene. or may be a promoter of another gene. The promoter may be a promoter stronger than the native promoter of the γ-glutamylvaline synthetase gene. Examples of strong promoters that function in Enterobacteriaceae bacteria, such as *Escherichia coli*, include, for example, T7 promoter, trp promoter, trc promoter, lac promoter, lac promoter. lel promoter, araBAD promoter, rpoH promoter, PR promoter, and PL promoter. Examples of strong promoters that function in coryneform bacteria include the artificially modified P54-6 promoter (Appl. Microbial. Biotechnol., 53.674-679 (2000)), pro, aceA, aceB, adh, and amyE promoters inducible in coryneform bacteria with acetic acid, ethanol, pyruvic acid, or the like, cspB, SOD, and luf(EF-Tu) promoters, which are potent promoters capable of providing a large expression amount in coryneform bacteria (Journal of Biotechnology, 104 (2003) 311-323; Appl. Environ. Microbiol., 2005 December; 71 (12):8587-96), as well as lac promoter, lac promoter, and iir promoter. Furthermore, as the stronger promoter, a highly-active type of an existing promoter may also be obtained by using various reporter genes. For example, by making the −35 and −10 regions in a promoter region closer to the consensus sequence, the activity of the promoter can be enhanced (WO(M/18935). Examples of highly active-type promoter include various tac-like promoters (Katashkina J I et al., Russian Federation Patent Application No. 2006134574) and pnlp8 promoter (WO2010/027045). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

Also, a terminator for termination of gene transcription may be located downstream of the γ-glutamylvaline synthetase gene. The terminator is not particularly limited so long as it functions in the bacterium of the present invention. The terminator may be a terminator derived from the host, or a heterogenous terminator. The terminator may be the native terminator of the γ-glutamylvaline synthetase gene, or a terminator of another gene. Specific examples of the terminator include, for example, T7 terminator, T4 terminator, fd phage terminator, let terminator, and lrpA terminator.

A γ-glutamylvaline synthetase gene can be introduced into a host, for example, by using a vector containing the gene. A vector containing a γ-glutamylvaline synthetase gene is also referred to as expression vector or recombinant vector for a γ-glutamylvaline synthetase gene. The expression vector for a γ-glutamylvaline synthetase gene can be constructed by, for example, ligating a DNA fragment containing the γ-glutamylvaline synthetase gene with a vector that functions in the host. By transforming the host with the expression vector for a γ-glutamylvaline synthetase gene, a transformant into which the vector has been introduced is obtained, i.e. the gene can be introduced into the host. As the vector, a vector autonomously replicable in the cell of the host can be used. The vector is preferably a multi-copy vector. Furthermore, the vector preferably has a marker such as an antibiotic resistance gene for selection of transformant. Furthermore, the vector may have a promoter and/or terminator for expressing the introduced gene. The vector may be, for example, a vector derived from a bacterial plasmid, a vector derived from a yeast plasmid, a vector derived from a bacteriophage. cosmid, phagemid, or the like. Specific examples of vector autonomously replicable in Enterobacteriaceae bacteria such as *Escherichia coli* include, for example, pUC19, pUC18, pHSG299, pHSG399, pHSG398, pBR322, pSTV29 (all of these are available from Takara Bio). pACYC184, pMW219 (NIPPON GENE), pTrc99A (Pharmacia), pPROK series vectors (Clontech), pKK233-2 (Clontech), pET series vectors (Novagen), pQE series vectors (QIAGEN), pACYC, and the broad host spectrum vector RSF1010. Specific examples of vector autonomously replicable in coryneform bacteria include, for example, pHM 1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 described in Japanese Patent Laid-open (Kokai) No. 3-210184; plasmids pCRY21, pCRY2KE, pCRY2KX, pCRY31. pCRY3KE. and pCRY3KX described in Japanese Patent Laid-open (Kokai) No. 2-72876 and U.S. Pat. No. 5,185,262; plasmids pCRY2 and pCRY3 described in Japanese Patent Laid-open (Kokai) No. 1-191686; pAJ655. pAJ611, and pAJ1844 described in Japanese Patent Laid-open (Kokai) No. 58-192900; pCG1 described in Japanese Patent Laid-open (Kokai) No. 57-134500; pCG2 described in Japanese Patent Laid-open (Kokai) No. 58-35197; and pCG4 and pCG11 described in Japanese Patent Laid-open (Kokai) No. 57-183799. When the expression vector is constructed, for example, a γ-glutamylvaline synthetase gene having a native promoter region as it is may be incorporated into a vector, a coding region of γ-glutamylvaline synthetase ligated downstream from such a promoter as mentioned above may be incorporated into a vector, or a coding region of γ-glutamylvaline synthetase may be incorporated into a vector downstream from a promoter originally existing in the vector.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

A γ-glutamylvaline synthetase gene can also be introduced into, for example, a chromosome of a host. A gene can be introduced into a chromosome by, for example, using homologous recombination (Miller. J. H., Experiments in Molecular Genetics, 1972, Cold Spring Harbor Laboratory). Examples of the gene transfer method utilising homologous recombination include, for example, a method using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, and a transduction method using a phage. Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome include repetitive DNAs, and inverted repeats located at the both ends of a transposon. Alternatively, homologous recombination may be performed by using an appropriate sequence on a chromosome such as a gene unnecessary for implementing the present invention as a target. Examples of the gene unnecessary for implementing the present invention include, for example, yhdK, gshA, and ggt genes. Furthermore, a gene can also be randomly introduced into a chromosome by using a transposon or Mini-Mu (Japanese Patent Laid-open (Kokai) No. 2-109985, U.S. Pat. No. 5,882,888, EP 805867B1). When the gene is introduced into a chromosome, for example, a γ-glutamylvaline synthetase gene having a native promoter region as it is may be incorporated into a chromosome, a coding region for γ-glutamylvaline synthetase ligated downstream from such a promoter as mentioned above may be incorporated into a chromosome, or a coding region for γ-glutamylvaline synthetase may be incorporated into a chromosome downstream from a promoter originally contained in the chromosome.

Introduction of a gene into a chromosome can be confirmed by, for example, Southern hybridization using a probe having a sequence complementary to a part or the whole of the gene, or PCR using primers prepared on the basis of the nucleotide sequence of the gene.

The method for the transformation is not particularly limited and conventionally known methods can be used. Examples of transformation method include, for example, a method of treating recipient cells with calcium chloride so as to increase the permeability thereof for DNA, which has been reported for the *Escherichia coli* K-12 strain (Mandel, M. and Higa, A., J. Mol. Biol., 1970, 53. 159-162), a method of preparing competent cells from cells which are in the growth phase, followed by transformation with DNA, which has been reported for *Bacillus subtilis* (Duncan, C. H., Wilson, G A. and Young, F. E., Gene, 1977, 1:153-167), and so forth. Furthermore, as the transformation method, there can also be used a method of making DNA-recipient cells into protoplasts or spheroplasts, which can easily take up recombinant DNA, followed by introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-4(X): Hinnen, A., Hicks, J. B. and Fink, G R., 1978, Proc. Natl. Acad. Sci. USA, 75:1929-1933). Furthermore, as the transformation method, the electric pulse method reported for coryneform bacteria (Japanese Patent Laid-open (Kokai) No. 2-207791) can also be used.

Also, a host inherently having a γ-glutamylvaline synthetase gene may have been modified so that the expression of the γ-glutamylvaline synthetase gene is increased. The expression "the expression of a gene is increased" means that the expression of the gene is increased as compared with a non-modified strain. Specifically, the expression "the expression of a gene is increased" may mean that the expression amount of the gene per cell is increased as compared with that of a non-modified strain. The term "non-modified grain" used herein refers to a control strain that has not been modified so that the expression of an objective gene is increased. Examples of the non-modified strain include a wild-type strain and parent strain. Examples of the means for increasing the expression of a γ-glutamylvaline synthetase gene include increasing the copy number of the γ-glutamylvaline synthetase gene, and improving the transcription efficiency or translation efficiency of the γ-glutamylvaline synthetase gene. The copy number of a γ-glutamylvaline synthetase gene can be increased by introducing the γ-glutamylvaline synthetase gene into a host. Introduction of a γ-glutamylvaline synthetase gene can be performed as described above. The γ-glutamylvaline synthetase gene to be introduced may be a gene derived from the host, or heterogenous gene. The transcription efficiency or translation efficiency of a γ-glutamylvaline synthetase gene can be improved by modifying an expression control sequence of the gene, such as promoter, Shine-Dalgarno (SD) sequence (also referred to as ribosome binding site (RBS)), and spacer region between RBS and the start codon. For example, the transcription efficiency of a γ-glutamylvaline synthetase gene can be improved by replacing the promoter of the γ-glutamylvaline synthetase gene with a stronger promoter. As such stronger promoter, the strong promoters mentioned above can be used.

γ-Glutamylvaline synthetase can be produced by making a host having a γ-glutamylvaline synthetase gene express the γ-glutamylvaline synthetase gene. An expression of a γ-glutamylvaline synthetase gene is also referred to as "expression of γ-glutamylvaline synthetase". By culturing a host having a γ-glutamylvaline synthetase gene, γ-glutamylvaline synthetase can be expressed. During the culture, induction of gene expression is performed, if necessary. Conditions for culture of the host and induction of gene expression may be chosen as required depending on various conditions such as type of marker, type of promoter, and type of the host. The medium used for the culture is not be particularly limited, so long as the host can proliferate in the medium and express a γ-glutamylvaline synthetase. As the medium, for example, a usual medium that contains a carbon source, nitrogen source, sulfur source, inorganic ions, and other organic components as required can be used.

Examples of the carbon source include saccharides such as glucose, fructose, sucrose, molasses, and starch hydrolysate, alcohols such as glycerol and ethanol, and organic acids such as fumaric acid, citric acid, and succinic acid.

Examples of the nitrogen source include inorganic ammonium salts such as ammonium sulfate, ammonium chloride, and ammonium phosphate, organic nitrogen such as soybean hydrolysate, ammonia gas, and aqueous ammonia.

Examples of the sulfur source include inorganic sulfur compounds, such as sulfates, sulfites, sulfides, hyposulfites, and thiosulfates.

Examples of the inorganic ions include calcium ion, magnesium ion, manganese ion, potassium ion, iron ion, and phosphoric acid ion.

Examples of the other organic components include organic trace amount nutrients. Examples of the organic trace amount nutrients include required substances such as vitamin $B_1$, yeast extract containing such substances, and so forth.

Culture temperature may be, for example 20 to 45° C. preferably 24 to 45° C. more preferably 30 to 37° C. The culture is preferably performed as aeration culture. In the aeration culture, oxygen concentration may be adjusted to 5 to 50V. preferably about 10%, with respect to the saturated concentration. pH during the culture is preferably 5 to 9. For adjusting pH, inorganic or organic acidic or alkaline substances. such as calcium carbonate, ammonia gas, and aqueous ammonia, can be used.

By performing the culture preferably for about 10 to 120 hours under such conditions as mentioned above, a culture broth containing a γ-glutamylvaline synthetase is obtained. The γ-glutamylvaline synthetase can be accumulated in, for example, microbial cells of the host. Depending on the host to be used and design of the γ-glutamylvaline synthetase gene, it is also possible to accumulate the γ-glutamylvaline synthetase in the periplasm, or to produce the γ-glutamylvaline synthetase out of the cells by secretory production.

The γ-glutamylvaline synthetase may be used in a state that it is contained in microbial cells or the like, or may be separated and purified from microbial cells or the like to be used as a crude enzyme fraction or a purified enzyme, as required. In addition, the γ-glutamylvaline synthetase may be used as a free enzyme, or may be used as an immobilized enzyme immobilized on a solid phase such as a resin.

For example, when the γ-glutamylvaline synthetase is accumulated in microbial cells of the host, by subjecting the cells to disruption, lysis, extraction, etc. as required, the γ-glutamylvaline synthetase can be collected. The microbial cells can be collected from the culture broth by centrifugation or the like. Disruption, lysis, extraction, etc. of the cells can be performed by known methods. Examples of such methods include. for example, disruption by ultrasonication, disruption in Dyno-Mill, disruption in bead mill, disruption with French press. and lysozyme treatment. These methods may be independently used, or may be used in an appropriate combination. Also, for example, when the γ-glutamylvaline synthetase is accumulated in the medium, a culture supernatant can be obtained by centrifugation or the like, and the γ-glutamylvaline synthetase can be collected from the culture supernatant.

The γ-glutamylvaline synthetase can be purified by known methods used for purification of enzymes. Examples of such methods include, for example, ammonium sulfate fractionation, ion exchange chromatography, hydrophobic chromatography, affinity chromatography, gel filtration chromatography, and isoelectric precipitation. These methods may be independently used, or may be used in an appropriate combination. The γ-glutamylvaline synthetase may be purified to a desired extent. For example, when the γ-glutamylvaline synthetase is contaminated with an ingredient that participates in decomposition of γ-glutamyl peptides, such as GGT, it is preferable to remove such an ingredient.

The purified γ-glutamylvaline synthetase can be used as the "γ-glutamylvaline synthetase" used in the methods of the present invention.

Not only the purified γ-glutamylvaline synthetase, but also an arbitrary fraction containing a γ-glutamylvaline synthetase may be used as the "γ-glutamylvaline synthetase" in the methods of the present invention. That is, the "γ-glutamylvaline synthetase" in the methods of the present invention may be an enzyme contained in such a fraction. Such a fraction containing a γ-glutamylvaline synthetase is not particularly limited, so long as it contains a γ-glutamylvaline synthetase so that the γ-glutamylvaline synthetase can act on Glu and Val. Examples of such a fraction include, for example, a culture broth of a host having a γ-glutamylvaline synthetase gene (host having a γ-glutamylvaline synthetase), microbial cells collected from such a culture broth (cultured microbial cells), processed products of such microbial cells such as disruption product of the cells, lysate of the cells, extract of the cells (cell-free extract), and immobilized cells obtained by immobilizing such cells as mentioned above on a carrier such as acrylamide and carrageenan. culture supernatant collected from such a culture broth. partially purified products of these (roughly purified products), and combinations of these. These fractions each may be used alone, or may be used together with a purified γ-glutamylvaline synthetase.

<3>Glutathione Synthetase and Production Thereof

"Glutathione synthetase" is generally known as an enzyme having the activity for catalyzing the reaction of generating glutathione (γ-Glu-Cys-Gly), ADP, and phosphate by using γ-Glu-Cys, Gly. and ATP as the substrates (EC 6.3.2.3). This activity is also referred to as "glutathione synthetase activity".

Furthermore, the activity for catalyzing the reaction of generating γ-Glu-Val-Gly, ADP, and phosphate using γ-Glu-Val, Gly, and ATP as substrates is also referred to as "γ-glutamylvalylglycine synthetase activity" or "γ-Glu-Val-Gly generating (synthetic) activity".

In the present invention, as glutathione synthetase, one having the γ-glutamylvalylglycine synthetase activity is used. That is, in the present invention, the term "glutathione synthetase" refers to a protein having the γ-glutamylvalylglycine synthetase activity.

In the present invention, so long as glutathione synthetase has the γ-glutamylvalylglycine synthetase activity, it may or may not have an activity for generating a γ-glutamyl tripeptide other than γ-glutamylvalylglycine. That is, for example, glutathione synthetase may or may not have the glutathione synthetase activity.

The γ-glutamylvalylglycine synthetase activity of glutathione synthetase can be measured by, for example, using an appropriate amount of glutathione synthetase with a reaction mixture composition of 12.5 mM γ-Glu-Val, 12.5 mM Gly, 12.5 mM ATP, 12.5 mM $MgSO_4$, 2 mM dithiothreitol, 1110 mM Tris-HCl buffer (pH 8.0) at a reaction temperature of 37° C. for a reaction time of from 1 minute to 50 hours. The enzymatic activity for generating 1 μmol of γ-Glu-Val-Gly in 1 minute under the aforementioned conditions is defined as 1 U of the γ-glutamylvalylglycine synthetase activity.

Examples of glutathione synthetase include a GshB protein encoded by a gshB gene and a Gsh2 protein encoded by a GSH2 gene. Examples of the gshB gene include gshB genes of Escherichia bacteria such as Escherichia coli. Examples of the GSH2 gene include GSH2 genes of Saccharomyces yeasts such as Saccharomyces cerevisiae. Examples of glutathione synthetase also include the mutant glutathione synthetase described in WO2013/054447. The nucleotide sequence of the gshB gene of the Escherichia coli K-12 MG1655 strain corresponds to the sequence of the positions 3,089,900 to 3,00,850 in the genome sequence registered at the NCB database as GenBank accession NC 100913.3. The nucleotide sequence of the OH gene of the MG1655 strain (identical to that of the Escherichia coli K-12 W3110 strain) is shown as SEQ ID NO: 27. The amino acid sequence of the protein encoded by this gene is shown as SEQ ID NO: 28. That is, glutathione synthetase may be, for example, a protein encoded by a gene having the nucleotide sequence shown as SEQ ID NO: 27. Glutathione synthetase may also be, for example, a protein having the amino acid sequence shown as SEQ ID NO: 28. Glutathione synthetase may also be a variant of the aforementioned glutathione synthetase, so long as it has the γ-glutamylvalylglycine synthetase activity. The descriptions concerning conservative variants of YBDK and ybdK gene described above can be applied mutatis mutandis to variants of glutathione synthetase and a gene encoding it. The terms "gshB gene" and "GshB protein" include not only the gshB gene and GshB protein exemplified above, but also includes conservative variants thereof, respectively. The terms "GSH2 gene" and "Gsh2 protein" include not only the GSH2 gene and Gsh2 protein exemplified above, but also includes conservative variants thereof, respectively. Glutathione synthetase may also be a fusion protein with another peptide. To such a fusion protein, the aforementioned descriptions concerning fusion protein of γ-glutamylvaline synthetase can be applied mutatis mutandis.

Glutathione synthetase can be produced by making a host having a gene encoding glutathione synthetase (also referred to as "glutathione synthetase gene") express the glutathione synthetase gene. The expression "having a glutathione synthetase gene" is also expressed as "having glutathione synthetase". That is, for example, a host having a glutathione synthetase gene is also referred to as "host having glutathione synthetase". An expression of a glutathione synthetase gene is also referred to as "expression of glutathione synthetase". The host having a glutathione synthetase gene may be one inherently having the glutathione synthetase gene, or one modified so as to have the glutathione synthetase gene. Examples of such a host inherently having a glutathione synthetase gene include such microorganisms as the Escherichia coli having the gshB gene, and Saccharomyces cerevisiae having the GSH2 gene mentioned above. Examples of such a host modified so as to have a glutathione synthetase gene include a host into which the glutathione synthetase gene has been introduced. The host to be introduced with a glutathione synthetase gene is not particularly limited so long as it can express a functional glutathione synthetase. Examples of the host include, for example, bacteria, actinomycetes, yeast, fungi, plant cells, insect cells, and animal cells. Preferred examples of the host include microorganisms such as bacteria and yeast. Examples of the bacteria include, for example, bacteria belonging to the family Enterobacteriaceae, such as Escherichia bacteria, Enterobacter bacteria, and Pantoea bacteria; coryneform bacteria such as *Corynebacterium* bacteria; and *Bacillus* bacteria. As the host, in particular, *Escherichia coli* can be preferably used. Also, a host inherently having a glutathione synthetase gene may have been modified so that the expression of a glutathione synthetase gene is increased. To the modification of a host, such as introduction of a glutathione synthetase gene, the aforementioned descriptions concerning the modification of a host, such as introduction of a γ-glutamylvaline synthetase gene, can be applied mutatis *mutandis*. Materials to be used for modification of the host, such as vector and promoter, can be appropriately chosen according to the type of the host. The host for expressing a glutathione synthetase gene may have been modified so that the activity of YBDK is reduced. Furthermore, the host for expressing a glutathione synthetase gene may have been modified so that the activity of γ-glutamylcysteine synthetase is reduced. Furthermore, the host for expressing a glutathione synthetase gene may have been modified so that the activity of a protein that participates in decomposition of γ-glutamyl peptides, such as γ-glutamyltransferase (GGT), is reduced.

The microorganism of the present invention may also be used as an expression host for glutathione synthetase. That is, the microorganism of the present invention may have a glutathione synthetase gene. Furthermore, the microorganism of the present invention may have both a γ-glutamylvaline synthetase gene and a glutathione synthetase gene.

Glutathione synthetase can also be produced by expressing a glutathione synthetase gene in a cell-free protein synthesis system.

To the production of glutathione synthetase using a host having the glutathione synthetase gene, the aforementioned descriptions concerning production of γ-glutamylvaline synthetase using a host having a γ-glutamylvaline synthetase gene can be applied mutatis *mutandis*. The term "microbial cell" may be appropriately read as "cell" depending on the type of the host. The produced glutathione synthetase (such as a purified glutathione synthetase and a fraction containing glutathione synthetase) can be used as "glutathione synthetase" in the methods of the present invention. Glutathione synthetase may be independently produced, or may be produced together with γ-glutamylvaline synthetase. That is, when the microorganism of the present invention has both a glutathione synthetase gene and a γ-glutamylvaline synthetase gene, glutathione synthetase and γ-glutamylvaline synthetase can be produced together by making the microorganism of the present invention express these genes.

<4>Method for Producing γ-Glutamylvalylglycine (γ-Glu-Val-Gly)

The present invention provides a method for producing γ-Glu-Val using γ-glutamylvaline synthetase, and a method for producing γ-Glu-Val-Gly (CAS 3β837-70-6; also referred to as "Gluvalicine") using γ-glutamylvaline synthetase. These methods are also collectively referred to as the "methods of the present invention". The structural formula of γ-Glu-Val-Gly is shown in Formula (I) below.

<Formula (I)>

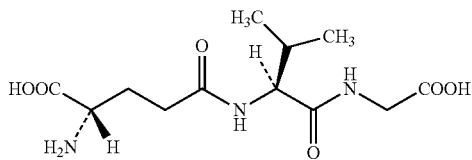

<4-1>Enzymatic method

The present invention provides a method for enzymatically producing γ-Glu-Val-Gly by using γ-glutamylvaline synthetase. This method is also referred to as the "method for producing γ-Glu-Val-Gly of the present invention (enzymatic method)".

In the present invention, Glu and Val can be reacted to generate γ-Glu-Val by using a γ-glutamylvaline synthetase. That is, the present invention provides a method for producing γ-Glu-Val, which comprises (A) a step of allowing a γ-glutamylvaline synthetase to act on Glu and Val to generate γ-Glu-Val. This method is also referred to as the "method for producing γ-Glu-Val of the present invention (enzymatic method)". The generated γ-Glu-Val can be collected from the reaction mixture, as required.

Furthermore, by using the generated γ-Glu-Val as a raw material, γ-Glu-Val-Gly can be produced. As a method for producing γ-Glu-Val-Gly by using γ-Glu-Val as a raw material, the method of using glutathione synthetase is known (Japanese Patent Laid-open (Kokai) No. 2012-15637). Specifically, γ-Glu-Val and Gly can be reacted to generate γ-Glu-Val-Gly by using glutathione synthetase. That is, an embodiment of the method for producing γ-Glu-Val-Gly of the present invention (enzymatic method) (also referred to as the "first embodiment") is a method for producing γ-Glu-Val-Gly, which comprises (A) a step of allowing γ-glutamylvaline synthetase to act on Glu and Val to generate γ-Glu-Val, and (B) a step of allowing glutathione synthetase to act on γ-Glu-Val generated in the step (A) and Gly to generate γ-Glu-Val-Gly.

In the first embodiment, the step (A) and the step (B) may be carried out separately, or may be carried out simultaneously during a partial period or the whole period of the steps. That is, for example, the step (A) and the step (B) may be started simultaneously, or the step (B) may be started while the step (A) is in progress or after the step (A) is completed. The step (A) and the step (B) can be simultaneously started by making γ-glutamylvaline synthetase, glutathione synthetase, Glu, Val, and Gly coexist in a reaction system at the time of the start of the reaction. Alternatively, the step (A) can be started under the conditions that glutathione synthetase and/or Gly does not coexist in the reaction system, and the step (B) can be started by making glutathione synthetase and/or Gly coexist in the reaction system while the step (A) is in progress or after the step (A) is completed. Furthermore, γ-Glu-Val generated in the step (A) may be collected, and the step (B) may be carried out by using the collected γ-Glu-Val. γ-Glu-Val may be subjected to such a treatment as purification, dilution, concentration, drying, and dissolution, as required, and then used for the step (B).

The step (A) of the method for producing γ-Glu-Val of the present invention (enzymatic method) can be carried out, for example, in the same manner as that for carrying out the step (A) of the first embodiment alone.

Also, in the present invention, Glu, Val, and Gly can be reacted to generate γ-Glu-Val-Gly by using γ-glutamylvaline synthetase and glutathione synthetase. That is, another embodiment of the method for producing γ-Glu-Val-Gly of the present invention (enzymatic method) (it is also referred to as the "second embodiment") is a method for producing γ-Glu-Val-Gly, which comprises (C) a step of allowing γ-glutamylvaline synthetase and glutathione synthetase to act on Glu, Val, and Gly to generate γ-Glu-Val-Gly. In the second embodiment, by making γ-glutamylvaline synthetase, glutathione synthetase, Glu, Val, and Gly coexist in a reaction system, γ-glutamylvaline synthetase and glutathione synthetase can be made to act on all of Glu, Val, and Gly to produce γ-Glu-Val-Gly.

In the methods of the present invention, γ-glutamylvaline synthetase and glutathione synthetase are also collectively referred to as "enzymes". Glu, Val, and Gly are also collectively referred to as "amino acids". γ-Glu-Val and γ-Glu-Val-Gly are also collectively referred to as "peptides". Glu, Val, Gly, and γ-Glu-Val are also collectively referred to as "substrates". The "substrates" may further include ATP, unless otherwise stated. A reaction of an enzyme and a substrate corresponding to the enzyme is also referred to as "enzymatic reaction". In the enzymatic method, the term "γ-glutamylvaline synthetase" refers to γ-glutamylvaline synthetase obtained by using the microorganism of the present invention as an expression host.

The mode of the enzymes used for the methods of the present invention is as described above. That is, as each enzyme, for example, a purified enzyme, an arbitrary fraction containing the enzyme, or a combination of these can be used. As each enzyme, one kind of enzyme may be used, or two or more kinds of enzymes may be used in combination.

As each of the amino acids, a commercial product may be used, or one appropriately prepared and obtained may be used. The methods for producing an amino acid are not particularly limited, and, for example, known methods can be used. An amino acid can be produced by, for example, chemical synthesis, enzymatic reaction, or a combination of them. An amino acid can be produced by, for example, culturing a microorganism having an ability to produce the amino acid, and collecting the amino acid from culture. As a microorganism having an ability to produce an amino acid, for example, such amino acid-producing bacteria as described later can be used. An amino acid can also be produced by, for example, collecting the amino acid from agricultural, aquatic, and livestock products containing the amino acid. As each of the amino acids, a purified product purified to a desired extent may be used, or a material containing the amino acid may be used. Such a material containing an amino acid is not particularly limited so long as it contains an amino acid in such a manner that an enzyme can act on the amino acid. Specific examples of the material containing an amino acid include, for example, a culture broth obtained by culturing a microorganism having an ability to produce the amino acid, culture supernatant separated from the culture broth, cells separated from the culture broth, and processed products thereof such as concentrates (concentrated liquids) thereof and concentrated and dried products thereof.

In the methods of the present invention, the amino acids and peptides each may be a free compound, salt thereof, or mixture of them, unless otherwise stated. That is, the term "amino acid" may mean amino acid in the form of free compound, salt thereof or mixture of them, unless otherwise stated. The term "peptide" may mean peptide in the form of free compound, salt thereof, or mixture of them, unless otherwise staled. The salt is not particularly limited so long as it is a chemically acceptable salt. When the produced γ-Glu-Val-Gly is used for oral use (for example, use as an additive for foods and drinks), the salt of γ-Glu-Val-Gly is not particularly limited so long as it is a chemically acceptable edible salt. Specific examples of the "chemically acceptable edible salt" include, for acidic groups such as carboxyl group, for example, ammonium salts, salts with alkali metals such as sodium and potassium, salts with alkaline earth metals such as calcium and magnesium, aluminum salts, zinc salts, salts with organic amines such as triethylamine, ethanolamine, morpholine, pyrrolidine, piperidine, piperazine, and dicyclohexylamine, and salts with basic amino acids such as arginine and lysine. Specific examples of the "chemically acceptable edible salt" include, for basic groups, for example, salts with inorganic acids such as hydrochloric acid, sulfuric acid, phosphoric acid, nitric acid, and hydrobromic acid, salts with organic carboxylic acids such as acetic acid, citric acid, benzoic acid, maleic acid, fumaric acid, tartaric acid, succinic acid, tannic acid, butyric acid, hibenzic acid, pamoic acid, enanthic acid, decanoic acid, teoclic acid, salicylic acid, lactic acid, oxalic acid, mandelic acid, and malic acid, and salts with organic sulfonic acid such as methanesulfonic acid, benzenesulfonic acid, and p-toluenesulfonic acid. As the salt, one kind of salt may be used, or two or more kinds of salts may be used in combination.

The enzymatic reaction can be attained by making the enzyme and the substrates coexist in a reaction mixture. That is, the enzymatic reaction can be carried out in an appropriate reaction mixture. The enzymatic reaction may be carried out by the batch method or the column method. When the batch method is used, the enzymatic reaction can be carried out by mixing the enzyme and the substrates in a reaction mixture contained in a reaction vessel. The enzymatic reaction may be carried out in a stationary slate, or with stirring or shaking. When the column method is used, the enzymatic reaction can be carried out by passing a reaction mixture containing the substrates thorough a column filled with immobilized cells or immobilized enzyme. As the reaction mixture, water, buffer, or the like containing required ingredients can be used. The reaction mixture may contain, for example, the enzyme(s), substrates, ATP, and divalent metal ions. Combination of the ingredients used for the enzymatic reaction can be appropriately chosen according to type and implementation scheme of the step to be carried out, such as whether two or more of steps are simultaneously carried out or not.

Both γ-glutamylvaline synthetase and glutathione synthetase use ATP for the enzymatic reaction. Therefore, ATP is supplied to the reaction system as required. That is, the reaction system (reaction mixture) may contain ATP. All of the aforementioned steps (A) to (C) can be carried out in the presence of ATP. The method for supplying ATP is not particularly limited so long as ATP can be used for the enzymatic reaction. ATP can be added to the reaction mixture in an arbitrary form, for example, in the form of powder or aqueous solution. ATP may also be supplied to the reaction system by, for example, a method for generating or regenerating ATP. As the method for generating or regenerating ATP, there are known the method of supplying ATP from a carbon source by using a *Corynebacterium* bacterium (Hori, H. et al., Appl. Microbiol. Biotechnol., 4K(6):693-69K (1997)), the method of regenerating ATP by using yeast cells and glucose (Yamamoto, S el al., Biosci. Biotechnol. Biochem., 69(4):784-789 (2005)), the method of regenerating ATP using phosphoenolpyruvic acid and pyruvate kinase (C. Aug'e and Ch. Gautheron, Tetrahedron Lett., 29:789-79(1 (1988)), the method of regenerating ATP by using polyphosphoric acid and polyphosphate kinase (Murata, K. et al., Agric. Biol. Chem., 52(6):147I-1477 (1988)), and so forth.

Also, for example, γ-glutamylvaline synthetase typically requires a divalent metal ion for the enzymatic reaction. Therefore, the reaction system (reaction mixture) may contain a divalent metal ion. All of the steps (A) to (C) can be carried out in the presence of a divalent metal ion. The divalent metal ion is not particularly limited so long as the γ-glutamylvaline synthetase activity is obtained. Examples of the divalent metal ion include $Mg^2$ and $Mn^{2+}$ and preferred examples of the divalent metal ion include $Mg^{2+}$. The concentration of the divalent metal ion may be, for example, 1 to 2011 mM.

Reaction conditions (pH of the reaction mixture, reaction temperature, reaction time, concentrations of various ingredients such as substrates and enzyme, etc.) are not particularly limited so long as γ-Glu-Val-Gly is generated.

pH of the reaction mixture may be, for example, usually 6.0 to 10.1), preferably 6.5 to 9.0.

The reaction temperature may be, for example, usually 15 to 50° C., preferably 15 to 45° C. more preferably 20 to 40° C.

The reaction time may be, for example, 5 minutes to 2(X) hours for each of the steps (A) and (13) of the first embodiment. The reaction time may be, for example, 5 minutes to 200 hours for the step (C) of the second embodiment. Flow rate of the reaction mixture may be, for example, such a rate that the reaction time should be within the range of the reaction time exemplified above.

The concentration of each of the substrates in the reaction mixture may be, for example, usually 0.1 to 20(X) mM, preferably 1 to 20(10 mM, more preferably 10 to 10(10 mM.

Molar ratio of the substrates in the reaction mixture for the step (A) of the first embodiment may be set so that, for example, usually, Glu:Val:ATP is 1:1:1. and ratio of an arbitrary substrate may be changed within the range of 0.1 to 10. That is, for example, Glu:Val:ATP may be (1.1 to 10:0.1 to 10:0.1 to 10. As for the step (B) of the first embodiment, the molar ratio of the substrates in the reaction mixture may be set so that, for example, usually, γ-Glu-Val:Gly:ATP is 1:1:1, and ratio of an arbitrary substrate may be changed within the range of 0.1 to 10. That is, for example, γ-Glu-Val:Gly:ATP may be 0.1 to 10:0.1 10 10:0.1 to 10. Molar ratio of the substrates in the reaction mixture for the step (C) of the second embodiment may be set so that, for example, usually, Glu:Val:Gly:ATP is 1:1:1:2, ratio of an arbitrary substrate may be changed within the range 010.1 to 10, and ratio of ATP may be changed within the range 010.2 to 20. That is, for example, Glu:Val:Gly:ATP may be 0.1 to 10:0.1 to 10:0.1 to 10:0.2 to 20. When the step (A) and the step (B) are simultaneously carried out in the first embodiment, molar ratio of the substrates in the first embodiment may be determined with reference to the molar ratio of the substrates for the second embodiment, as required.

The amount of the enzyme to be used can be set on the basis of, for example, enzymatic activity. The amount of γ-glutamylvaline synthetase to be used may be, for example, usually 0.01 to 1001) U, preferably 0.1 to 500 U. more preferably 0.1 to 1110 U, in terms of the γ-Glu-Val generating activity, with respect to 1 mmol of the total amount of Glu and Val. The term "γ-Gin-Val generating activity" referred to herein may refer to the γ-Glu-Val generating activity measured under appropriate conditions, for example, in the presence of $Mg^2$ or $Mn^2$, or particularly in the presence of $Mg^{2+}$, at pH7.0-9.0, or particularly at pH9.0. As for the step (B) of the first embodiment, the amount of glutathione synthetase to be used may be, for example, usually 0.01 to 1000 U, preferably 0.1 to 500 U. more preferably 9.1 to 1011 U, in terms of the γ-Glu-Val-Gly generating activity, with respect to 1 mmol of the total amount of γ-Glu-Val and Gly. As for the step (C) of the second embodiment, the amount of glutathione synthetase to be used may be, for example, usually 0.01 to 11100 U, preferably 0.1 to 50(1 U. more preferably 0.1 to 100 U, in terms of the γ-Glu-Val-Gly generating activity, with respect to 1 mmol of the total amount of a half of the amount of Glu, a half of the amount of Val, and the whole amount of Gly. When the step (A) and the step (B) are simultaneously carried out in the first embodiment, the amount of glutathione synthetase to be used in the first embodiment may be determined with reference to the amount of glutathione synthetase to be used in the second embodiment, as required.

In any of the embodiments, in the course of the enzymatic reaction, the substrates, enzymes, and/or other ingredients may be additionally added to the reaction system independently or in an arbitrary combination. These ingredients may be added at one Lime, or two or more times, or they may be continuously added. The reaction conditions may be constant from the start to the end of the enzymatic reaction, or may change in the course of the enzymatic reaction. The expression "the reaction conditions change in the course of the enzymatic reaction" is not limited to cases where the reaction conditions temporally change, but also includes cases where the reaction conditions spatially change. The expression that "the reaction conditions spatially change" means that, for example, when the enzymatic reaction is performed by the column method, the reaction conditions such as reaction temperature and enzyme concentration are different depending on the position on the flowing pathway.

By carrying out the enzymatic reaction as described above, a reaction mixture containing γ-Glu-Val-Gly can be obtained. Generation of γ-Glu-Val-Gly can be confirmed by a known technique used for detection or identification of a compound. Examples of such a technique include, for example, HPLC. LC/MS, GC/MS, and NMR. These techniques may be independently used, or may be used in an appropriate combination. γ-Glu-Val-Gly can be collected from the reaction mixture as required. γ-Glu-Val-Gly can be collected by a known technique used for separation and purification of a compound. Examples of such a technique include, for example, various chromatography techniques such as ion exchange chromatography, reverse phase high performance liquid chromatography, and affinity chromatography, as well as crystallization and recrystallization from a solution. These techniques may be independently used, or may be used in an appropriate combination. The collected γ-Glu-Val-Gly may contain ingredients other than γ-Glu-Val-Gly, such as ingredients used for the production of γ-Glu-Val-Gly and moisture. γ-Glu-Val-Gly may be purified to a desired extent. γ-Glu-Val-Gly may be purified to a purity of, for example, 30% (w/w) or higher, 50% (w/w) or higher, 70% (w/w) or higher, 80% (w/w) or higher, 90% (w/w) or higher, or 95% (w/w) or higher. γ-Glu-Val can be collected in a manner similar to that for the collection of γ-Glu-Val-Gly.

<4-2>Fermentative method

The present invention provides a method for producing γ-Glu-Val-Gly by fermentation using γ-glutamylvaline synthetase. Specifically, the present invention provides a method for producing γ-Glu-Val-Gly by fermentation using a microorganism having γ-glutamylvaline synthetase. This method is also referred to as the "method for producing γ-Glu-Val-Gly of the present invention (fermentative method)".

In the present invention, γ-Glu-Val can be produced from Glu and Val by fermentation by using a microorganism having γ-glutamylvaline synthetase. That is, the present invention provides a method for producing γ-Glu-Val, which comprises (A) a step of generating γ-Glu-Val from Glu and Val by culturing a microorganism having γ-glutamylvaline synthetase in a medium. This method is also referred to as the "method for producing γ-Glu-Val of the present invention (fermentative method)". The generated γ-Glu-Val can be collected from the culture as required.

Furthermore. γ-Glu-Val-Gly can be produced by fermentation from γ-Glu-Val and Gly by using a microorganism having glutathione synthetase. That is, an embodiment of the method for producing γ-Glu-Val-Gly of the present invention (fermentative method) (also referred to as "third embodiment") is a method for producing γ-Glu-Val-Gly, which comprises (A) a step of generating γ-Glu-Val from Glu and Val by culturing a microorganism having γ-glutamylvaline synthetase in a medium, and (B) a step of generating γ-Glu-Val-Gly from γ-Glu-Val generated in the step (A) and Gly by culturing a microorganism having glutathione synthetase in a medium.

In the third embodiment, the step (A) and the step (B) may be carried out separately, or may be carried simultaneously during a partial period or the whole period of the steps. That is, for example, the step (A) and the step (B) may be started simultaneously, or the step (B) may be started while the step (A) is in progress or after the step (A) is completed. In the third embodiment, the step (A) and the step (B) may be carried out by using a microorganism having γ-glutamylvaline synthetase and another microorganism having glutathione synthetase, or may be carried out by using a single kind of microorganism having both γ-glutamylvaline synthetase and glutathione synthetase. For example, if a microorganism having both γ-glutamylvaline synthetase and glutathione synthetase is used and it is cultured in a state that Glu, Val, and Gly are available, the step (A) and the step (B) can be simultaneously carried out. Furthermore. γ-Glu-Val generated in the step (A) may be collected, and added to a medium to carry out the step (B). γ-Glu-Val may be subjected to such a treatment as purification, dilution, concentration, drying, and dissolution, as required, and then used for the step (B).

The step (A) of the method for producing γ-Glu-Val of the present invention (fermentative method) can be carried out, for example, in the same manner as that for carrying out the step (A) of the third embodiment alone.

Also, in the present invention, γ-Glu-Val-Gly can be produced by fermentation from Glu, Val, and Gly by using a microorganism having both γ-glutamylvaline synthetase and glutathione synthetase. That is, another embodiment of the method for producing γ-Glu-Val-Gly of the present invention (fermentative method) (also referred to as "fourth embodiment") is a method for producing γ-Glu-Val-Gly, which comprises (C) a step of generating γ-Glu-Val-Gly from Glu, Val, and Gly by culturing a microorganism having γ-glutamylvaline synthetase and glutathione synthetase in a medium.

In the fermentative method, such terms as enzymes, amino acids, peptides, substrates, and enzymatic reaction are used in the same meanings as those used for the enzymatic method. A microorganism having γ-glutamylvaline synthetase, microorganism having glutathione synthetase, and microorganism having γ-glutamylvaline synthetase and glutathione synthetase are also generically referred to as "microorganisms". In the fermentative method, the term "microorganism having γ-glutamylvaline synthetase" refers to the microorganism of the present invention having γ-glutamylvaline synthetase. Also, in the fermentative method, the term "microorganism having both γ-glutamylvaline synthetase and glutathione synthetase" refers to the microorganism of the present invention having both γ-glutamylvaline synthetase and glutathione synthetase.

The method for supplying amino acids used as the substrates is not particularly limited so long as the amino acids can be used for the enzymatic reaction. For example, the amino acids each may be biosynthesized by a microorganism used in the corresponding step, may be added to the medium, or may be supplied by a combination of the foregoing means. That is, for example, all of Glu, Val, and Gly may be biosynthesized by a microorganism, or all of Glu, Val, and Gly may be added to the medium. Alternatively, for example, one or two kinds of amino acids among Glu, Val, and Gly may be biosynthesized by a microorganism, and the other amino acid(s) may be added to the medium. All of Glu, Val, and Gly may also be biosynthesized by a microorganism, and added to the medium.

That is, an embodiment of the method for producing γ-Glu-Val of the present invention (fermentative method) may be, for example, a method for producing γ-Glu-Val, which comprises (A1) a step of generating γ-Glu-Val by culturing a microorganism having γ-glutamylvaline synthetase in a medium containing Glu and Val, or a method for producing γ-Glu-Val, which comprises (A2) a step of generating γ-Glu-Val by culturing a microorganism having γ-glutamylvaline synthetase and having an ability to produce Glu and Val in a medium.

Also, an embodiment of the third embodiment may be, for example, a method for producing γ-Glu-Val-Gly, which comprises the step of (A1) or (A2), and the step of (B1) or (B2):

(A1) a step of generating γ-Glu-Val by culturing a microorganism having γ-glutamylvaline synthetase in a medium containing Glu and Val;

(A2) a step of generating γ-Glu-Val by culturing a microorganism having γ-glutamylvaline synthetase and having an ability to produce Glu and Val in a medium;

(B1) a step of generating γ-Glu-Val-Gly by culturing a microorganism having glutathione synthetase in a medium containing γ-Glu-Val generated in the step (A1) or (A2), and Gly;

(B2) a step of generating γ-Glu-Val-Gly by culturing a microorganism having glutathione synthetase and having an ability to produce Gly in a medium containing γ-Glu-Val generated in the step (A1) or (A2).

Furthermore, an embodiment of the fourth embodiment may be, for example, a method for producing γ-Glu-Val-Gly, which comprises (C1) a step of generating γ-Glu-Val-Gly by culturing a microorganism having γ-glutamylvaline synthetase and glutathione synthetase in a medium containing Glu. Val, and Gly, or a method for producing γ-Glu-Val-Gly, which comprises (C2) a step of generating γ-Glu-Val-Gly by culturing a microorganism having γ-glutamylvaline synthetase and glutathione synthetase and having an ability to produce Glu, Val, and Gly in a medium.

As the microorganism having γ-glutamylvaline synthetase, the microorganism of the present invention mentioned above and having a γ-glutamylvaline synthetase gene can be used as it is, or alter modification as required. As the microorganism having glutathione synthetase, such a microorganism having a glutathione synthetase gene as mentioned above can be used as it is, or after modification as required. As the microorganism having γ-glutamylvaline synthetase and glutathione synthetase, the microorganism of the present invention mentioned above and having both a γ-glutamylvaline synthetase gene and a glutathione synthetase gene can be used as it is, or after modification as required.

The microorganism having an ability to produce an amino acid may be one inherently having the ability to produce an amino acid, or may be one modified to have the ability to produce an amino acid. A microorganism having an ability to produce an amino acid can be obtained by imparting an amino acid-producing ability to a microorganism, or by enhancing an amino acid-producing ability of a microorganism. Either the impartation or enhancement of an enzyme-producing ability, such as introduction of a γ-glutamylvaline synthetase gene and/or a glutathione synthetase gene, or impartation or enhancement of an amino acid-producing ability may be carried out first. That is, a microorganism having γ-glutamylvaline synthetase and/or glutathione synthetase and having an ability to produce an amino acid may be obtained by modifying a microorganism having γ-glutamylvaline synthetase and/or glutathione synthetase to have an amino acid-producing ability, or may be obtained by modifying a microorganism having an amino acid-producing ability to have γ-glutamylvaline synthetase and/or glutathione synthetase. An L-amino acid-producing ability can be imparted or enhanced by methods conventionally employed in the breeding of amino acid-producing strains of coryneform bacteria, Escherichia bacteria, and so forth (see "Amino Acid Fermentation", Gakkai Shuppan Center Ltd., 1st Edition, published May 30, 1986, pp. 77-100). Such methods include, for example, acquiring an auxotrophic mutant strain, an L.-amino acid analogue-resistant strain, or a metabolic regulation mutant strain, and constructing a recombinant strain in which the activity of an L-amino acid biosynthesis system enzyme is enhanced. An 1-amino acid-producing ability can also be imparted or enhanced by reducing the activity of an enzyme that catalyses a reaction branching away from biosynthetic pathway of a target L-amino acid to generate a compound other than the target L-amino acid.

Examples of L-glutamic acid-producing bacteria include a recombinant strain obtained by introducing the mvN gene having VI 97M mutation into an odhA-deficient strain obtained from the Corynebacterium glutamicum (Brevibacterium lactofermentum) ATCC 13869 strain (Japanese Patent Laid-open (Kokai) No. 2010-161970), the Pantoea agglomerans A113355 strain introduced with the gltA (citrate synthase) gene derived from Brevibacterium lactofermentum (Japanese Patent No. 4285582), an Escherichia bacterium having glutamine synthetase in which the tyrosine residue at position 397 is replaced with another amino acid residue (U.S. Patent Published Application No. 2003/0148474), and so forth. Examples of L-valine-producing bacteria include the Escherichia coli VL1970 strain (U.S. Pat. No. 5,658,766) an Escherichia bacterium having a mutation for requiring lipoic acid for growth thereof and/or a mutation for lacking H -ATPase, an Escherichia bacterium that is, in addition to these characteristics, intracellularly introduced with a UNA fragment containing the ilvGMEDA operon that expresses at least the ilvG, ilvM, ilvE, and ilvl) genes, but does not express the threonine deaminase activity (WO96/06926), and so forth. That is, for example, by introducing any of these modifications into a microorganism, an amino acid-producing ability can be imparted or enhanced.

The microorganism may also have been modified so that the ability to uptake an amino acid added to the medium is improved. The microorganism may also have been modified so that the ability to excrete the generated γ-Glu-Val out of the cell is improved, or it may have been modified so that the ability to uptake γ-Glu-Val added to the medium is improved, depending on the scheme of use of the microorganism. The microorganism may also have been modified so that the ability to excrete the generated γ-Glu-Val-Gly out of the cell is improved.

Culture conditions are not particularly limited, so lung as the microorganism can proliferate, and γ-Glu-Val-Gly is generated. For the culture conditions, the descriptions concerning the culture conditions for the method for producing γ-glutamylvaline synthetase mentioned above can be referred to.

Both γ-glutamylvaline synthetase and glutathione synthetase use ATP for the enzymatic reaction. Therefore, ATP is supplied to the reaction system as required. That is, the reaction system may contain ATP. All of the aforementioned steps (A) to (C) can be carried out in the presence of ATP. The method for supplying ATP is not particularly limited so long as ATP can be used for the enzymatic reaction. ATP may be, for example, generated by a microorganism used in each step, or supplied to the reaction system by such a method for generating or regenerating ATP as mentioned above. For supplying ATP, for example, there can be preferably used a co-culture system such as those realized by a method of making a microorganism of which ATP regenerating system based on the usual energy metabolism is enhanced, or a microorganism having an ability to regenerate ATP by the action of polyphosphate kinase coexist in the culture medium (Japanese Patent Publication (Kokoku) Nos. 7-16431 and 6-69386).

Also, for example, γ-glutamylvaline synthetase typically requires a divalent metal ion for the enzymatic reaction. Therefore, the reaction system may contain a divalent metal ion. All of the steps (A) to (C) mentioned above can be carried out in the presence of a divalent metal ion.

When a medium containing an amino acid is used, the amino acid may be contained in the medium from the start of the culture, or may be added to the medium at an arbitrary time during the culture. Although the time of the addition can be changed as required according to various conditions such as culture time, the amino acid may be added, for example, preferably 0 to 50 hours, more preferably 0.1 to 24 hours, particularly preferably 0.5 to 6 hours, before the end of the culture. The amino acid may be added at one time, or two or more times, or it may be continuously added. The concentration of each of the amino acids in the medium may be, for example, usually 0.1 to 2000 mM, preferably 1 to 20(10 mM, more preferably 10 to 10(X) mM. As for molar ratio of substrates in the medium, the descriptions concerning the molar ratio of substrates in the reaction mixture for the enzymatic method may be applied mutatis mutandis.

By performing culture as described above, a culture broth containing γ-Glu-Val-Gly can be obtained. Generation of γ-Glu-Val-Gly can be confirmed by a known technique used for detection or identification of a compound as described above. γ-Glu-Val-Gly can be collected from the culture broth as required. γ-Glu-Val-Gly can be collected by a known technique used for separation or purification of a compound as described above. When γ-Glu-Val-Gly is accumulated in the cells, for example, the cells can be disrupted by ultrasonication or the like, and γ-Glu-Val-Gly can be collected by the ion-exchange resin method or the like from supernatant obtained by removing the cells by centrifugation.

When the microorganism having glutathione synthetase is yeast, and γ-Glu-Val-Gly is accumulated in the cells thereof, this yeast can be used for, for example, production of yeast extract containing γ-Glu-Val-Gly. That is, the present invention provides a method for producing yeast extract containing γ-Glu-Val-Gly, which comprises preparing yeast extract by using the yeast as a raw material. The yeast extract can be prepared from the yeast in the same manner as usual production of yeast extract. The yeast extract may be one obtained by hot water extraction of the yeast cells followed by treatment of the resulting extract, or one obtained by digestion of the yeast cells followed by treatment of the digested product. The obtained yeast extract may be concentrated, or may be dried to make it in the form of powder, as required.

EXAMPLES

Hereafter, the present invention will be more specifically explained with reference to examples.

Example 1: Construction of Expression Plasmid for ybdK Gene

An expression plasmid pSF12-EcybdK for the ybdK gene of *Escherichia coli* MG1655 (ATCC 47076) was constructed by the following procedure. The nucleotide sequence of the ybdK gene and the amino acid sequence of YBDK encoded by this gene are shown as SEQ ID NOS: 15 and 16, respectively. With pSF12-EcybdK, YBDK is expressed with a His tag added to the C-terminus.

First, a pUC18-derived plasmid pSF12_ggt (WO2013/051685A1) containing the ggt gene encoding γ-glutamyl transpeptidase derived from the *Escherichia coli* W3110 strain (ATCC 27325) and a rpoH promoter was digested with NdeI/PstI, and purified with QIAquick Gel Extraction Kit (Qiagen), to obtain a fragment of about 3.0 kb.

Then, PCR was carried out by using the genomic DNA of the *Escherichia coli* MG1655 strain as the template, and PrimeSTAR Max Polymerase (Takara Bio) according to the protocol of the manufacturer, to obtain a fragment of about 1.2 kb containing the ybdK gene. As the primers, the combination of the primers of SEQ ID NOS: 1 and 2 (Table 1) was used.

Then, a fragment of about 3.0 kb obtained by digesting pSF12_ggt with NdeI/PstI and the fragment of about 1.2 kb obtained by PCR and containing the ybdK gene were fused by using In-Fusion HD Cloning Kit (Clontech) according to the protocol of the manufacturer. The *Escherichia coli* JM109 strain was transformed with the reaction mixture, applied to LB agar medium (1.0% (w/v) peptone, 0.5% (w/v) yeast extract, 1.0% (w/v) NaCl, and 1.5% (w/v) agar) containing 100 μg/mL of ampicillin sodium salt (Amp), and cultured at 30° C. for 20 hours. Plasmids were extracted from the colonies of the grown transformants by a known method, the nucleotide sequences thereof were confirmed by using 3130 Genetic Analyzer (Life Technologies), and a plasmid having the objective structure was designated as pSF12-EcybdK.

TABLE 1

| SEQ ID NO | Nucleotide sequence (5'->3') |
|---|---|
| 1 | taaggaggaatccatATGCCATTACCCGATTTTCA |
| 2 | cttgcatgcctgcagTTAatgatgatgatgatgatgGTCACCGGCCCAGATCTCACAATG |

Example 2: Purification of YBDK Derived from *Escherichia coli* MG1655 Strain and Having His Tag Added to C-Terminus The JM109 strain harboring the plasmid pSF12-EcybdK, which was obtained in Example 1, was inoculated into 3 mL of LB medium containing 100 jig/mL of Amp, and cultured at 30° C. for 20 hours with shaking by 120 times/minute of reciprocal movement, to obtain a preculture broth. The obtained preculture broth in a volume of 150 μL was inoculated into 15 mL of TB medium (1.2% (w/v) tryptone. 2.4% (w/v) yeast extract, 0.4% (w/v) glycerol, 0.23% (w/v) KH$_2$PO$_4$, and 1.25% (w/v) K$_2$HPO$_4$) containing 100 μg/mL of Amp contained in a 70 mL-volume test tube Op 25 mm), and cultivation was carried out at 30° C. for 20 hours with shaking by 120 times/minute of reciprocal movement. Cells were collected by centrifugation (4° C., 12,000 rpm, 5 minutes). The obtained cells were suspended in 0.2 mL of a buffer (20 mM Tris-HCl (pH 8.0), 300 mM NaCl, 10 mM imidazole, and 15% glycerol), and disrupted by ultrasonication with cooling. The obtained disrupted cell suspension was centrifuged (4° C., 29,100×g, 10 minutes), and the obtained supernatant was used as a cell-free extract.

The obtained cell-free extract was applied to Nickel Sepharose 6 Fast Flow Beads (GE Healthcare) equilibrated beforehand with a buffer (20 mM Tris-HCl(pH 8.0), 300 mM NaCl, 10 mM imidazole, and 15% glycerol), and the enzyme was eluted with an elution buffer (20 mM Tris-HCl (pH 8.0). 300 mM NaCl. 250 mM imidazole, and 15% glycerol) to obtain an active fraction. This active fraction was used as a purified YBDK for the following experiments.

Example 3: Production of γ-Glutamyl Dipeptide with Purified YBDK

The γ-Glu-Val synthetic activity and γ-Glu-Gly synthetic activity of the purified YBDK obtained in Example 2 were measured.

The measurement conditions of the γ-Glu-Val synthetic activity were as follows. Composition of the reaction mixture consisted of 10 mM glutamic acid, 10 mM valine, 111 mM ATP, and 10 mM MnSO$_4$ in 100 mM Tris-HCl (pH7.0). The volume of the reaction mixture was 0.2 mL, and the enzymatic reaction was started by adding the purified enzyme. At this time, the purified YBDK was added to the reaction mixture at a concentration of 0.1 g/L. The reaction temperature was 30° C., and the reaction time was 30 minutes. For terminating the reaction, 0.2 mL of 200 mM sulfuric acid was added per 0.2 mL of the reaction mixture. After completion of the reaction, the generated γ-Glu-Val was quantified by HPLC. The enzymatic activity for generating 1 μmot of γ-Glu-Val in 1 minute under the aforementioned conditions was defined as 1 U of the γ-Glu-Val synthetic activity.

The quantification conditions for γ-Glu-Val were as follows. Synergi 4μHydro-RP 80A produced by Phenomenex (particle size 4 microns, inner diameter 4.6 mm, length 250 mm) was used as the column. As the eluent, a mixture consisting an eluent A (50 mM sodium dihydrogenphosphate (pH 2.5, adjusted with phosphoric acid)) and eluent B (1:1 (v/v) mixture of eluent A and acetonitrile) in a ratio of 93:7 (v/v) was used. The flow rate was 1.0 mL/minute. column temperature was 40° C., and UV detection wavelength was 210 nm.

When the γ-Glu-Gly synthetic activity was measured, valine in the aforementioned reaction mixture was replaced with glycine, and 0.025 g/L of the purified YBDK was added to the reaction mixture to perform the enzymatic reaction. The reaction was terminated in the same manner as described above, and then the generated γ-Glu-Gly was quantified. The enzymatic activity for generating 1 μmol of γ-Glu-Gly in 1 minute under the aforementioned conditions was defined as 1 U of the γ-Glu-Gly synthetic activity.

The quantification conditions for γ-Glu-Gly were as follows. Inertsil ODS-3 produced by GL Science (particle size 5 microns, inner diameter 4.6 mm, length 250 mm) was used as the column. As the eluent, an eluent C (1(X) mM potassium dihydrogenphosphate, 5 mM sodium octanesulfonate (pH 2.2, adjusted with phosphoric acid)) was used. The flow rate was 1.5 mL/minute, column temperature was 40° C., and UV detection wavelength was 219 nm.

By the methods described above, the amounts of generated γ-Glu-Val and γ-Glu-Gly were quantified, and specific activities were calculated. The results are shown in Table 2. In the table, data in the columns of "Reaction (A)", "Reaction (B)", and "(B)/(A)" indicated the specific activities of the γ-Glu-Gly synthetic activity, specific activities of the γ-Glu-Val synthetic activity, and ratios of the specific activity of γ-Glu-Val synthetic activity to the specific activity of γ-Glu-Gly synthetic activity, respectively.

TABLE 2

| Enzyme (origin) | Reaction (A)<br>Glu + Gly + ATP<br>(U/mg) | Reaction (B)<br>Glu + Val + ATP<br>(U/mg) | (B)/(A) |
|---|---|---|---|
| YBDK (*E. coli*) | 0.11 | 0.29 | 2.6 |

Example 4: Construction of Triple-Gene-Disruption Strain Deficient in at, gshA, and ybdK genes derived from *Escherichia coli* JM109 strain (1) Construction of ggt-gene disruption strain derived from *Escherichia coli* JM109 strain A strain not producing GGT was constructed from the *Escherichia coli* JM109 strain as the parent strain. The nucleotide sequence of the ggt gene and the amino acid sequence of GGT encoded by the gene are shown in SEQ ID NOS: 25 and 26, respectively.

Gene disruption was carried out by using a combined method (WO2005/010175) of the method called "Red-driven integration", which was first developed By Datsenko and Wanner (Proc. Natl. Acad. Sci. USA, 2000. vol. 97, No. 12. pp. 6640-6645) and the excision system originated from λ phage (J. Bacteriol. 2002 September; 184(18): 5200-3. Interactions between integrase and excisionase in the phase lambda excisive mucleoprotein complex. Cho E H, (impart R I, Gardner J F.). According to the "Red-driven integration" method, a target gene on a chromosome can be replaced with an antibiotic resistance gene by using a PCR product containing the antibiotic resistance gene, which product was obtained by PCR using synthetic oligonucleotides in each of which a sequence corresponding to a part of the target gene is designed on the 5' side, and thereby a gene disruption strain can be constructed. In addition, by using the excision system originated from λ phage in combination, the antibiotic resistance gene integrated into the gene disruption strain can be removed.

As the template for the "Red-driven integration" method, pMW118-attL-Cm-attR (WO2006/078039) was used. pMW118-attL-Cm-attR (WO2006/0711039) is a plasmid in which attl, and atilt genes, which are attachment sites of X phage, and a cat gene, which is an antibiotic resistance gene, have been inserted into pMW118 (Nippon Gene Co., Ltd.) in the order of attL-cat-attR PCR was canned out by using as primers synthetic oligonucleotides having sequences corresponding to the respective ends of attL and attR genes at the 3' ends and sequences corresponding to a part of the target gene at the 5' ends, to obtain a fragment for gene disruption. A gene disruption strain was constructed by using the obtained fragment for gene disruption. Procedures are shown below.

A fragment for disrupting the ggt gene was obtained as follows. That is, PCR was carried out by using the genomic DNA of the *Escherichia coli* JM109 strain as the template, primers of SEQ ID NOS: 3 and 4, and KOD-plus-Ver.2 (IOYOBO) according to the protocol of the manufacturer, to amplify an upstream region of the ggt gene of 0.3 kb, to thereby obtain a fragment A. Similarly, PCR was carried out by using the genomic DNA of the *Escherichia coli* JM109 strain as the template, and primers of SEQ ID NOS: S and 6, to amplify a downstream region of the ggt gene of 0.3 kb, to thereby obtain a fragment C. Similarly. PCR was carried out by using pMW118-attL-Cm-attR as the template, and primers of SEQ ID NOS: 7 and 8, to obtain a fragment B of 1.6 kb. PCR reaction of 10 cycles was carried out by using 50 ng, 10 ng, and 50 ng of the fragments A, B, and C for 50 μL of PCR reaction mixture. A DNA fragment of 2 kb was amplified by using 1 μL of this reaction mixture as the template, and primers of SEQ ID NOS: 3 and 6, and purified with QIAquick Gel Extraction Kit (Qiagen), to obtain the fragment for disrupting the ggt gene. The primers used are shown in Table 3.

TABLE 3

| SEQ ID NO | Nucleotide sequence (5'->3') |
|---|---|
| 3 | TGCATCTGGGTTTGCATCCGCTGCT |
| 4 | ataaaaaagcaggcttcaCGTTATTCTCCAGAGATTAAGGGGC |
| 5 | tttatactaacttgagcgGGTTAGCGGCCCTCTTCGTGGGAAG |
| 6 | ACTCTACATGGACGCTTTAGCCAGG |
| 7 | GCCCCTTAATCTCTGGAGAATAACGtgaagcctgcttttttat |
| 8 | CTTCCCACGAAGAGGGCCGCTAACCcgctcaagttagtataaa |

The obtained fragment for disrupting the ggt gene was introduced into the *Escherichia coli* JM109 strain containing a plasmid pKD46 (Proc. Natl. Acad. Sci. USA, 2000, vol. 97. No. 12, p6640-6645) by electroporation. The plasmid pKD46 is a plasmid having a temperature-sensitive replication ability and containing a DNA fragment of total 2154 base-pain from λ-phage (GenDank/DMDL Accession; J02459, position 31088-33241), which fragment contains genes encoding the Red recombinase of the A-Red homologous recombination system (γ, β, and exo genes) under the control of an arabinose-inducible $P_{enB}$promoter. The plasmid pKD46 is required for integrating the DNA fragment for gene disruption into the chromosome of the JM109 strain.

Competent cells for electroporation were prepared as follows. That is, the *Escherichia call* JM109 strain containing the plasmid pKD46 was cultured in LB medium containing 100 mg/L of Amp at 30° C. for 20 hours, and diluted 50-fold with 2 mL of SOB-medium (Sambrook J., et al., Molecular Cloning: A Laboratory Manual ($2^{nd}$ ed.), Cold Spring Harbor Laboratory Press, 1989) containing Amp (100 mg/L). The diluted product was grown at 30° C. to 013610 of about 0.3, added with 70 ILL of 10%(v/v) L-arabinose, and cultured for 1 hour at 37° C. The obtained culture broth was concentrated 65-fold, and washed 3 times with 10%(v/v) glycerol, to obtain the competent cells for electroporation.

Alter electroporation, the cell suspension was added with 0.3 mL of SOC medium, cultured for 3 hours at 37° C., and then cultured on LB-agar medium containing 50 mg/L of chloramphenicol (Cm) at 37° C., to select a Cm-resistant recombinant.

Then, for removal of the plasmid pKD46, cultivation was carried out on LB-agar medium containing Cm (50 mg/L) at 42° C., and obtained colonies were tested for Amp resistance, to obtain an Amp-sensitive strain, from which the plasmid pKD46 was removed. Disruption of the ggt gene marked with the Cm-resistant gene was confirmed by PCR. The obtained ggt-gene disruption strain was designated as the strain JM109Δggt:att-cat.

Then, for removal of the att-cat genes introduced into the at gene, pMW-intxis-ts (WO2007/037460) was used as a helper plasmid. pMW-intxis-ts is a plasmid having a temperature-sensitive replication ability and containing genes encoding integrase (Int) and excisionase (Xis) of λ-phage. As a result of introduction of pM W-intxis-ts, ail, or attR on the chromosome is recognised and recombination occurs to excise a gene between attL and attR, so that only the attL or attR sequence remains on the chromosome. The JM109Δggt:att-cat strain obtained above was transformed with pMW-intxis-ts, and cultured on LB-agar medium containing 100 mg/L of Amp at 30° C., to obtain an Amp-resistant strain.

Then, for removal of the plasmid pMW-intxis-ts, cultivation was carried out on LB-agar medium at 42° C. and obtained colonies were tested for Amp resistance and Cm resistance, to obtain a Cm— and Amp-sensitive strain, from which att-cat and pMW-intxis-ts was removed and of which the al gene was disrupted. This strain was designated as the strain JM109Δggt.

(2) Construction of double-gene-disruption strain deficient in ggt and gshA genes derived from Escherichia coli JM109 strain A strain not producing GGT or GSHA was constructed from the Escherichia coli JM109Δggt strain as the parent strain. The nucleotide sequence of the gshA gene and the amino acid sequence of GSHA encoded by the gene are shown in SEQ ID NOS: 23 and 24, respectively.

A DNA fragment for disrupting the gshA gene was obtained by carrying out PCR using pMW118-attL-Cm-attR as the template, primers of SEQ ID NOS: 9 and 10 (Table 4), and KOD-plus-Ver.2 (TOYOBO) according to the protocol of the manufacturer. The fragment for disrupting the gshA gene was introduced into the JM109Δggt strain containing the plasmid pKD46 by electroporation. Competent cells of the JM109Δggt strain for electroporation were obtained in the same manner as described in Example 4(I). Alter electroporation, the cell suspension was added with 0.3 mL of SOC medium, cultured for 3 hours at 37° C., and then cultured on LB-agar medium containing Cm (50 mg/L) at 37° C., to select a Cm-resistant recombinant. Then, for removal of the plasmid pKD46, cultivation was carried out on LB-agar medium containing Cm (50 mg/L) at 42° C., and obtained colonies were tested for Amp resistance, to obtain an Amp-sensitive strain, from which the plasmid pKD46 was removed. Disruption of the gshA gene marked with the Cm-resistant gene was confirmed by PCR. The obtained gshA-gene disruption strain was designated as the strain JM109ΔggtΔgshΔ:att-cat.

Then, for removal of the attL-cat genes introduced into the gshA gene, the JM109ΔggtΔgshΔ:att-cat strain obtained above was transformed with pMW-intxis-ts, and cultured on LB-agar medium containing 100 mg/L of Amp at 30° C., to obtain an Amp-resistant strain.

Then, for removal of the plasmid pMW-intxis-ts, cultivation was carried out on LB-agar medium at 42° C., and obtained colonies were tested for Amp resistance and Cm resistance, to obtain a Cm— and Amp-sensitive strain, from which all-cat and pMW-intxis-ts was removed and of which the gshA gene was disrupted. This strain was designated as the strain JM109ΔggtΔgshA.

TABLE 4

| SEQ ID NO | Nucleotide sequence (5'->3') |
|---|---|
| 9 | TTATGCTAATTAAAACGATTTTGACAGGCGGGAGGTCAAT tgaagcctgctttttat |
| 10 | TGAAATTTTGGCCACTCACGAGTGGCCTTTTTCTTTTCTG cgctcaagttagtataaa |

(3) Construction of triple-gene-disruption strain deficient in ggt, OA, and ybdK genes derived from Escherichia coli JM109 strain A strain not producing GGT, GSHA, or YBDK was constructed from the Escherichia coli JM109ΔggtΔgshA strain as the parent strain. The nucleotide sequence of the ybdK gene and the amino acid sequence of YBDK encoded by the gene are shown in SEQ ID NOS: 15 and 16, respectively.

A DNA fragment for disrupting the ybdK gene was obtained by carrying out PCR using pMW1 I8-attL-Cm-attR as the template, primers of SEQ ID NOS: 11 and 12 (Table 5), and PrimeSTAR Max Polymerase (Takara Bio) according to the protocol of the manufacturer. The fragment for disrupting the ybdK gene was introduced into the JM109ΔggtΔgshA strain containing the plasmid pKD46 by electroporation. Competent cells of the JM109ΔggtΔgshA strain for electroporation were obtained in the same manner as described in Example 4(1). After electroporation, the cell suspension was added with 0.3 mL of SOC medium, cultured for 3 hours at 37° C., and then cultured on LB-agar medium containing Cm (50 mg/L) at 37° C., to select a Cm-resistant recombinant.

Then, for removal of the plasmid pKD46, cultivation was carried out on LB-agar medium containing Cm (50 mg/L) at 42° C. and obtained colonies were tested for Amp resistance, to obtain an Amp-sensitive strain, from which the plasmid pKD46 was removed. Disruption of the ybdK gene marked with the Cm-resistant gene was confirmed by PCR. The obtained ybdK-gene disruption strain was designated as the strain JM109ΔggtΔgshAΔybdK:att-cat.

Then, for removal of the att-cat genes introduced into the ybdK gene, the JM109ΔggtΔgshAΔybdK:att-cat strain obtained above was transformed with pMW-intxis-ts, and cultured on LB-agar medium containing 100 mg/L of Amp at 30° C., to obtain an Amp-resistant strain.

Then, for removal of the plasmid pM W-intxis-ts, cultivation was carried out on LB-agar medium at 42° C. and obtained colonies were tested for Amp resistance and Cm resistance, to obtain a Cm— and Amp-sensitive strain, from which att-cat and pM W-intxis-ts was removed and of which the ybdK gene was disrupted. This strain was designated as the strain JM109ΔggtΔgshAΔybdK.

TABLE 5

| SEQ ID NO | Nucleotide sequence (5'->3') |
|---|---|
| 11 | cttctatactgaatagaaaacgccaacataagagaaacct TGAAGCCTGCTTTTTTATACTAAGTTGGCATTATAAAAAA |
| 12 | accattgtcagggatattcttctgtaaggcaattcccggc CGCTCAAGTTAGTATAAAAAAGCTGAACGAGAAACGTAAA |

Example 5: Construction of Expression Strains for Kocuria Rosea γ-Glu-Val Synthetase Expression strains for Kocuria Rosea γ-Glu-Val synthetase were constructed from the double-gene-disruption strain deficient in ggt and gshA genes (JM109ΔggtΔgshA) and triple-gene-disruption strain deficient in ggt, gshA, and ybdK genes (JM109ΔggtΔgshAΔybdK) derived from the Escherichia coli JM109 strain as the expression hosts. The nucleotide sequence of the KrgshA gene encoding γ-Glu Val synthetase derived from the Kocuria Rosea AJ3132 strain is shown in SEQ ID NO: 17. The amino acid sequence of γ-Glu-Val synthetase encoded by the gene is shown in SEQ ID NO: 18. Incidentally upon constructing pSF-KrgshA, an expression plasmid for the KrgshA gene, a nucleotide sequence codon-optimised for expression in Escherichia coil was designed on the basis of the nucleotide sequence of the KrgshA gene (SEQ ID NO: 17). The nucleotide sequence of the KrgshA gene codon-optimised for expression in Escherichia coli is shown in SEQ ID NO: 29.

First, a pUC18-derived plasmid pSF12t (WO2013/051685A1) containing a ggt gene encoding γ-glutamyl transpeptidase derived from the Escherichia coli W3110 strain (ATCC 27325) and a rpoH promoter was digested with Nde1/Pst1, and purified with QIAquick Gel Extraction Kit (Qiagen), to obtain a fragment of about 3.0 kb.

Then, cDNA (SEQ ID NO: 29) designed to be codon-optimized for expression in Escherichia coli on the basis of the nucleotide sequence of the KrgshA gene (SEQ ID NO: 17) was ordered to Eurofins Genomics. PCR was carried out by using the delivered plasmid as the template, and Phusion High-Fidelity DNA Polymerase (FINNZYMES) according to the protocol of the manufacturer, to obtain a fragment of about 1.2 kb containing the KrgshA gene. As the primers, the combination of SEQ ID NOS: 13 and 14 (Table 6) was used.

Then, the PCR fragment of about 1.2 kb obtained by PCR and containing the KrgshA gene and the fragment of about 3.0 kb obtained by digesting pSF12_ggt with Nde1/Pst1 were fused by using In-Fusion HD Cloning Kit (Clontech) according to the protocol of the manufacturer. The Escherichia coli JM109 strain was transformed with the reaction mixture, applied to LB agar medium containing 100 μg/mL of ampicillin sodium salt (Amp), and cultured at 30° C. for 20 hours. Plasmids were extracted from the colonies of the grown transformants by a known method, the nucleotide sequences thereof were confirmed by using 3130 Genetic Analyser (Life Technologies), and a plasmid having the objective structure was designated as pSF12-KrGshA.

The strains JM109ΔggtΔgshA and JM109ΔggtΔgshAΔybdK obtained in Example 4 were each transformed with pSF12-KrgshA, to obtain transformants containing pSF I2-KrgshA. These transformants were designated as strains JM109ΔggtΔgshA/pSF12-KrgshA and JM109ΔggtΔgshAΔybdK/pSF12-KrgshA, respectively.

TABLE 6

| SEQ ID NO | Nucleotide sequence (5'->3') |
|---|---|
| 13 | AAGGAGGAATCCATATGGAAATCTCGTTTGCCCGC |
| 14 | CCAAGCTTGCATGCCIGCAGTTAGTCGTTTTCGCGAGTACG |

Example 6: Production of γ-Glutamyl Dipeptide with Cell-Free Extract of Expression Strains for Kocuria rosea γ-Glu-Val Synthetase Production of γ-glutamyl dipeptide was investigated by using a cell-free extract of expression strains for Kocuria rosea γ-Glu-Val synthetase constructed from the double-gene-disruption strain deficient in ggt and gshA genes (JM109ΔggtΔgshA) and triple-gene-disruption strain deficient in at, gshA, and ybdK genes (JM109ΔggtΔgshAΔybdK) derived from the Escherichia coli JM109 strain as the expression hosts.

The strains JM109ΔggtΔgshA/pSF12-KrgshA and JM109ΔggtΔgshAΔybdK/pSF12-KrgshA obtained in Example 5 were each inoculated into 3 mL of LB medium containing 100 μg/mL of Amp, and cultured at 30° C. For 20 hours with shaking by 120 times/minute of reciprocal movement, to obtain a preculture broth. The obtained preculture broth in a volume of 150 μL was inoculated into 15 mL of TB medium containing 100 μg/mL of Amp contained in a 70 mL-volume test tube (*p 25 mm), and cultivation was carried out at 30° C. for 20 hours with shaking by 120 times/minute of reciprocal movement. Cells were collected by centrifugation (4° C., 12,000 rpm, 5 minutes). The obtained cells were suspended in 0.2 mL of a buffer (20 mM Tris-HCl (pH 8.0). 300 mM NaCl, 10 mM imidazole, and 15% glycerol), and disrupted by ultrasonication with cooling. The obtained disrupted cell suspension was centrifuged (4° C., 29,100×g, 10 minutes), and the obtained supernatant was used as a cell-free extract.

First, the γ-Glu-Val synthetic activity was measured by using the cell-free extract. Composition of the reaction mixture consisted of 100 mM glutamic acid, 100 mM valine. 40 mM ATP, and 20 mM $MgSO_4$ in 1011 mM Tris-HCl (pH7.0). The volume of the reaction mixture was 0.5 mL. The enzymatic reaction was started by adding the cell-free extract containing 0.25 mg of proteins. The reaction temperature was 30° C., and the reaction time was 30 minutes. For terminating the reaction, 0.5 mL of 200 mM sulfuric acid was added per 0.5 mL of the reaction mixture. After completion of the reaction, γ-Glu-Val was quantified by means shown in Example 3, and the γ-Glu-Val synthetic activity per cell-free extract was calculated. Results are shown in Table 7.

TABLE 7

| Origin of cell-free extract | γ-Glu-Val synthetic activity (U/mg) |
|---|---|
| JM109ΔggtΔgshA/pSF12-KrgshA | 0.008 |
| JM109ΔggtΔgshAΔybdK/pSF12-KrgshA | 0.024 |

Then, the γ-Glu-Val synthesis amount and the γ-Glu-Gly synthesis amount in the presence of Glu, Val, and Gly were measured by using the obtained cell-free extract. Composition of the reaction mixture consisted of 100 mM glutamic acid, 50 mM valine, 50 mM glycine, 40 mM ATP, and 20 mM MgSO₄ in 100 mM Tris-HCl(p117.0). The enzymatic reaction was started by adding the cell-free extract. For terminating the reaction, an equal volume of 20(1 mM sulfuric acid was added to the reaction mixture. After completion of the reaction, γ-Glu-Val and γ-Glu-Gly were quantified by means shown in Example 3. Results are shown in Tables 8 and 9. Table 8 shows data obtained when the cell-free extract was added to the reaction mixture in an amount of 0.004 U in terms of the γ-Glu-Val synthetase activity. In this case, the volume of the reaction mixture was 0.2 mL, the reaction temperature was 30° C., and the reaction time was 16 hours. fable 9 shows data obtained when the cell-free extract containing 0.25 mg of proteins was added to the reaction mixture. In this case, the volume of the reaction mixture was 0.5 mL, the reaction temperature was 30° C., and the reaction time was 2.5 hours.

TABLE 8

| Origin of cell-free extract | γ-Glu-Val (mM) | γ-Glu-Gly (mM) |
|---|---|---|
| JM109ΔggtΔgshA/pSF12-KrgshA | 0.4 | 0.1 |
| JM109ΔggtΔgshAΔybdK/pSF12-KrgshA | 0.7 | n.d. | n.d.: below detection limit.

TABLE 9

| Origin of cell-free extract | γ-Glu-Val (mM) | γ-Glu-Gly (mM) |
|---|---|---|
| JM109ΔggtΔgshA/pSF12-KrgshA | 0.5 | 0.1 |
| JM109ΔggtΔgshAΔybdK/pSF12-KrgshA | 2.1 | n.d. | n.d.: below detection limit.

INDUSTRIAL APPLICABILITY

According to the present invention, a microorganism useful as an expression host for γ-Glu-Val synthetase can be provided. By using γ-Glu-Val synthetase expressed in the microorganism, γ-Glu-Val or Y-Glu-Val-Gly can be efficiently produced. For example, by using Y-Glu-Val synthetase expressed in the microorganism in combination with glutathione synthetase, it is expected that γ-Glu-Val-Gly can be efficiently produced from Glu, Val, and Gly as raw materials with reduced by-production of γ-Glu-Gly.

<Explanation of Sequence Listing>
SEQ ID NOS:
  1-14: Primers
  15: Nucleotide sequence of ybdK gene of *Escherichia coli* W3110 strain
  16: Amino acid sequence of YBDK of *Escherichia coli* K-12 W3110 strain
  17: Nucleotide sequence of γ-Glu-Val synthetase gene of *Kocuria rosea* (A73132)
  1K: Amino acid sequence of γ-Glu-Val synthetase of *Kocuria rosea* (AJ3132)
  19: Nucleotide sequence of γ-Glu-Val synthetase gene of *Kocuria rhizophila* DC2201 strain
  20: Amino acid sequence of γ-Glu-Val synthetase of *Kocuria rhizophila* DC2201 strain
  21: Nucleotide sequence of γ-Glu-Val synthetase gene of *Micrococcus luteus* NCTC2665 strain
  22: Amino acid sequence of γ-Glu-Val synthetase of *Micrococcus luteus* NCTC2665 strain
  23: Nucleotide sequence of gshA gene of *Escherichia coli* K-12 W3110 strain
  24: Amino acid sequence of GSHA of *Escherichia coli* K-12 W3110 strain
  25: Nucleotide sequence of ggt gene of *Escherichia coli* K-12 MG1655 strain
  26: Amino acid sequence of GGT of *Escherichia coli* K-12 MG1655 strain
  27: Nucleotide sequence of gshB gene of *Escherichia coli* K-12 W3110 strain
  2K: Amino acid sequence of GSHB of *Escherichia coli* K-12 W3110 strain
  29: Nucleotide sequence of γ-Glu-Val synthetase gene of *Kocuria rosea* (AJ3132) optimised for expression in *Escherichia coli*

The invention claimed is:

1. A modified, *Escherichia coli* bacterium,
wherein the bacterium has a deleted ybdK gene that encodes γ-glutamylglycine synthetase that is at least 90% identical to the amino acid sequence of SEQ ID NO: 16, wherein the bacterium has a reduced γ-glutamylglycine synthetase activity compared to a non-modified bacterium, wherein the bacterium has a deleted gshA gene that encodes a γ-glutamylcysteine synthetase that is at least 90% identical to the amino acid sequence of SEQ ID NO: 24, wherein the bacterium has a reduced γ-glutamylcysteine synthetase activity compared to a non-modified bacterium, wherein the bacterium has a deleted gene that encodes a γ-glutamyltransferase that is at least 90% identical to the amino acid sequence of SEQ ID NO: 26, wherein the bacterium has a reduced γ-glutamyltransferase activity compared to a non-modified bacterium, wherein the bacterium has a gene encoding γ-glutamylvaline synthetase, wherein the γ-glutamylvaline synthetase has an amino acid sequence that is at least 90% identical to the amino acid sequence of SEQ ID NO: 24 mutated with a substitution at a position selected from L135, Q144, Y241, N243, and Y300, or wherein the γ-glutamylvaline synthetase has an amino acid sequence that is at least 90% identical to the amino acid sequence of SEQ ID NO: 18, 20, or 22, wherein the γ-glutamylvaline synthetase has a ratio of γ-glutamylvaline synthetase activity to γ-glutamylglycine synthetase activity of at least 3.0, and wherein the bacterium has enhanced ability to produce γ-glutamylvaline or γ-glutamylvalylglycine compared to a non-modified bacterium.

2. The bacterium of claim 1, wherein the mutation to the amino acid sequence of SEQ ID NO: 24 in the γ-glutamylvaline synthetase is selected from the group consisting of:
L135(I, F, M, V, G, A, W, K, H, R, C, N, S, or T),
Q144(F, A, N, S, D, T, R, H, G, K, Y, W, C, M, P, V, L, or I),
Y241(A),
N243(I, W, K, R, or H), and
Y300(A, H, R, or K).

3. The bacterium of claim 1, wherein the mutation to the amino acid sequence of SEQ ID NO: 24 in the γ-glutamylvaline synthetase is selected from the group consisting of:
L135I/Q144R, L135I/Q144D, L135I/Q144A, L135I/Q144L, L135I/N243W, L135I/N243F, L135F/Q144A, L135F/N243W, L135M/Q144R, L135M/Q144A, L135M/Q144L, L135M/N243W, L135M/N243F, L135M/Q144H, L135M/Q144N, L135M/N243Y, L135M/N243R, L135M/N243C, L135V/Q144R, L135V/Q144D, L135V/Q144A, L135V/Q144L, L135V/Q144V, L135V/Q144K, L135V/Q144C, L135V/Q144T, L135H/Q144R, L135G/Q144L, L135A/Q144L, L135V/N243W, L135V/N243F, L135V/N243P, Q144R/N243W, Q144D/N243F, Q144R/N243F, Q144D/N243F, Q144A/N243W, Q144A/N243F, Q144L/N243W, Q144L/N243F, L135M/Q144F, L135M/N243A, L135V/N243G, L135V/N243A, L135V/N243L, L135V/N243Y, L135V/N243K, L135V/N243R, L135V/N243H, L135V/N243D, L135V/N243E, L135V/N243C, L135V/N243Q, L135V/N243S, L135V/N243T, L135V/Q144I, L135V/Q144P, L135V/Q144W, L135V/Q144H, L135V/Q144E, L135V/Q144N, L135V/Q144S, L135K/Q144L, L135H/Q144L, L135D/Q144L, L135C/Q144L, L135Q/Q144L, L135N/Q144L, L135S/Q144L, and L135T/Q144L.

4. The bacterium of claim 1, wherein the mutation to the amino acid sequence of SEQ ID NO: 24 in the γ-glutamylvaline synthetase is selected from the group consisting of:
L135(I, M, V, G, A, K, H, C, N, S, or T),
Q144(F, A, S, D, T, R, H, K, Y, W, C, M, P, V, L, or I),
N243(R or H),
Y300(R or K),
L135I/Q144R, L135I/Q144D, L135I/Q144A, L135I/Q144L, L135I/N243W, L135I/N243F, L135F/Q144A, L135M/Q144R, L135M/Q144A, L135M/Q144L, L135M/N243W, L135M/Q144H, L135M/Q144N, L135M/N243C, L135V/Q144R, L135V/Q144D, L135V/Q144A, L135V/Q144L, L135V/Q144V, L135V/Q144K, L135V/Q144C, L135V/Q144T, L135H/Q144R, L135G/Q144L, L135A/Q144L, L135V/N243W, L135V/N243F, L135V/N243P, Q144R/N243W, Q144D/N243W, Q144A/N243W, Q144A/N243F, Q144L/N243W, Q144L/N243F, L135M/Q144F, L135M/N243A, L135V/N243G, L135V/N243A, L135V/N243L, L135V/N243Y, L135V/N243K, L135V/N243R, L135V/N243H, L135V/N243D, L135V/N243E, L135V/N243C, L135V/N243Q, L135V/N243S, L135V/N243T, L135V/Q144P, L135V/Q144W, L135V/Q144H, L135V/Q144E, L135V/Q144N, L135V/Q144S, L135D/Q144L, L135C/Q144L, L135N/Q144L, L135S/Q144L, and L135T/Q144L.

5. The bacterium of claim 1, wherein the bacterium has a gene encoding glutathione synthetase.

6. The bacterium of claim 1,
wherein the protein encoded by the ybdK gene has an amino acid sequence that is at least 95% identical to the amino acid sequence of SEQ ID NO: 16, and
wherein the γ-glutamylvaline synthetase has an amino acid sequence that is at least 95% identical to the amino acid sequence of SEQ ID NO: 24 mutated with the substitution.

7. The bacterium of claim 1,
wherein the mutation to the amino acid sequence of SEQ ID NO: 24 in the γ-glutamylvaline synthetase is selected from the group consisting of:
L135(I, F, M, V, G, A, W, K, H, R, C, N, S, or T),
Q144(F, A, N, S, D, T, R, H, G, K, Y, W, C, M, P, V, L, or I),
Y241(A),
N243(I, W, K, R, or H), and
Y300(A, H, R, or K).

8. The bacterium of claim 1,
wherein the protein encoded by the ybdK gene has the amino acid sequence of SEQ ID NO: 16,
wherein the protein encoded by the gshA gene has the amino acid sequence of SEQ ID NO: 24,
wherein the γ-glutamyltransferase has the amino acid sequence of SEQ ID NO: 26, and
wherein the γ-glutamylvaline synthetase has the amino acid sequence of SEQ ID NO: 18, 20, or 22.

9. The bacterium of claim 1,
wherein the protein encoded by the ybdK gene has an amino acid sequence that is at least 95% identical to the amino acid sequence of SEQ ID NO: 16,
wherein the protein encoded by the gshA gene has an amino acid sequence that is at least 95% identical to the amino acid sequence of SEQ ID NO: 24,
wherein the γ-glutamyltransferase has an amino acid sequence that is at least 95% identical to the amino acid sequence of SEQ ID NO: 26, and
wherein the γ-glutamylvaline synthetase has an amino acid sequence that is at least 95% identical to the amino acid sequence of SEQ ID NO: 18, 20, or 22.

10. The bacterium of claim 1, wherein the protein encoded by the ybdK gene has an amino acid sequence that is at least 97% identical to the amino acid sequence of SEQ ID NO: 16,
wherein the protein encoded by the gshA gene has an amino acid sequence that is at least 97% identical to the amino acid sequence of SEQ ID NO: 24,
wherein the γ-glutamyltransferase has an amino acid sequence that is at least 97% identical to the amino acid sequence of SEQ ID NO: 26, and wherein the γ-glutamylvaline synthetase has an amino acid sequence that is at least 97% identical to the amino acid sequence of SEQ ID NO: 18, 20, or 22.

11. The bacterium of claim 1,
wherein the protein encoded by the ybdK gene has the amino acid sequence of SEQ ID NO: 16,
wherein the protein encoded by the gshA gene has the amino acid sequence of SEQ ID NO: 24,
wherein the γ-glutamyltransferase has the amino acid sequence of SEQ ID NO: 26, and
wherein the γ-glutamylvaline synthetase has the amino acid sequence of SEQ ID NO: 24 mutated with the substitution.

12. The bacterium of claim 1,
wherein the protein encoded by the ybdK gene has an amino acid sequence that is at least 95% identical to the amino acid sequence of SEQ ID NO: 16,
wherein the protein encoded by the gshA gene has an amino acid sequence that is at least 95% identical to the amino acid sequence of SEQ ID NO: 24,
wherein the γ-glutamyltransferase has an amino acid sequence that is at least 95% identical to the amino acid sequence of SEQ ID NO: 26, and
wherein the γ-glutamylvaline synthetase has as amino acid sequence that is at least 95% identical to the amino acid sequence of SEQ ID NO: 24 mutated with the substitution.

13. The bacterium of claim 1,
wherein the protein encoded by the ybdK gene has an amino acid sequence that is at least 97% identical to the amino acid sequence of SEQ ID NO: 16,
wherein the protein encoded by the gshA gene has an amino acid sequence that is at least 97% identical to the amino acid sequence of SEQ ID NO: 24,
wherein the γ-glutamyltransferase has an amino acid sequence that is at least 97% identical to the amino acid sequence of SEQ ID NO: 26, and
wherein the γ-glutamylvaline synthetase has an amino acid sequence that is at least 97% identical to the amino acid sequence of SEQ ID NO: 24 mutated with the substitution.

14. The bacterium of claim 1,
wherein the protein encoded by the ybdK gene has an amino acid sequence that is at least 99% identical to the amino acid sequence of SEQ ID NO: 16,
wherein the protein encoded by the gshA gene has an amino acid sequence that is at least 99% identical to the amino acid sequence of SEQ ID NO: 24,
wherein the γ-glutamyltransferase has an amino acid sequence that is at least 99% identical to the amino acid sequence of SEQ ID NO: 26, and
wherein the γ-glutamylvaline synthetase has an amino acid sequence that is at least 99% identical to the amino acid sequence of SEQ ID NO: 24 mutated with the substitution.

\* \* \* \* \*